(12) United States Patent
Tally et al.

(10) Patent No.: US 10,285,874 B2
(45) Date of Patent: *May 14, 2019

(54) MULTI-COMPONENT TOPSHEETS

(71) Applicant: The Procter & Gamble Company, Cincinnati, OH (US)

(72) Inventors: Amy Lynn Tally, Cold Spring, KY (US); Theresa Lynn Galie, Cincinnati, OH (US); George Christopher Dobrin, Mason, OH (US); Olaf Erik Alexander Isele, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 613 days.

This patent is subject to a terminal disclaimer.

(21) Appl. No.: 14/634,985

(22) Filed: Mar. 2, 2015

(65) Prior Publication Data
US 2015/0250661 A1 Sep. 10, 2015

Related U.S. Application Data

(60) Provisional application No. 62/112,337, filed on Feb. 5, 2015, provisional application No. 61/948,692, filed
(Continued)

(51) Int. Cl.
*A61F 13/511* (2006.01)
*A61F 13/512* (2006.01)
(Continued)

(52) U.S. Cl.
CPC ........ *A61F 13/5121* (2013.01); *A61F 13/512* (2013.01); *A61F 13/51104* (2013.01);
(Continued)

(58) Field of Classification Search
CPC ............ A61F 13/5121; A61F 13/51104; A61F 13/5116; A61F 13/51305; A61F 13/551;
(Continued)

(56) References Cited

U.S. PATENT DOCUMENTS 3,485,706 A 12/1969 Evans
3,542,634 A 11/1970 Such
(Continued)

FOREIGN PATENT DOCUMENTS

CA 2294922 12/1998
CN 1054897 7/2000
(Continued)

OTHER PUBLICATIONS

PCT International Search Report, dated May 27, 2015 (11 pages).
All Office Actions, U.S. Appl. No. 14/634,945.
All Office Actions, U.S. Appl. No. 14/634,928.

*Primary Examiner* — Adam Marcetich
*Assistant Examiner* — Jessica R Arble
(74) *Attorney, Agent, or Firm* — Christian M. Best; Andrew J. Mueller

(57) ABSTRACT

A multi-component topsheet for an absorbent article includes a first discrete substrate forming about 80% or more of an outer perimeter of the topsheet and a second discrete substrate wherein about 80% or more of an outer perimeter of the second discrete substrate is joined to the first discrete substrate, wherein the topsheet has a single layer of substrate in about 75% or more of the total area of the topsheet and a dual layer of substrate in about 25% or less of the total area of the topsheet.

22 Claims, 45 Drawing Sheets

Related U.S. Application Data on Mar. 6, 2014, provisional application No. 61/948,872, filed on Mar. 6, 2014.

(51) Int. Cl.
*A61F 13/513* (2006.01)
*A61F 13/84* (2006.01)

(52) U.S. Cl.
CPC .............. *A61F 13/51305* (2013.01); *A61F 2013/51178* (2013.01); *A61F 2013/51333* (2013.01); *A61F 2013/8491* (2013.01)

(58) Field of Classification Search
CPC .... A61F 2013/51178; A61F 2013/5307; A61F 2013/8491; A61F 2013/8497; A61F 13/5123
See application file for complete search history.

(56) References Cited

U.S. PATENT DOCUMENTS

| | | |
|---|---|---|
| 3,860,003 A | 1/1975 | Buell |
| 3,929,135 A | 12/1975 | Thompson |
| 4,041,951 A | 8/1977 | Sanford |
| 4,324,246 A | 4/1982 | Mullane |
| 4,342,314 A | 8/1982 | Radel |
| 4,463,045 A | 7/1984 | Ahr |
| 4,558,888 A | 12/1985 | Hanson et al. |
| 4,589,876 A | 5/1986 | Van Tilburg |
| 4,704,112 A | 11/1987 | Suzuki et al. |
| 4,731,066 A | 3/1988 | Korpman |
| 4,773,905 A | 9/1988 | Molel et al. |
| 4,780,352 A | 10/1988 | Palumbo |
| 4,859,519 A | 8/1989 | Cabe, Jr. |
| 4,868,958 A | 9/1989 | Suzuki et al. |
| 4,950,264 A | 8/1990 | Osborn, III |
| 5,009,653 A | 4/1991 | Osborn, III |
| 5,135,521 A | 8/1992 | Luceri et al. |
| 5,158,819 A | 10/1992 | Goodman, Jr. et al. |
| 5,221,274 A | 6/1993 | Buell et al. |
| 5,252,374 A | 10/1993 | Larsonneur |
| 5,264,268 A | 11/1993 | Luceri |
| 5,275,590 A | 1/1994 | Huffman et al. |
| 5,352,217 A | 10/1994 | Curro |
| H1376 H | 11/1994 | Osborn et al. |
| H1377 H | 11/1994 | Perry |
| 5,368,926 A | 11/1994 | Thompson |
| 5,415,640 A | 5/1995 | Kirby |
| 5,433,715 A | 7/1995 | Tanzer et al. |
| 5,449,352 A | 9/1995 | Nishino |
| 5,522,811 A | 6/1996 | Igaue |
| 5,533,991 A | 7/1996 | Kirby et al. |
| 5,554,145 A | 9/1996 | Roe et al. |
| 5,562,647 A | 10/1996 | Oetjen |
| 5,569,234 A | 10/1996 | Buell et al. |
| 5,580,411 A | 12/1996 | Nease et al. |
| 5,591,149 A | 1/1997 | Brown et al. |
| 5,599,335 A | 2/1997 | Goldman et al. |
| 5,607,414 A | 3/1997 | Richards et al. |
| 5,613,962 A | 3/1997 | Kenmochi |
| 5,628,097 A | 5/1997 | Benson |
| 5,643,240 A | 7/1997 | Jackson et al. |
| 5,647,862 A | 7/1997 | Cree et al. |
| 5,662,633 A | 9/1997 | Doak et al. |
| 5,669,895 A | 9/1997 | Masuda et al. |
| 5,674,591 A | 10/1997 | James |
| 5,700,254 A | 12/1997 | McDowall et al. |
| 5,702,382 A | 12/1997 | Hines et al. |
| 5,713,884 A | 2/1998 | Osborn, III et al. |
| 5,743,776 A | 4/1998 | Igaue et al. |
| 5,746,729 A | 5/1998 | Wada et al. |
| 5,779,692 A | 7/1998 | Hines et al. |
| 5,788,684 A | 8/1998 | Abuto et al. |
| 5,795,349 A | 8/1998 | Hines et al. |
| 5,810,798 A | 9/1998 | Dilnik et al. |
| 5,824,004 A | 10/1998 | Chappel et al. |
| 5,833,679 A | 11/1998 | Wada |
| 5,846,230 A | 12/1998 | Cree et al. |
| 5,846,232 A | 12/1998 | Serbiak et al. |
| 5,942,080 A | 8/1999 | Mortellite et al. |
| 5,961,505 A * | 10/1999 | Coe .............. A61F 13/534 604/358 |
| 5,962,106 A | 10/1999 | DeCarvalho et al. |
| 5,972,806 A | 10/1999 | Cree et al. |
| 5,990,375 A | 11/1999 | Bohm et al. |
| 5,990,377 A | 11/1999 | Chen et al. |
| 6,004,306 A | 12/1999 | Robles et al. |
| 6,004,893 A | 12/1999 | Van Tilburg |
| 6,013,348 A | 1/2000 | Takai |
| 6,025,049 A | 2/2000 | Ouelette et al. |
| 6,048,600 A | 4/2000 | Hansson |
| 6,059,764 A * | 5/2000 | Osborn, III ....... A61F 13/47218 604/385.22 |
| 6,090,089 A | 7/2000 | Tsuji |
| 6,103,953 A | 8/2000 | Buell et al. |
| 6,107,539 A | 8/2000 | Meyer et al. |
| 6,117,523 A | 9/2000 | Sugahara |
| 6,214,147 B1 | 4/2001 | Mortellite et al. |
| 6,264,642 B1 | 7/2001 | Kuen et al. |
| 6,274,218 B1 | 8/2001 | Shimizu |
| 6,277,104 B1 | 8/2001 | Lasko et al. |
| 6,287,288 B1 | 9/2001 | Osborn et al. |
| 6,320,096 B1 | 11/2001 | Inoue et al. |
| 6,436,082 B1 | 8/2002 | Mizutani |
| 6,436,083 B1 | 8/2002 | Mishima et al. |
| 6,446,495 B1 | 9/2002 | Herrlein et al. |
| 6,461,339 B1 | 10/2002 | Sugahara |
| 6,465,711 B1 | 10/2002 | Brisebois |
| 6,570,056 B1 | 5/2003 | Tanzer et al. |
| 6,573,423 B1 | 6/2003 | Herrlein et al. |
| 6,610,900 B1 | 8/2003 | Tanzer |
| 6,623,468 B2 | 9/2003 | Shimoe |
| 6,623,586 B2 | 9/2003 | Mortellite et al. |
| 6,628,777 B1 | 9/2003 | McIllwaine et al. |
| 6,632,504 B1 | 10/2003 | Gillespie et al. |
| 6,685,688 B2 | 2/2004 | Mishima et al. |
| 6,686,512 B2 | 2/2004 | Herrlein et al. |
| 6,702,800 B1 | 3/2004 | Vukos et al. |
| 6,733,610 B2 | 5/2004 | Mizutani et al. |
| 6,762,340 B2 | 7/2004 | Furuya et al. |
| 6,824,853 B1 | 11/2004 | Levine et al. |
| 6,840,928 B2 | 1/2005 | Datta et al. |
| 6,911,574 B1 | 6/2005 | Mizutani |
| 6,932,798 B2 | 8/2005 | Kudo et al. |
| 6,939,334 B2 | 9/2005 | Odorzynski et al. |
| 6,972,011 B2 | 12/2005 | Maeda et al. |
| 6,974,891 B2 | 12/2005 | Wallstrom |
| 7,060,344 B2 | 6/2006 | Pourdeyhimi |
| 7,102,054 B1 | 9/2006 | Cree et al. |
| 7,122,024 B2 | 10/2006 | Nakajima et al. |
| 7,163,528 B2 | 1/2007 | Christon et al. |
| 7,267,860 B2 | 9/2007 | Toyoshima et al. |
| D558,335 S | 12/2007 | Willhaus |
| 7,311,696 B2 | 12/2007 | Christon et al. |
| 7,371,919 B1 | 5/2008 | Busam et al. |
| 7,388,123 B2 | 6/2008 | Cowell et al. |
| 7,402,157 B2 | 7/2008 | Christon et al. |
| 7,422,991 B2 | 9/2008 | Baldauf et al. |
| 7,537,585 B2 | 5/2009 | Christon et al. |
| 7,569,264 B2 | 8/2009 | Toyoshima et al. |
| 7,589,249 B2 | 9/2009 | Gubernick et al. |
| 7,604,624 B2 | 10/2009 | Veith et al. |
| D603,611 S | 11/2009 | Cain et al. |
| 7,628,777 B2 | 12/2009 | Kondo et al. |
| 7,670,325 B2 | 3/2010 | Sugiyama et al. |
| 7,670,665 B2 | 3/2010 | Hoying et al. |
| 7,704,901 B2 | 4/2010 | Baldauf et al. |
| 7,712,640 B2 | 5/2010 | Honer et al. |
| 7,750,203 B2 | 7/2010 | Becker et al. |
| 7,767,876 B2 | 8/2010 | Davis et al. |
| 7,781,640 B2 | 8/2010 | Davis et al. |
| 7,785,310 B2 | 8/2010 | Sakano et al. |
| 7,786,340 B2 | 8/2010 | Gagiardi et al. |
| D624,179 S | 9/2010 | Molas et al. |

(56) References Cited

U.S. PATENT DOCUMENTS

| | | |
|---|---|---|
| 7,824,385 B2 | 11/2010 | Ecker et al. |
| 7,867,210 B2 | 1/2011 | Mori et al. |
| 7,935,861 B2 | 5/2011 | Suzuki |
| 7,967,801 B2 | 6/2011 | Hammons et al. |
| 7,972,317 B2 | 7/2011 | Christon et al. |
| D642,382 S | 8/2011 | Cain et al. |
| 7,993,317 B2 | 8/2011 | Hammons et al. |
| 7,993,319 B2 | 8/2011 | Sperl |
| 8,030,535 B2 | 10/2011 | Hammons et al. |
| 8,057,450 B2 | 11/2011 | Roe et al. |
| 8,057,455 B2 | 11/2011 | Shirai et al. |
| 8,058,501 B2 | 11/2011 | Hammons et al. |
| 8,105,300 B2 | 1/2012 | Christon et al. |
| 8,178,748 B2 | 5/2012 | Hammons et al. |
| 8,211,076 B2 | 7/2012 | Sugiyama et al. |
| 8,251,965 B2 | 8/2012 | Costea et al. |
| 8,257,330 B2 | 9/2012 | Christon et al. |
| 8,328,780 B2 | 12/2012 | Morman et al. |
| 8,377,023 B2 | 2/2013 | Sawyer et al. |
| D679,006 S | 3/2013 | Fuchs et al. |
| D679,808 S | 4/2013 | Hood et al. |
| D681,197 S | 4/2013 | Johnson et al. |
| D681,199 S | 4/2013 | Cutshaw et al. |
| D681,200 S | 4/2013 | Cutshaw et al. |
| 8,435,924 B2 | 5/2013 | Arora et al. |
| 8,439,886 B2 | 5/2013 | Hashimo et al. |
| D682,420 S | 6/2013 | Mason et al. |
| D684,262 S | 6/2013 | Mason et al. |
| 8,461,411 B2 | 6/2013 | DiGiacomantonio et al. |
| D686,317 S | 7/2013 | Bogren et al. |
| D686,319 S | 7/2013 | Hawes et al. |
| D686,320 S | 7/2013 | Hawes et al. |
| 8,481,806 B2 | 7/2013 | Ueminami et al. |
| 8,486,036 B2 | 7/2013 | Tange et al. |
| 8,491,556 B2 | 7/2013 | Popp et al. |
| 8,492,609 B2 | 7/2013 | Ecker et al. |
| 8,536,401 B2 | 9/2013 | Ecker et al. |
| 8,541,644 B2 | 9/2013 | Raidel et al. |
| D691,715 S | 10/2013 | Mason et al. |
| D692,130 S | 10/2013 | Biggs et al. |
| 8,546,642 B2 | 10/2013 | Biggs et al. |
| 8,556,874 B2 | 10/2013 | Christon et al. |
| 8,563,802 B2 | 10/2013 | Nishikawa et al. |
| 8,569,568 B2 | 10/2013 | Roe et al. |
| 8,569,572 B2 | 10/2013 | Hammons et al. |
| D693,922 S | 11/2013 | Frias et al. |
| 8,575,419 B2 | 11/2013 | DiVirgilio et al. |
| 8,585,666 B2 | 11/2013 | Weisman et al. |
| 8,591,487 B2 | 11/2013 | Nishitani et al. |
| D695,894 S | 12/2013 | Bruno |
| 8,748,692 B2 | 6/2014 | Suzuki |
| 8,865,965 B2 | 10/2014 | Sato et al. |
| 9,072,634 B2 | 7/2015 | Hundorf et al. |
| 9,220,638 B2 | 12/2015 | Hammons et al. |
| 2001/0026861 A1 | 10/2001 | Takai |
| 2002/0123728 A1 | 9/2002 | Graef et al. |
| 2002/0138054 A1 | 9/2002 | Erdman |
| 2003/0097107 A1 | 5/2003 | Sprengard-Eichel |
| 2003/0125696 A1 | 7/2003 | Morman et al. |
| 2003/0167044 A1 | 9/2003 | Toyoshima |
| 2003/0187415 A1 | 10/2003 | Ito et al. |
| 2004/0039363 A1 | 2/2004 | Sugiyama et al. |
| 2004/0054343 A1 | 3/2004 | Barnett et al. |
| 2004/0116029 A1 | 6/2004 | Kelly |
| 2004/0142151 A1* | 7/2004 | Toyoshima ............ D04H 3/14 428/172 |
| 2005/0003152 A1 | 1/2005 | Thomas |
| 2005/0084439 A1 | 4/2005 | Imamura et al. |
| 2005/0124961 A1 | 6/2005 | Morman et al. |
| 2005/0148975 A1 | 7/2005 | Van Gompel et al. |
| 2005/0154362 A1 | 7/2005 | Warren et al. |
| 2005/0215155 A1 | 9/2005 | Young |
| 2006/0216473 A1 | 9/2006 | Tomany et al. |
| 2007/0048709 A1 | 3/2007 | Ales et al. |
| 2007/0142812 A1 | 6/2007 | Popp et al. |
| 2007/0233027 A1 | 10/2007 | Roe et al. |
| 2007/0298220 A1 | 12/2007 | Noda et al. |
| 2008/0004581 A1 | 1/2008 | Babusik et al. |
| 2008/0114317 A1 | 5/2008 | Seyler |
| 2008/0249495 A1 | 10/2008 | Oi Virgilio |
| 2008/0294138 A1 | 11/2008 | Andersson et al. |
| 2008/0300564 A1 | 12/2008 | Bogren et al. |
| 2008/0312622 A1 | 12/2008 | Hundorf et al. |
| 2008/0312623 A1 | 12/2008 | Hundorf |
| 2009/0030390 A1 | 6/2009 | Hammons et al. |
| 2009/0030391 A1 | 6/2009 | Hammons et al. |
| 2009/0306614 A1 | 12/2009 | Boissier |
| 2009/0306615 A1 | 12/2009 | Olsson |
| 2010/0004615 A1 | 1/2010 | Boissier |
| 2010/0036338 A1 | 2/2010 | Hammons et al. |
| 2010/0063471 A1 | 3/2010 | Minato et al. |
| 2010/0069871 A1 | 3/2010 | Minato et al. |
| 2010/0106127 A1 | 4/2010 | Minato et al. |
| 2010/0130952 A1 | 5/2010 | Murai |
| 2010/0209664 A1 | 8/2010 | Sato et al. |
| 2010/0249740 A1 | 9/2010 | Miyamoto et al. |
| 2011/0046596 A1 | 2/2011 | Kudo et al. |
| 2011/0073513 A1 | 3/2011 | Weisman |
| 2011/0106036 A1 | 5/2011 | Stahl et al. |
| 2011/0160691 A1 | 6/2011 | Ng et al. |
| 2011/0196330 A1 | 8/2011 | Hammons et al. |
| 2012/0059343 A1 | 3/2012 | Kume |
| 2012/0064280 A1* | 3/2012 | Hammons .......... A61F 13/15707 428/85 |
| 2012/0095426 A1 | 4/2012 | Visscher et al. |
| 2012/0100350 A1 | 4/2012 | Shim |
| 2012/0226250 A1 | 9/2012 | Sato et al. |
| 2012/0296304 A1 | 11/2012 | Choo et al. |
| 2012/0310199 A1 | 12/2012 | Larson et al. |
| 2012/0310200 A1 | 12/2012 | Christon et al. |
| 2013/0116646 A1 | 5/2013 | Robles |
| 2013/0131620 A1 | 5/2013 | Hisanaka et al. |
| 2013/0158494 A1 | 6/2013 | Ong et al. |
| 2013/0184667 A1 | 7/2013 | Larson et al. |
| 2013/0184668 A1 | 7/2013 | Hood et al. |
| 2013/0211362 A1 | 8/2013 | Mason et al. |
| 2013/0226123 A1 | 8/2013 | Kudo et al. |
| 2013/0245587 A1 | 9/2013 | DiGiacomantonio et al. |
| 2013/0261584 A1 | 10/2013 | Lee et al. |
| 2013/0261585 A1* | 10/2013 | Lee .................... A61F 13/8405 604/385.01 |
| 2013/0261586 A1* | 10/2013 | Lee .................... A61F 13/8405 604/385.01 |
| 2013/0296820 A1 | 11/2013 | Hughes et al. |
| 2013/0310784 A1 | 11/2013 | Bryant et al. |
| 2014/0005625 A1 | 1/2014 | Wirtz et al. |
| 2014/0031779 A1 | 1/2014 | Hammons et al. |
| 2014/0039434 A1 | 2/2014 | Xu et al. |
| 2014/0039438 A1 | 2/2014 | Ferrer et al. |
| 2014/0121623 A1* | 5/2014 | Kirby ............... A61F 13/51108 604/383 |
| 2014/0121626 A1 | 5/2014 | Finn et al. |
| 2014/0127459 A1 | 5/2014 | Xu et al. |
| 2014/0127460 A1 | 5/2014 | Xu et al. |
| 2014/0127461 A1 | 5/2014 | Xu et al. |
| 2014/0163500 A1 | 6/2014 | Roe et al. |
| 2014/0163503 A1 | 6/2014 | Arizti et al. |
| 2014/0163507 A1* | 6/2014 | Kudo ................ A61F 13/4756 604/379 |
| 2014/0296815 A1 | 10/2014 | Takken |
| 2014/0336608 A1 | 11/2014 | Hao |
| 2014/0343525 A1 | 11/2014 | Roh |
| 2015/0038933 A1 | 2/2015 | Lee et al. |
| 2015/0038934 A1 | 2/2015 | Lee et al. |
| 2015/0039020 A1 | 2/2015 | ValMalderen |
| 2015/0250658 A1 | 9/2015 | Tally |
| 2015/0250659 A1 | 9/2015 | Tally |

(56) References Cited

U.S. PATENT DOCUMENTS

| | | |
|---|---|---|
| 2015/0250663 A1 | 9/2015 | Wagner |
| 2015/0290050 A1 | 10/2015 | Wada |

FOREIGN PATENT DOCUMENTS

| | | |
|---|---|---|
| CN | 1132561 | 12/2003 |
| CN | 1164248 | 9/2004 |
| CN | 1197538 | 4/2005 |
| CN | 1280086 | 10/2006 |
| CN | 1280470 | 10/2006 |
| CN | 1290478 | 12/2006 |
| CN | 1981723 | 6/2007 |
| CN | 1331661 | 8/2007 |
| CN | 101152114 | 4/2008 |
| CN | 100387212 | 5/2008 |
| CN | 100434055 | 11/2008 |
| CN | 100512784 | 7/2009 |
| CN | 100522122 | 8/2009 |
| CN | 1981724 | 5/2010 |
| CN | 201692175 | 1/2011 |
| CN | 1839776 | 4/2011 |
| CN | 201959103 | 9/2011 |
| CN | 102257199 | 11/2011 |
| CN | 1986210 | 6/2012 |
| CN | 101460129 | 6/2012 |
| CN | 102560904 | 7/2012 |
| CN | 101790606 | 9/2012 |
| CN | 102673030 | 9/2012 |
| CN | 202491475 | 10/2012 |
| CN | 202637294 U | 1/2013 |
| CN | 101674793 | 10/2013 |
| CN | 102271642 | 10/2013 |
| CN | 101310696 | 12/2013 |
| CN | 103417337 A | 12/2013 |
| CN | 103417338 A | 12/2013 |
| CN | 103422256 A | 12/2013 |
| CN | 103459693 | 12/2013 |
| CN | 203393410 U | 1/2014 |
| CN | 203400265 U | 1/2014 |
| CN | 103908376 A | 7/2014 |
| CN | 203841923 U | 9/2014 |
| EP | 1920232 | 4/2010 |
| EP | 2189562 | 5/2010 |
| EP | 2505173 | 10/2012 |
| GB | 2 262 235 A | 6/1993 |
| GB | 2 325 146 A | 11/1998 |
| GB | 2325146 | 11/1998 |
| JP | H4187146 | 7/1992 |
| JP | 8117273 A | 5/1996 |
| JP | 11197179 A | 7/1999 |
| JP | 3155351 B2 | 4/2001 |
| JP | 3437681 B2 | 8/2003 |
| JP | 3453031 | 10/2003 |
| JP | 3517852 B2 | 4/2004 |
| JP | 3587831 | 11/2004 |
| JP | 3611666 | 1/2005 |
| JP | 3611838 | 1/2005 |
| JP | 3740790 B2 | 2/2006 |
| JP | 3808032 | 8/2006 |
| JP | 3812460 B2 | 8/2006 |
| JP | 2007014705 | 1/2007 |
| JP | 3877682 | 2/2007 |
| JP | 3886400 | 2/2007 |
| JP | 3886466 | 2/2007 |
| JP | 3926250 | 6/2007 |
| JP | 3987691 B2 | 10/2007 |
| JP | 3989218 | 10/2007 |
| JP | 4023996 | 12/2007 |
| JP | 4090412 | 5/2008 |
| JP | 4178738 B2 | 11/2008 |
| JP | 4185389 B2 | 11/2008 |
| JP | 4278963 | 6/2009 |
| JP | 4346633 B2 | 10/2009 |
| JP | 4390406 B2 | 12/2009 |
| JP | 4390624 B2 | 12/2009 |
| JP | 4390747 | 12/2009 |
| JP | 4514630 | 7/2010 |
| JP | 4540567 | 9/2010 |
| JP | 4566109 | 10/2010 |
| JP | 4627500 B2 | 2/2011 |
| JP | 4627502 B2 | 2/2011 |
| JP | 4646878 | 3/2011 |
| JP | 4688103 | 5/2011 |
| JP | 4700507 B2 | 6/2011 |
| JP | 4716638 | 7/2011 |
| JP | 4716639 | 7/2011 |
| JP | 4746833 B2 | 8/2011 |
| JP | 4808504 B2 | 11/2011 |
| JP | 4975091 | 7/2012 |
| JP | 4990070 B2 | 8/2012 |
| JP | 5021719 | 9/2012 |
| JP | 5063412 B2 | 10/2012 |
| JP | 4808501 B2 | 11/2012 |
| JP | 5074854 | 11/2012 |
| JP | 5078325 | 11/2012 |
| JP | 5084434 | 11/2012 |
| JP | 5086035 B2 | 11/2012 |
| JP | 5086036 B2 | 11/2012 |
| JP | 5087419 | 12/2012 |
| JP | 5087432 | 12/2012 |
| JP | 5099752 | 12/2012 |
| JP | 5103100 | 12/2012 |
| JP | 5112047 | 1/2013 |
| JP | 5149057 | 2/2013 |
| JP | 5197147 | 5/2013 |
| JP | 5230238 B2 | 7/2013 |
| JP | 5394654 | 1/2014 |
| JP | 5410852 B2 | 2/2014 |
| JP | 5468654 B2 | 4/2014 |
| JP | 5528953 B2 | 6/2014 |
| WO | WO 1993-11725 A1 | 6/1993 |
| WO | WO 1994-02095 A1 | 2/1994 |
| WO | WO 1994-02096 A2 | 2/1994 |
| WO | WO94/20054 | 9/1994 |
| WO | WO 1996-23472 A1 | 8/1996 |
| WO | WO1996/036761 | 11/1996 |
| WO | WO 1998-15399 A1 | 4/1998 |
| WO | WO-1998058606 | 12/1998 |
| WO | WO 1999-00095 A1 | 1/1999 |
| WO | WO 2001-06974 A1 | 2/2001 |
| WO | WO2004/098869 | 11/2004 |
| WO | WO-2007027219 | 3/2007 |
| WO | WO 2010-0055699 A1 | 5/2010 |
| WO | WO 2011-0122710 A1 | 10/2011 |
| WO | WO 2012-0176656 A1 | 12/2012 |
| WO | WO2013/091150 | 6/2013 |
| WO | WO-2013/099625 | 7/2013 |
| WO | WO-2013/129167 | 9/2013 |
| WO | WO 2013147222 | 10/2013 |
| WO | WO 2013/175360 | 11/2013 |
| WO | WO-2013/191077 | 12/2013 |

* cited by examiner

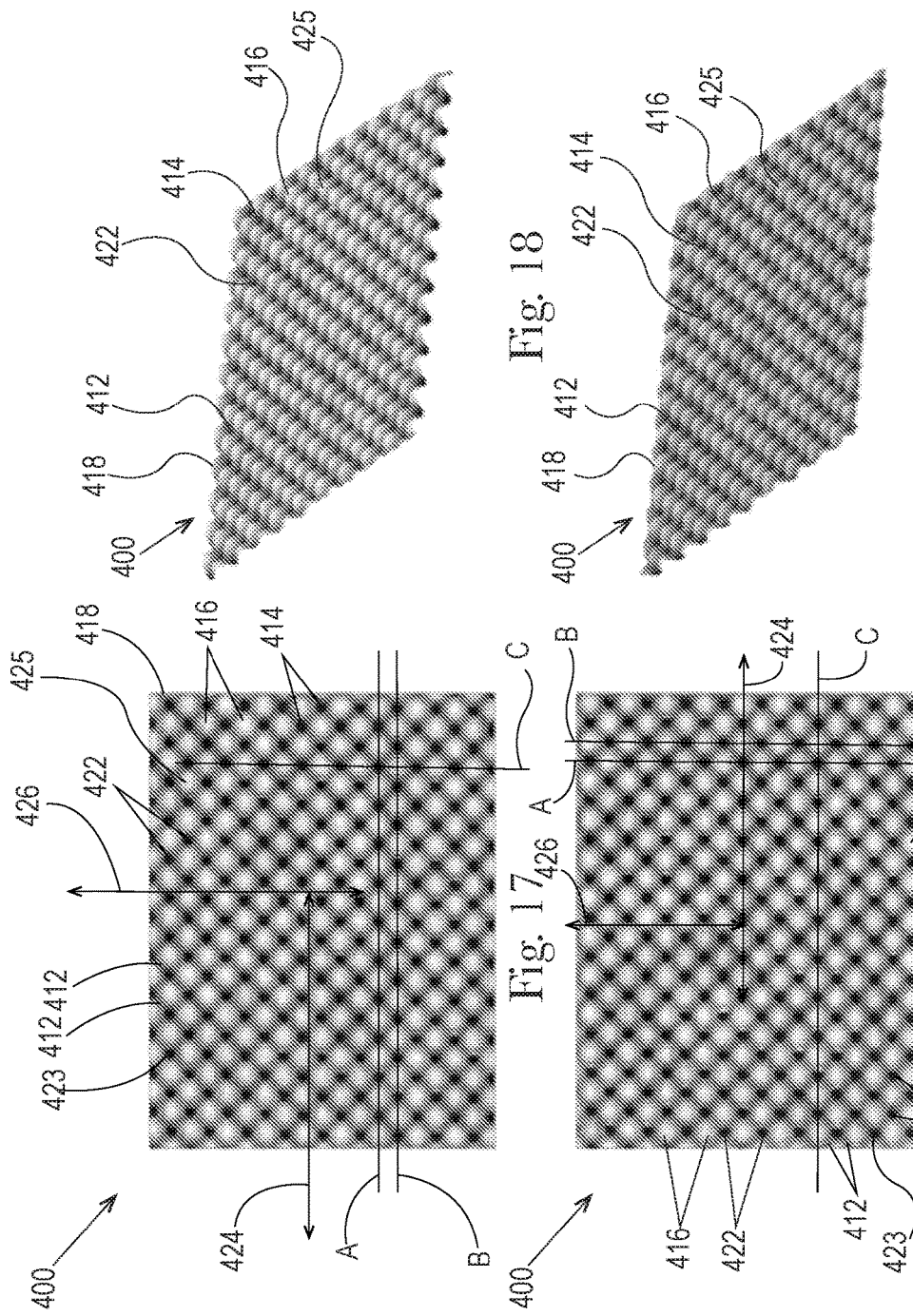

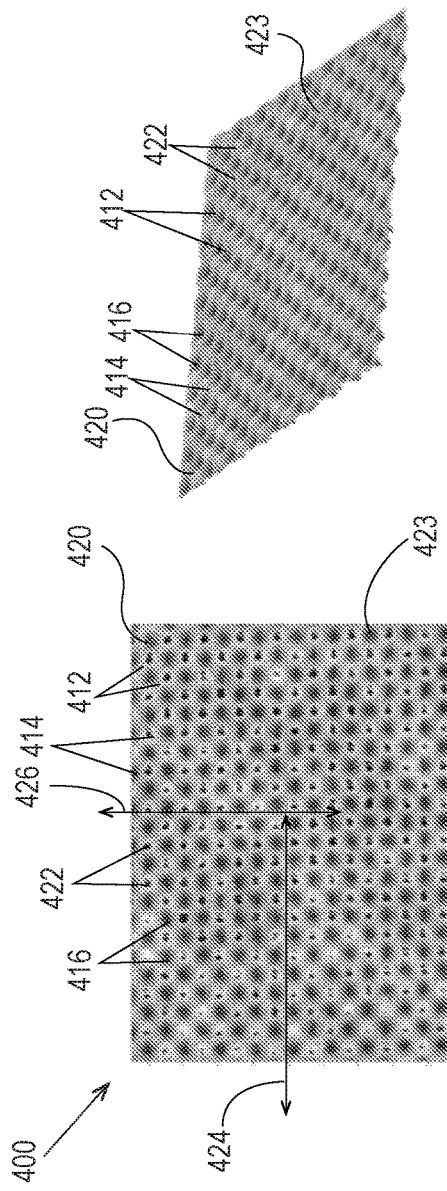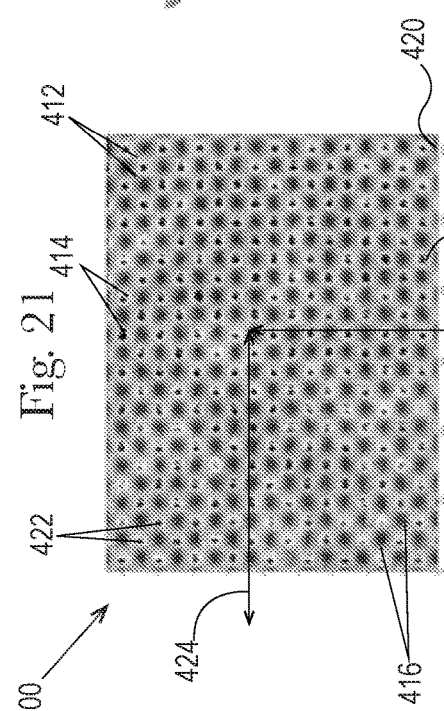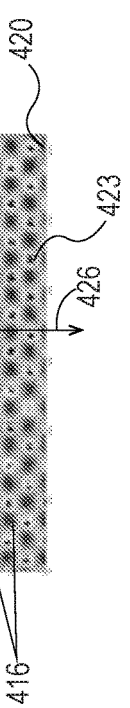

MULTI-COMPONENT TOPSHEETS

FIELD

The present disclosure is generally related to multi-component topsheets, and is more specifically related to multi-component topsheets for absorbent articles and/or absorbent articles comprising multi-component topsheets.

BACKGROUND

Absorbent articles for personal hygiene, such as disposable diapers for infants, training pants for toddlers, adult incontinence undergarments, and/or sanitary napkins are designed to absorb and contain body exudates, in particular large quantities of urine, runny BM, and/or menses (together the "fluids"). These absorbent articles may comprise several layers providing different functions, for example, a topsheet, a backsheet, and an absorbent core disposed between the topsheet and the backsheet, among other layers (e.g., acquisition layer, distribution layer, etc.), if desired.

The topsheet is generally liquid permeable and is configured to receive the fluids being excreted from the body and aid in directing the fluids toward an acquisition system, a distribution system, and/or the absorbent core. In general, topsheets may be made to be hydrophilic via a surfactant treatment applied thereto so that the fluids are attracted to the topsheet to then be channeled into the underlying acquisition system, distribution system, and/or the absorbent core. One of the important qualities of a topsheet is the ability to reduce ponding of the fluids on the topsheets before the fluids are able to be absorbed by the absorbent article. Stated another way, one design criteria of topsheets is to reduce the amount of time the fluids spend on topsheet prior to being absorbed by the absorbent article. If fluids remain on the surface of a topsheet for too long of a period of time, the wearer may not feel dry and skin discomfort may increase.

To solve the problem of the skin feeling wet during, for example, urination, because of prolonged fluid residency on the topsheets, apertured topsheets have been used to allow for faster fluid penetration. Although apertured topsheets have generally reduced fluid pendency on topsheets, topsheets can still be further improved by providing three-dimensional substrates that further reduce skin/fluid contact and/or skin/fluid contact time during, for example, a urination event.

Moreover, three-dimensional substrates, or other improved apertured topsheet materials, can be relatively expensive when compared to traditional topsheet materials. Accordingly, it is of continued interest to be able to attain the benefits of using three-dimensional substrates as topsheet materials, while limiting the added expense of employing such materials.

SUMMARY

The present disclosure is generally related, in part, to three-dimensional substrates that may be applied to topsheets of absorbent articles, form portions of, or all of, the topsheets, or form other portions of absorbent articles. The three-dimensional substrates may be liquid permeable substrates. The three-dimensional substrates of the present disclosure may reduce fluid/skin contact and/or fluid/skin contact time by providing first elements having a first z-directional height and at least second elements having a second z-directional height. These substrates may also comprise apertures. The first z-directional height may generally be higher than the second z-directional height. Such a structure creates a substrate having a plurality of heights. These three-dimensional substrates may allow fluids, during a urination event, for example, to be received onto the substrate and moved into the second elements having the second z-directional height (lower) and/or into and through the apertures to at least reduce the amount of fluid in contact with the skin and/or to at least reduce the fluid/skin contact time. Stated another way, the first elements having the first z-directional height (higher) may be in contact with the skin, while the fluids moves via gravity into the second elements having the second z-directional height (lower height) and/or into and through the apertures. Upon information and belief, such three-dimensional structures reduce the amount of fluid on skin, give the wearer a drier, more comfortable feel, and/or reduce the pendency of fluid/skin contact. The first elements having the first z-directional height (higher) essentially serve to provide a spacer between the skin and the fluids while the substrates are channeling the fluids into the acquisition and/or distribution system and/or the absorbent core.

In one embodiment, a multi-component topsheet for an absorbent article includes a first discrete substrate forming about 80% or more of an outer perimeter of the topsheet and a second discrete substrate wherein about 80% or more of an outer perimeter of the second discrete substrate is joined to the first discrete substrate, wherein the topsheet has a single layer of substrate in about 75% or more of the total area of the topsheet and a dual layer of substrate in about 25% or less of the total area of the topsheet, wherein the dual layer of substrate is formed from an overlap between the first discrete substrate and the second discrete substrate, wherein the second discrete substrate comprises a plurality of recesses and projections, wherein the plurality of recesses and projections together form a first three-dimensional surface on a first side of the second discrete substrate and a second three-dimensional surface on a second side of the substrate, wherein a majority of the projections have, according to the Projection Height Test, a z-dimensional height of between about 500 µm and about 4000 µm, and wherein a majority of the recesses define an aperture at a location most distal from a top surface of an adjacent projection, a majority of the recesses having, according to the Recess Height Test, a z-directional height of between about 500 µm and about 2000 µm.

In another embodiment, a multi-component topsheet for an absorbent article includes a first discrete substrate forming about 80% or more of an outer perimeter of the topsheet and a second discrete substrate wherein about 80% or more of an outer perimeter of the second discrete substrate is joined to the first discrete substrate, wherein the topsheet has a single layer of substrate in about 75% or more of the total area of the topsheet and a dual layer of substrate in about 25% or less of the total area of the topsheet, wherein the dual layer of substrate is formed from an overlap between the first discrete substrate and the second discrete substrate, wherein the second discrete substrate comprises a plurality of recesses and projections, wherein the plurality of recesses and projections together form a first three-dimensional surface on a first side of the second discrete substrate and a second three-dimensional surface on a second side of the substrate, wherein a majority of the projections have, according to the Projection Height Test, a z-dimensional height of between about 500 µm and about 4000 µm, and wherein a majority of the recesses define an aperture at a location most distal from a top surface of an adjacent projection, a majority of the recesses having, according to the Recess Height Test, a z-directional height of between about 500 µm and about 2000 µm.

In another embodiment, an absorbent article includes a multi-component topsheet for an absorbent article includes a first discrete substrate forming about 80% or more of an outer perimeter of the topsheet, and a second discrete substrate wherein about 80% or more of an outer perimeter of the second discrete substrate is joined to the first discrete substrate, wherein the topsheet has a single layer of substrate in about 75% or more of the total area of the topsheet and a dual layer of substrate in about 25% or less of the total area of the topsheet, wherein the dual layer of substrate is formed from an overlap between the first discrete substrate and the second discrete substrate, wherein the second discrete substrate comprises a plurality of recesses and projections, wherein the plurality of recesses and projections together form a first three-dimensional surface on a first side of the second discrete substrate and a second three-dimensional surface on a second side of the substrate, wherein a majority of the projections have, according to the Projection Height Test, a z-dimensional height of between about 500 µm and about 4000 µm, and wherein a majority of the recesses define an aperture at a location most distal from a top surface of an adjacent projection, a majority of the recesses having, according to the Recess Height Test, a z-directional height of between about 500 µm and about 2000 µm.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting forms of the disclosure taken in conjunction with the accompanying drawings, wherein:

FIG. 17 is a front view of a portion of a three-dimensional, liquid permeable substrate, wearer-facing surface facing the viewer in accordance with the present disclosure;

FIG. 18 is a front perspective view of the portion of the three-dimensional, liquid permeable substrate of FIG. 17 in accordance with the present disclosure;

FIG. 19 is another front view of a portion of a three-dimensional, liquid permeable substrate, wearer-facing surface facing the viewer in accordance with the present disclosure;

FIG. 20 is a front perspective view of the portion of the liquid permeable substrate of FIG. 19 in accordance with the present disclosure;

FIG. 21 is a back view of a portion of a three-dimensional, liquid permeable substrate, wearer-facing surface facing the viewer in accordance with the present disclosure;

FIG. 22 is a back perspective view of the portion of the three-dimensional, liquid permeable substrate of FIG. 21 in accordance with the present disclosure;

FIG. 23 is another back view of a portion of a three-dimensional, liquid permeable substrate, wearer-facing surface facing the viewer in accordance with the present disclosure;

FIG. 24 is a back perspective view of the portion of the liquid permeable substrate of FIG. 23 in accordance with the present disclosure;

DETAILED DESCRIPTION

Figure 1:
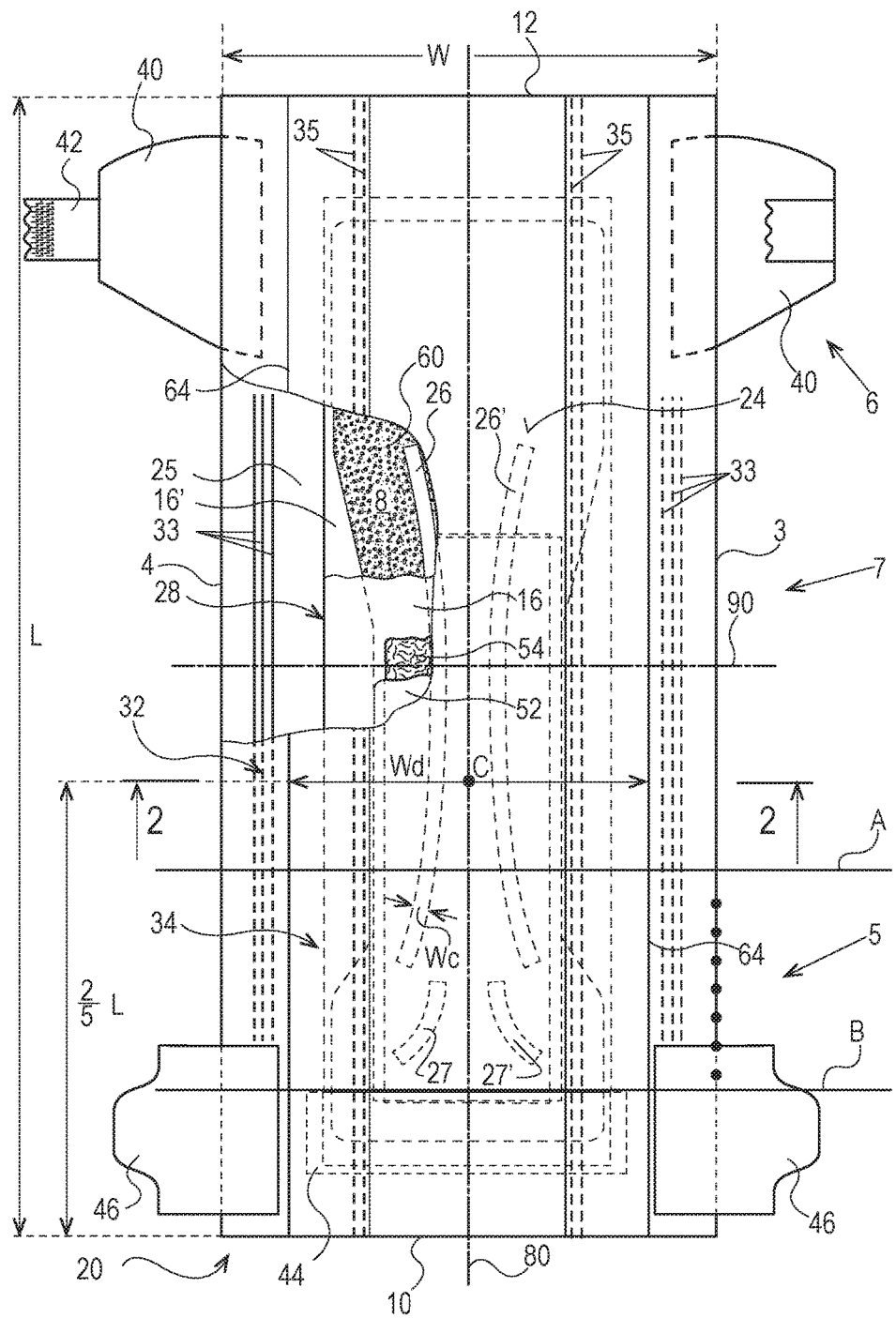
FIG. 1 is a top view of an absorbent article, wearer-facing surface facing the viewer, with some layers partially removed in accordance with the present disclosure.

Various non-limiting forms of the present disclosure will now be described to provide an overall understanding of the principles of the structure, function, manufacture, and use of the three-dimension substrates disclosed herein. One or more examples of these non-limiting embodiments are illustrated in the accompanying drawings. Those of ordinary skill in the art will understand that the three-dimensional substrates described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

Introduction

As used herein, the term "absorbent article" refers to disposable devices such as infant, child, or adult diapers, adult incontinence products, training pants, sanitary napkins, and the like which are placed against or in proximity to a body of a wearer to absorb and contain the various fluids (urine, menses, and/or runny BM) or bodily exudates (generally solid BM) discharged from the body. Typically, these absorbent articles comprise a topsheet, backsheet, an absorbent core, optionally an acquisition system and/or a distribution system (which may be comprised of one or several layers), and typically other components, with the absorbent core normally placed at least partially between the backsheet and the acquisition and/or distribution system or between the topsheet and the backsheet. The absorbent articles comprising three-dimensional, liquid permeable substrates of the present disclosure will be further illustrated in the below description and in the Figures in the form of one or more components of taped diaper. Nothing in this description should be, however, considered limiting the scope of the claims. As such the present disclosure applies to any suitable form of absorbent articles (e.g., diapers, training pants, adult incontinence products, sanitary napkins).

As used herein, the term "nonwoven web" means a manufactured sheet, web, or batt of directionally or randomly orientated fibers, bonded by friction, and/or cohesion, and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers may have diameters ranging from less than about 0.001 mm to more than about 0.2 mm and may come in several different forms such as short fibers (known as staple, or chopped), continuous single fibers (filaments or monofilaments), untwisted bundles of continuous filaments (tow), and twisted bundles of continuous filaments (yarn). Nonwoven webs may be formed by many processes such as meltblowing, spunbonding, solvent spinning, electrospinning, carding, and airlaying. The basis weight of nonwoven webs is usually expressed in grams per square meter (g/m$^2$ or gsm).

As used herein, the terms "joined", "bonded", or "attached" encompasses configurations whereby an element is directly secured to another element by affixing the element directly to the other element, and configurations whereby an element is indirectly secured to another element by affixing the element to intermediate member(s) which in turn are affixed to the other element.

As used herein, the term "machine direction" or "MD" is the direction that is substantially parallel to the direction of travel of a substrate as it is made. The "cross direction" or "CD" is the direction substantially perpendicular to the MD and in the plane generally defined by the substrate.

As used herein, the term "hydrophilic", refers to a material having a contact angle less than or equal to 90° according to The American Chemical Society Publication "Contact Angle, Wettability, and Adhesion," edited by Robert F. Gould and copyrighted in 1964.

As used herein, the term "hydrophobic", refers to a material or layer having a contact angle greater than or equal to 90° according to The American Chemical Society Publication "Contact Angle, Wettability, and Adhesion," edited by Robert F. Gould and copyrighted in 1964.

General Description of the Absorbent Article

Figure 2:
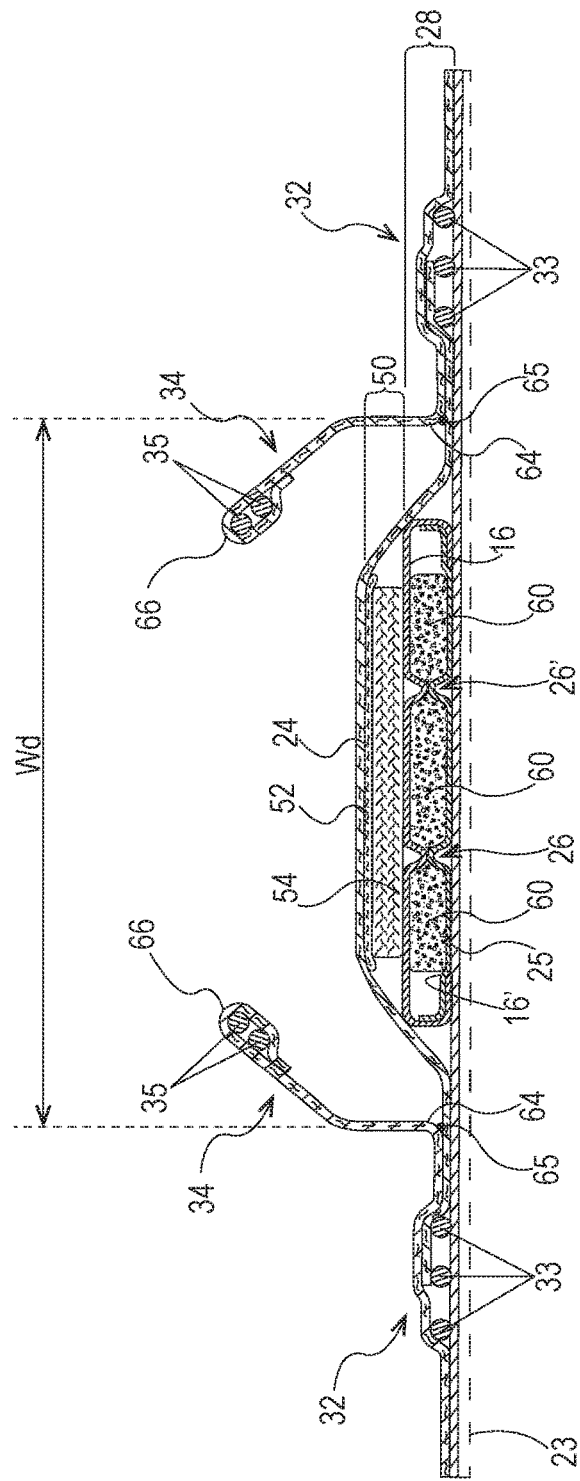
FIG. 2 is a cross-sectional view of the absorbent article taken about line 2-2 of FIG. 1 in accordance with the present disclosure.
Figure 3:
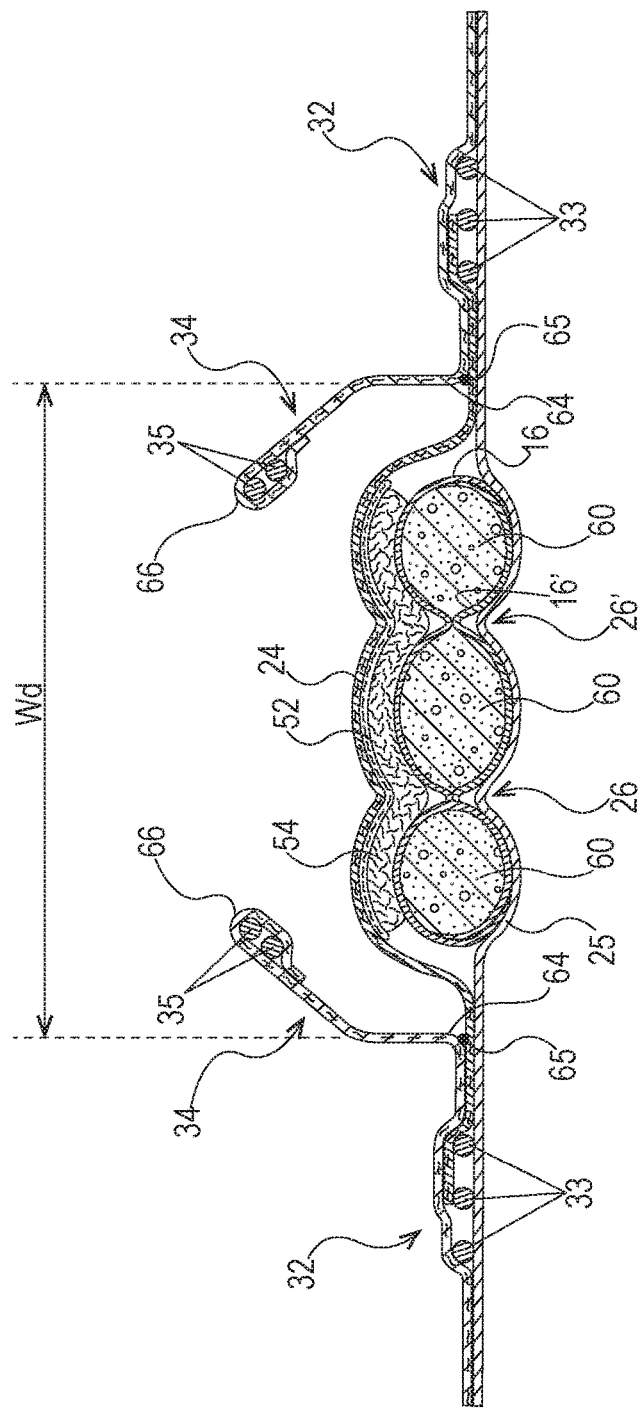
FIG. 3 is a cross-sectional view of the absorbent article taken about line 2-2 of FIG. 2 where the absorbent article has been loaded with fluid in accordance with the present disclosure.

An example absorbent article in the form of a diaper 20 is represented in FIGS. 1-3. FIG. 1 is a plan view of the example diaper 20, in a flat-out state, with portions of the structure being cut-away to more clearly show the construction of the diaper 20. The wearer-facing surface of the diaper 20 of FIG. 1 is facing the viewer. This diaper 20 is shown for illustration purpose only as the three-dimensional substrates of the present disclosure may be used as one or more components of an absorbent article.

The absorbent article 20 may comprise a liquid permeable topsheet 24, a liquid impermeable backsheet 25, an absorbent core 28 positioned at least partially intermediate the topsheet 24 and the backsheet 25, and barrier leg cuffs 34. The absorbent article may also comprise an acquisition and/or distribution system ("ADS") 50, which in the example represented comprises a distribution layer 54 and an acquisition layer 52, which will be further detailed below. The absorbent article may also comprise elasticized gasketing cuffs 32 comprising elastics 33 joined to a chassis of the absorbent article, typically via the topsheet and/or backsheet, and substantially planar with the chassis of the diaper.

The figures also show typical taped diaper components such as a fastening system comprising tabs 42 attached towards the rear edge of the article and cooperating with a landing zone 44 on the front of the absorbent article. The absorbent article may also comprise other typical elements, which are not represented, such as a rear elastic waist feature, a front elastic waist feature, transverse barrier cuff(s), and/or a lotion application, for example.

The absorbent article 20 comprises a front waist edge 10, a rear waist edge 12 longitudinally opposing the front waist edge 10, a first side edge 3, and a second side edge 4 laterally opposing the first side edge 3. The front waist edge 10 is the edge of the article which is intended to be placed towards the front of the user when worn, and the rear waist edge 12 is the opposite edge. The absorbent article may have a longitudinal axis 80 extending from the lateral midpoint of the front waist edge 10 to a lateral midpoint of the rear waist edge 12 of the article and dividing the article in two substantially symmetrical halves relative to the longitudinal axis 80, with the article placed flat and viewed from above as in FIG. 1. The absorbent article may also have a lateral axis 90 extending from the longitudinal midpoint of the first side edge 3 to the longitudinal midpoint of the second side edge 4. The length, L, of the article may be measured along the longitudinal axis 80 from the front waist edge 10 to the rear waist edge 12. The width, W, of the article may be measured along the lateral axis 90 from the first side edge 3 to the second side edge 4. The article may comprise a crotch point C defined herein as the point placed on the longitudinal axis at a distance of two fifth (2/5) of L starting from the front edge 10 of the article 20. The article may comprise a front waist region 5, a rear waist region 6, and a crotch region 7. The front waist region 5, the rear waist region 6, and the crotch region 7 each define 1/3 of the longitudinal length, L, of the absorbent article.

The topsheet 24, the backsheet 25, the absorbent core 28, and the other article components may be assembled in a variety of configurations, in particular by gluing or heat embossing, for example. Example absorbent article configurations are described generally in U.S. Pat. Nos. 3,860,003, 5,221,274, 5,554,145, 5,569,234, 5,580,411, and 6,004,306.

The absorbent core 28 may comprise an absorbent material comprising at least 80% by weight, at least 90% by weight, at least 95% by weight, or at least 99% by weight of superabsorbent polymers and a core wrap enclosing the superabsorbent polymers. The core wrap may typically comprise two materials, substrates, or nonwoven materials 16 and 16' for the top side and bottom side of the core. The core may comprises one or more channels, represented in FIG. 1 as the four channels 26, 26' and 27, 27'. The channels 26, 26', 27, and 27' are optional features. Instead, the core may not have any channels or may have any number of channels.

These and other components of the example absorbent article will now be discussed in more details.

Topsheet

In the present disclosure, the topsheet (the portion of the absorbent article that contacts the wearer's skin and receives the fluids) may be formed of a portion of, or all of, one or more of the three-dimensional substrates described herein and/or have one or more three-dimensional substrates positioned thereon and/or joined thereto, so that the three-dimensional substrate(s) contact(s) the wearer's skin. Other portions of the topsheet (other than the three-dimensional substrates) may also contact the wearer's skin. A typical topsheet is described below, although it will be understood that this topsheet 24, or portions thereof, may be replaced by the three-dimensional substrates described herein. Alternatively, the three-dimensional substrates may be positioned as a strip or a patch on top of the typical topsheet 24, as is described herein.

The topsheet 24 may be the part of the absorbent article that is in contact with the wearer's skin. The topsheet 24 may be joined to the backsheet 25, the core 28 and/or any other layers as is known to those of skill in the art. Usually, the topsheet 24 and the backsheet 25 are joined directly to each other in some locations (e.g., on or close to the periphery of the absorbent article) and are indirectly joined together in other locations by directly joining them to one or more other elements of the article 20.

The topsheet 24 may be compliant, soft-feeling, and non-irritating to the wearer's skin. Further, a portion of, or all of, the topsheet 24 may be liquid permeable, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. If the topsheet 24 includes fibers, the fibers may be spunbond, carded, wet-laid, meltblown, hydroentangled, or otherwise processed as is known in the art. A suitable topsheet comprising a web of spunbond polypropylene (topically treated with a hydrophilic surfactant) is manufactured by Polymer Group, Inc., of Charlotte, N.C. under the designation P-10.

Any portion of the topsheet 24 may be coated with a lotion and/or a skin care composition as is generally disclosed in the art. The topsheet 24 may also comprise or be treated with antibacterial agents, some examples of which are disclosed in PCT Publication WO95/24173. Further, the topsheet 24, the backsheet 25 or any portion of the topsheet or backsheet may be embossed and/or matte finished to provide a more cloth like appearance.

The topsheet 24 may comprise one or more apertures to ease penetration of fluids therethrough. The size of at least the primary apertures is important in achieving the desired fluid encapsulation performance. If the primary apertures are too small, the fluids may not pass through the apertures, either due to poor alignment of the fluid source and the aperture location or due to runny fecal masses, for example, having a diameter greater than the apertures. If the apertures are too large, the area of skin that may be contaminated by "rewet" from the article is increased. Typically, the total area of the apertures at the surface of a diaper may have an area of between about 10 cm$^2$ and about 50 cm$^2$ or between about 15 cm$^2$ and 35 cm$^2$. Examples of apertured topsheets are disclosed in U.S. Pat. No. 6,632,504, assigned to BBA NONWOVENS SIMPSONVILLE. Typical diaper topsheets have a basis weight of from about 10 to about 50 gsm or from about 12 to about 30 gsm, but other basis weights are within the scope of the present disclosure.

Backsheet

The backsheet 25 is generally that portion of the absorbent article 20 positioned adjacent the garment-facing surface of the absorbent core 28 and which prevents, or at least inhibits, the fluids and bodily exudates absorbed and contained therein from soiling articles such as bedsheets and undergarments. The backsheet 25 is typically impermeable, or at least substantially impermeable, to fluids (e.g., urine). The backsheet may, for example, be or comprise a thin plastic film such as a thermoplastic film having a thickness of about 0.012 mm to about 0.051 mm. Example backsheet films include those manufactured by Tredegar Corporation, based in Richmond, Va., and sold under the trade name CPC2 film. Other suitable backsheet materials may include breathable materials which permit vapors to escape from the absorbent article 20 while still preventing, or at least inhibiting, fluids from passing through the backsheet 25. Example breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va., and sold under the designation EXAIRE, and monolithic films such as manufactured by Clopay Corporation, Cincinnati, Ohio under the name HYTREL blend P18-3097.

The backsheet 25 may be joined to the topsheet 24, the absorbent core 28, and/or any other element of the absorbent article 20 by any attachment methods known to those of skill in the art. Suitable attachment methods are described above with respect to methods for joining the topsheet 24 to other elements of the article 20.

An outer cover 23 may cover at least a portion of, or all of, the backsheet 25 to form a soft garment-facing surface of the absorbent article. The outer cover 23 may be formed of one or more nonwoven materials. The outer cover 23 is illustrated in dash in FIG. 2, as an example. The outer cover 23 may be joined to at least a portion of the backsheet 25 through mechanical bonding, adhesive bonding, or other suitable methods of attachment.

Absorbent Core

As used herein, the term "absorbent core" refers to the component of the absorbent article having the most absorbent capacity and comprising an absorbent material and a core wrap or core bag enclosing the absorbent material. The term "absorbent core" does not include the acquisition and/or distribution system or any other components of the article which are not either integral part of the core wrap or core bag or placed within the core wrap or core bag. The absorbent core may comprise, consist essentially of, or consist of, a core wrap, an absorbent material (e.g., superabsorbent polymers) as discussed, and glue.

The absorbent core 28 may comprise an absorbent material with a high amount of superabsorbent polymers (herein abbreviated as "SAP") enclosed within the core wrap. The SAP content may represent 70%-100% or at least 70%, 75%, 80%, 85%, 90%, 95%, 99%, or 100%, by weight of the absorbent material, contained in the core wrap. The core wrap is not considered as absorbent material for the purpose of assessing the percentage of SAP in the absorbent core. The core may also contain airfelt or cellulosic fibers with or without SAP.

By "absorbent material" it is meant a material which has some absorbency property or liquid retaining properties, such as SAP, cellulosic fibers as well as synthetic fibers. Typically, glues used in making absorbent cores have no or little absorbency properties and are not considered as absorbent material. The SAP content may be higher than 80%, for example at least 85%, at least 90%, at least 95%, at least 99%, and even up to and including 100% of the weight of the absorbent material contained within the core wrap. This provides a relatively thin core compared to a conventional core typically comprising between 40-60% SAP and high content of cellulose fibers. The conventional cores are also within the scope of the present disclosure. The absorbent material may in particular comprises less than 15% weight percent or less than 10% weight percent of natural, cellulosic, or synthetic fibers, less than 5% weight percent, less than 3% weight percent, less than 2% weight percent, less than 1% weight percent, or may even be substantially free of natural, cellulosic, and/or synthetic fibers.

Figure 4:
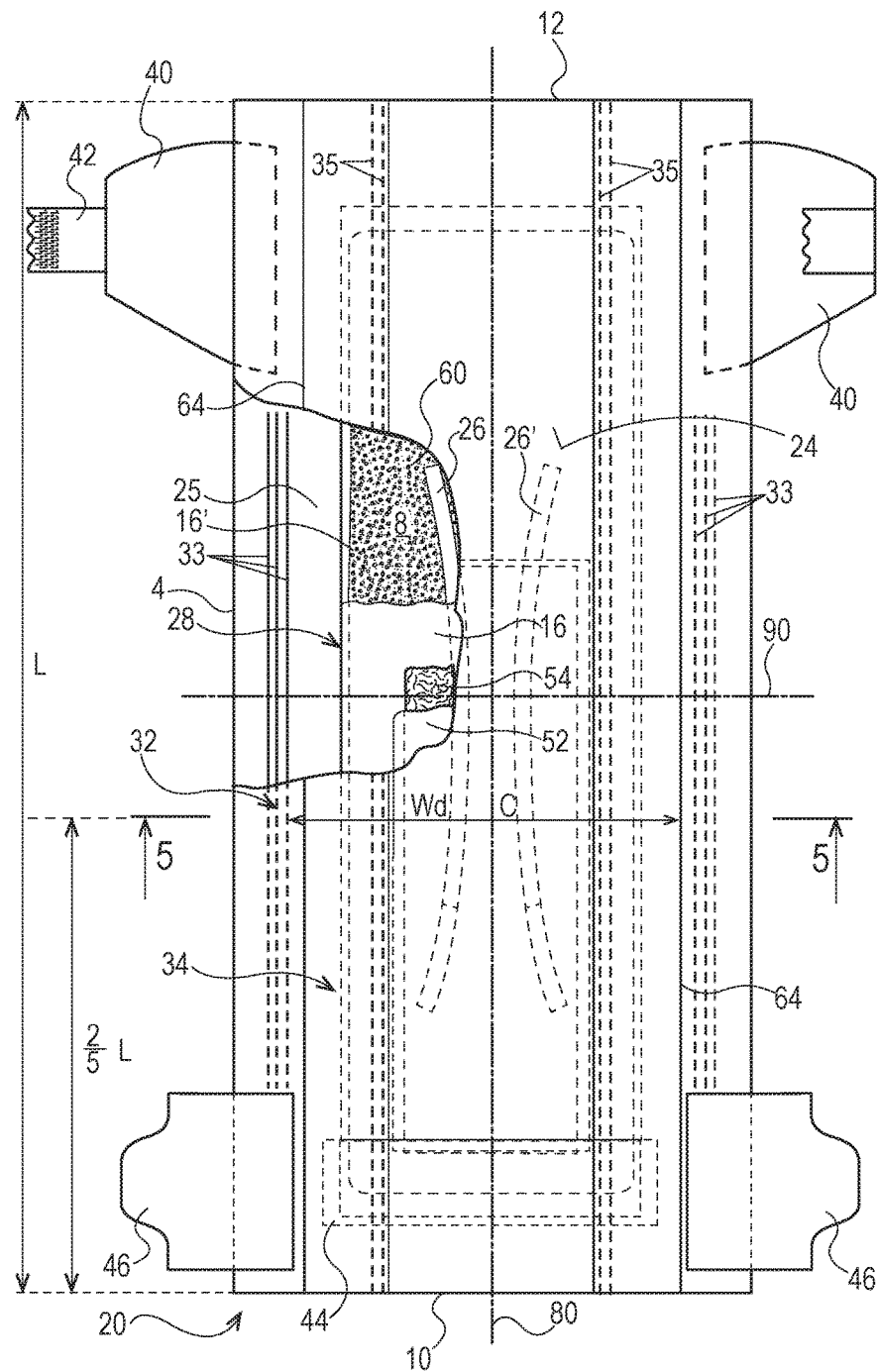
FIG. 4 is a top view of another absorbent article, wearer-facing surface facing the viewer, with some layers partially removed in accordance with the present disclosure.
Figure 5:
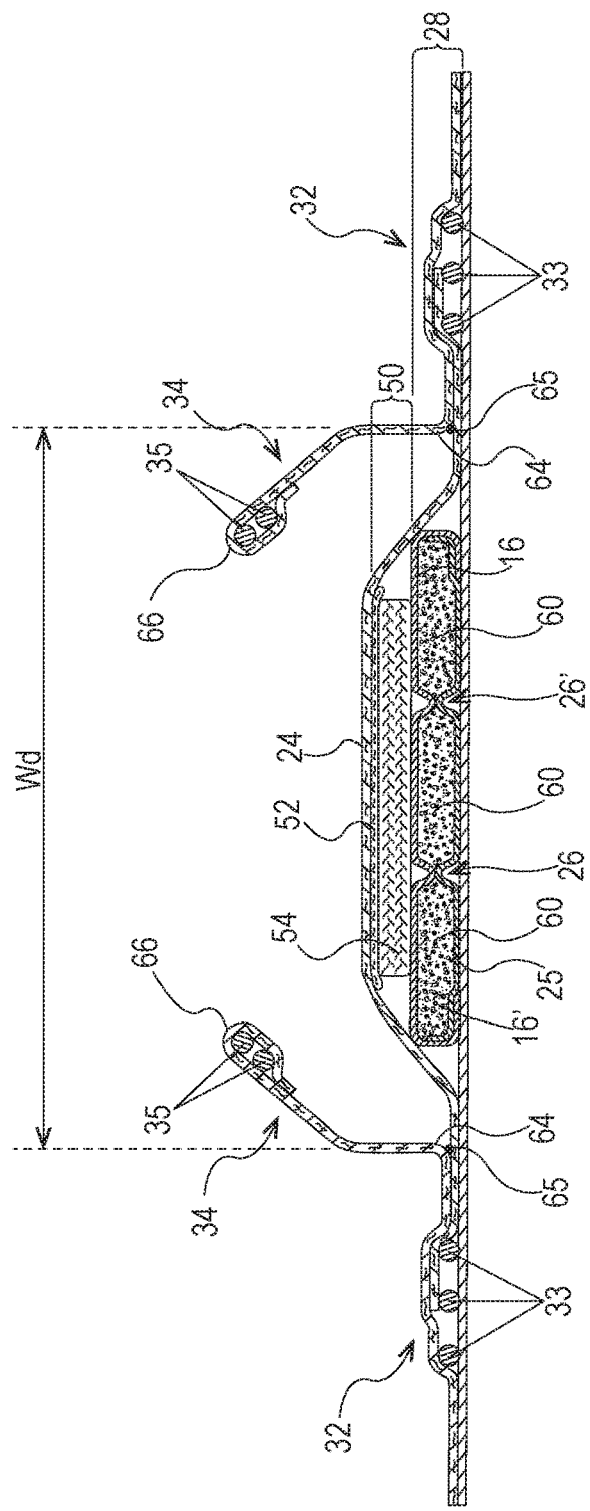
FIG. 5 is a cross-sectional view of the absorbent article taken about line 5-5 of FIG. 4 in accordance with the present disclosure.
Figure 6:
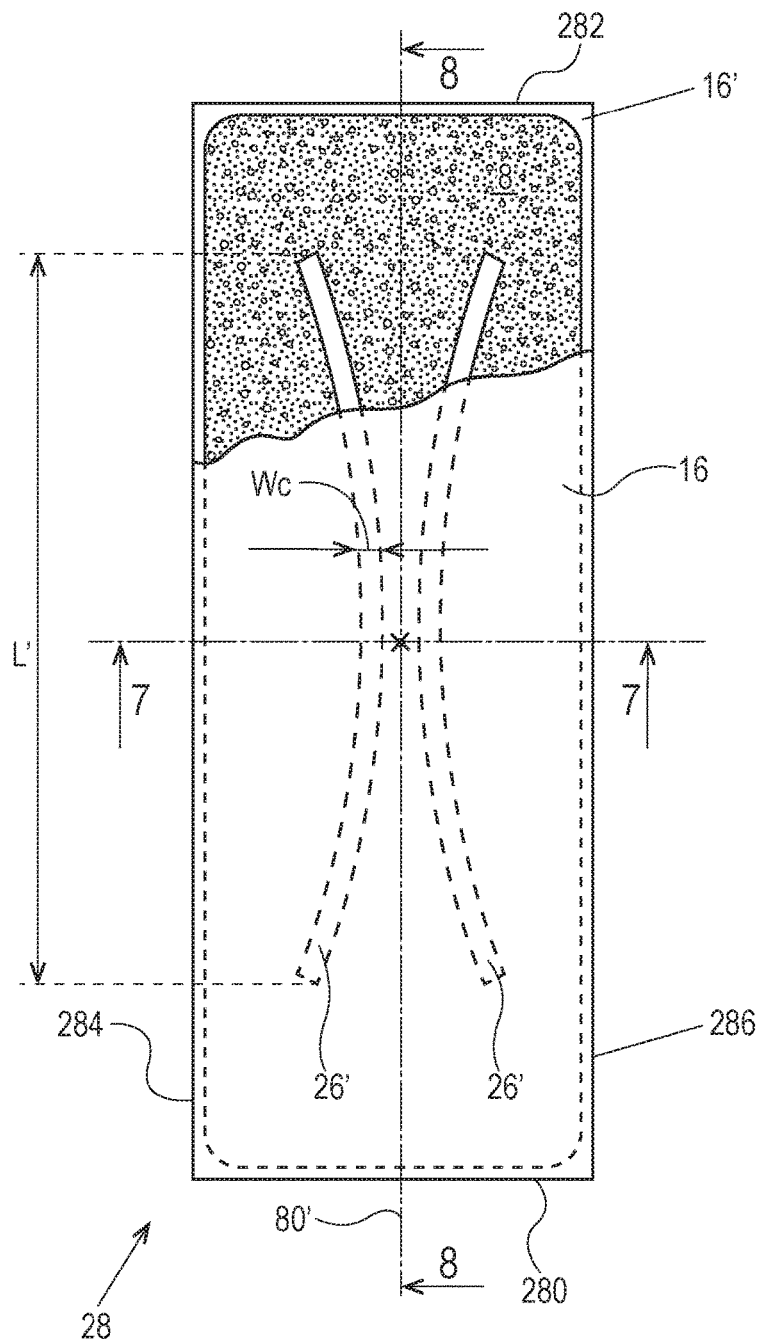
FIG. 6 is a top view of an absorbent core of the absorbent article of FIG. 4 with some layers partially removed in accordance the present disclosure.
Figure 7:
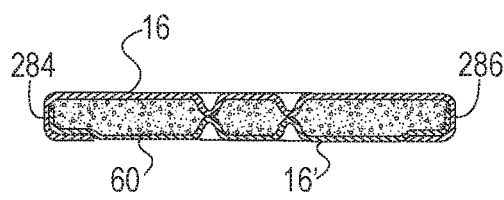
FIG. 7 is a cross-sectional view of the absorbent core taken about line 7-7 of FIG. 6 in accordance with the present disclosure.
Figure 8:
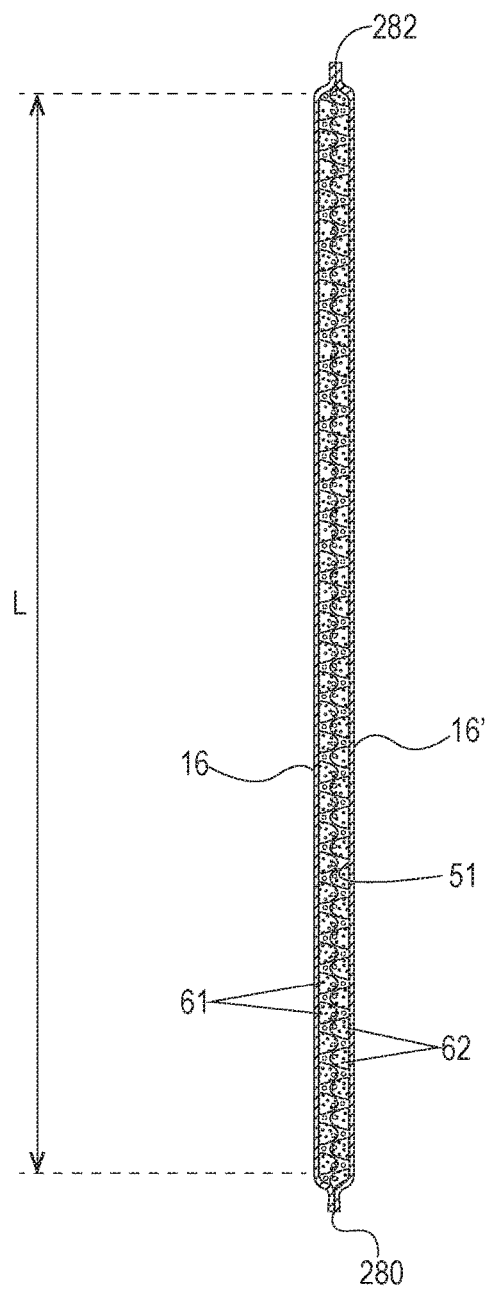
FIG. 8 is a cross-sectional view of the absorbent core taken about line 8-8 of FIG. 6 in accordance with the present disclosure.

The example absorbent core 28 of the absorbent article 20 of FIGS. 4-5 is shown in isolation in FIGS. 6-8. The absorbent core 28 may comprises a front side 280, a rear side 282, and two longitudinal sides 284, 286 joining the front side 280 and the rear side 282. The absorbent core 28 may also comprise a generally planar top side and a generally planar bottom side. The front side 280 of the core is the side of the core intended to be placed towards the front waist edge 10 of the absorbent article. The core 28 may have a longitudinal axis 80' corresponding substantially to the longitudinal axis 80 of the absorbent article 20, as seen from the top in a planar view as in FIG. 1. The absorbent material may be distributed in higher amount towards the front side 280 than towards the rear side 282 as more absorbency may be required at the front in particular absorbent articles. The front and rear sides 280 and 282 of the core may be shorter than the longitudinal sides 284 and 286 of the core. The core wrap may be formed by two nonwoven materials, substrates, laminates, or other materials, 16, 16' which may be at least partially sealed along the sides 284, 286 of the absorbent core 28. The core wrap may be at least partially sealed along its front side 280, rear side 282, and two longitudinal sides 284, 286 so that substantially no absorbent material leaks out of the absorbent core wrap. The first material, substrate, or nonwoven 16 may at least partially surround the second material, substrate, or nonwoven 16' to form the core wrap, as illustrated in FIG. 7. The first material 16 may surround a portion of the second material 16' proximate to the first and second side edges 284 and 286.

The absorbent core may comprise adhesive, for example, to help immobilizing the SAP within the core wrap and/or to ensure integrity of the core wrap, in particular when the core wrap is made of two or more substrates. The adhesive may be a hot melt adhesive, supplied, by H.B. Fuller, for example. The core wrap may extend to a larger area than strictly needed for containing the absorbent material within.

Cores comprising relatively high amount of SAP with various core designs are disclosed in U.S. Pat. No. 5,599,335 (Goldman), EP 1,447,066 (Busam), WO 95/11652 (Tanzer), U.S. Pat. Publ. No. 2008/0312622A1 (Hundorf), and WO 2012/052172 (Van Malderen).

The absorbent material may be a continuous layer present within the core wrap. Alternatively, the absorbent material may be comprised of individual pockets or stripes of absorbent material enclosed within the core wrap. In the first case, the absorbent material may be, for example, obtained by the application of a single continuous layer of absorbent material. The continuous layer of absorbent material, in particular of SAP, may also be obtained by combining two absorbent layers having discontinuous absorbent material application patterns, wherein the resulting layer is substantially continuously distributed across the absorbent particulate polymer material area, as disclosed in U.S. Pat. Appl. Pub. No. 2008/0312622A1 (Hundorf), for example. The absorbent core 28 may comprise a first absorbent layer and a second absorbent layer. The first absorbent layer may comprise the first material 16 and a first layer 61 of absorbent material, which may be 100% or less of SAP. The second absorbent layer may comprise the second material 16' and a second layer 62 of absorbent material, which may also be 100% or less of SAP. The absorbent core 28 may also comprise a fibrous thermoplastic adhesive material 51 at least partially bonding each layer of absorbent material 61, 62 to its respective material 16 or 16'. This is illustrated in FIGS. 7-8, as an example, where the first and second SAP layers have been applied as transversal stripes or "land areas" having the same width as the desired absorbent material deposition area on their respective substrate before being combined. The stripes may comprise different amounts of absorbent material (SAP) to provide a profiled basis weight along the longitudinal axis of the core 80. The first material 16 and the second material 16' may form the core wrap.

The fibrous thermoplastic adhesive material 51 may be at least partially in contact with the absorbent material 61, 62 in the land areas and at least partially in contact with the materials 16 and 16' in the junction areas. This imparts an essentially three-dimensional structure to the fibrous layer of thermoplastic adhesive material 51, which in itself is essentially a two-dimensional structure of relatively small thickness, as compared to the dimension in length and width directions. Thereby, the fibrous thermoplastic adhesive material may provide cavities to cover the absorbent material in the land areas, and thereby immobilizes this absorbent material, which may be 100% or less of SAP.

The thermoplastic adhesive used for the fibrous layer may have elastomeric properties, such that the web formed by the fibers on the SAP layer is able to be stretched as the SAP swell. Elastomeric, hot-melt adhesives of these types are described in more detail in U.S. Pat. No. 4,731,066 issued to Korpman on Mar. 15, 1988. The thermoplastic adhesive material may be applied as fibers.

Superabsorbent Polymer (SAP)

"Superabsorbent polymers" ("SAP"), as used herein, refer to absorbent materials which are cross-linked polymeric materials that can absorb at least 10 times their weight of an aqueous 0.9% saline solution as measured using the Centrifuge Retention Capacity (CRC) test (EDANA method WSP 241.2-05E). The SAP used may have a CRC value of more than 20 g/g, more than 24 g/g, from 20 to 50 g/g, from 20 to 40 g/g, or from 24 to 30 g/g, specifically reciting all 0.1 g/g increments within the above-specified ranges and any ranges created therein or thereby. The SAP useful with the present disclosure may include a variety of water-insoluble, but water-swellable polymers capable of absorbing large quantities of fluids.

The superabsorbent polymer may be in particulate form so as to be flowable in the dry state. Particulate absorbent polymer materials may be made of poly(meth)acrylic acid polymers. However, starch-based particulate absorbent polymer material may also be used, as well as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile.

The SAP may be of numerous shapes. The term "particles" refers to granules, fibers, flakes, spheres, powders, platelets and other shapes and forms known to persons skilled in the art of superabsorbent polymer particles. The SAP particles may be in the shape of fibers, i.e., elongated, acicular superabsorbent polymer particles. The fibers may also be in the form of a long filament that may be woven. SAP may be spherical-like particles. The absorbent core may comprise one or more types of SAP.

For most absorbent articles, liquid discharges from a wearer occur predominately in the front half of the absorbent article, in particular for a diaper. The front half of the article (as defined by the region between the front edge and a transversal line placed at a distance of half L from the front waist edge 10 or rear waist edge 12 may therefore may comprise most of the absorbent capacity of the core. Thus, at least 60% of the SAP, or at least 65%, 70%, 75%, 80%, or 85% of the SAP may be present in the front half of the absorbent article, while the remaining SAP may be disposed in the rear half of the absorbent article. Alternatively, the SAP distribution may be uniform through the core or may have other suitable distributions.

The total amount of SAP present in the absorbent core may also vary according to expected user. Diapers for newborns may require less SAP than infant, child, or adult incontinence diapers. The amount of SAP in the core may be about 5 to 60 g or from 5 to 50 g, specifically reciting all 0.1 increments within the specified ranges and any ranged formed therein or thereby. The average SAP basis weight within the (or "at least one", if several are present) deposition area 8 of the SAP may be at least 50, 100, 200, 300, 400, 500 or more $g/m^2$. The areas of the channels (e.g., 26, 26', 27, 27') present in the absorbent material deposition area 8 are deduced from the absorbent material deposition area to calculate this average basis weight.

Core Wrap

The core wrap may be made of a single substrate, material, or nonwoven folded around the absorbent material, or may comprise two (or more) substrates, materials, or nonwovens which are attached to another. Typical attachments are the so-called C-wrap and/or sandwich wrap. In a C-wrap, as illustrated, for example, in FIGS. 2 and 7, the longitudinal and/or transversal edges of one of the substrates are folded over the other substrate to form flaps. These flaps are then bonded to the external surface of the other substrate, typically by gluing.

The core wrap may be formed by any materials suitable for receiving and containing the absorbent material. Typical substrate materials used in the production of conventional cores may be used, in particular paper, tissues, films, wovens or nonwovens, or laminates or composites of any of these.

The substrates may also be air-permeable (in addition to being liquid or fluid permeable). Films useful herein may therefore comprise micro-pores.

The core wrap may be at least partially sealed along all the sides of the absorbent core so that substantially no absorbent material leaks out of the core. By "substantially no absorbent material" it is meant that less than 5%, less than 2%, less than 1%, or about 0% by weight of absorbent material escape the core wrap. The term "seal" is to be understood in a broad sense. The seal does not need to be continuous along the whole periphery of the core wrap but may be discontinuous along part or the whole of it, such as formed by a series of seal points spaced on a line. A seal may be formed by gluing and/or thermal bonding.

If the core wrap is formed by two substrates 16, 16', four seals may be used to enclose the absorbent material 60 within the core wrap. For example, a first substrate 16 may be placed on one side of the core (the top side as represented in the Figures) and extend around the core's longitudinal edges to at least partially wrap the opposed bottom side of the core. The second substrate 16' may be present between the wrapped flaps of the first substrate 16 and the absorbent material 60. The flaps of the first substrate 16 may be glued to the second substrate 16' to provide a strong seal. This so called C-wrap construction may provide benefits such as improved resistance to bursting in a wet loaded state compared to a sandwich seal. The front side and rear side of the core wrap may then also be sealed by gluing the first substrate and second substrate to another to provide complete encapsulation of the absorbent material across the whole of the periphery of the core. For the front side and rear side of the core, the first and second substrates may extend and may be joined together in a substantially planar direction, forming for these edges a so-called sandwich construction. In the so-called sandwich construction, the first and second substrates may also extend outwardly on all sides of the core and be sealed flat, or substantially flat, along the whole or parts of the periphery of the core typically by gluing and/or heat/pressure bonding. In an example, neither the first nor the second substrates need to be shaped, so that they may be rectangularly cut for ease of production but other shapes are within the scope of the present disclosure.

The core wrap may also be formed by a single substrate which may enclose as in a parcel wrap the absorbent material and be sealed along the front side and rear side of the core and one longitudinal seal.

SAP Deposition Area

The absorbent material deposition area 8 may be defined by the periphery of the layer formed by the absorbent material 60 within the core wrap, as seen from the top side of the absorbent core. The absorbent material deposition area 8 may have various shapes, in particular, a so-called "dog bone" or "hour-glass" shape, which shows a tapering along its width towards the middle or "crotch" region of the core. In this way, the absorbent material deposition area 8 may have a relatively narrow width in an area of the core intended to be placed in the crotch region of the absorbent article, as illustrated in FIG. 1. This may provide better wearing comfort. The absorbent material deposition area 8 may also be generally rectangular, for example as shown in FIGS. 4-6, but other deposition areas, such as a rectangular, "T," "Y," "sand-hour," or "dog-bone" shapes are also within the scope of the present disclosure. The absorbent material may be deposited using any suitable techniques, which may allow relatively precise deposition of SAP at relatively high speed.

Channels

The absorbent material deposition area 8 may comprise at least one channel 26, which is at least partially oriented in the longitudinal direction of the article 80 (i.e., has a longitudinal vector component). Other channels may be at least partially oriented in the lateral direction (i.e., has a lateral vector component) or in any other direction. In the following, the plural form "channels" will be used to mean "at least one channel". The channels may have a length L' projected on the longitudinal axis 80 of the article that is at least 10% of the length L of the article. The channels may be formed in various ways. For example, the channels may be formed by zones within the absorbent material deposition area 8 which may be substantially free of, or free of, absorbent material, in particular SAP. In addition or alternatively, the channel(s) may also be formed by continuously or discontinuously bonding the top side of the core wrap to the bottom side of the core wrap through the absorbent material deposition area 8. The channels may be continuous but it is also envisioned that the channels may be intermittent. The acquisition-distribution system or layer 50, or another layer of the article, may also comprise channels, which may or not correspond to the channels of the absorbent core.

In some instances, the channels may be present at least at the same longitudinal level as the crotch point C or the lateral axis 60 in the absorbent article, as represented in FIG. 1 with the two longitudinally extending channels 26, 26'. The channels may also extend from the crotch region 7 or may be present in the front waist region 5 and/or in the rear waist region 6 of the article.

The absorbent core 28 may also comprise more than two channels, for example, at least 3, at least 4, at least 5, or at least 6 or more. Shorter channels may also be present, for example in the rear waist region 6 or the front waist region 5 of the core as represented by the pair of channels 27, 27' in FIG. 1 towards the front of the article. The channels may comprise one or more pairs of channels symmetrically arranged, or otherwise arranged relative to the longitudinal axis 80.

The channels may be particularly useful in the absorbent core when the absorbent material deposition area is rectangular, as the channels may improve the flexibility of the core to an extent that there is less advantage in using a non-rectangular (shaped) core. Of course channels may also be present in a layer of SAP having a shaped deposition area.

The channels may be completely oriented longitudinally and parallel to the longitudinal axis or completely oriented transversely and parallel to the lateral axis, but also may have at least portions that are curved.

In order to reduce the risk of fluid leakages, the longitudinal main channels may not extend up to any of the edges of the absorbent material deposition area 8, and may therefore be fully encompassed within the absorbent material deposition area 8 of the core. The smallest distance between a channel and the closest edge of the absorbent material deposition area 8 may be at least 5 mm.

The channels may have a width We along at least part of their length which is at least 2 mm, at least 3 mm, at least 4 mm, up to for example 20 mm, 16 mm, or 12 mm, for example. The width of the channel(s) may be constant through substantially the whole length of the channel or may vary along its length. When the channels are formed by absorbent material-free zone within the absorbent material deposition area 8, the width of the channels is considered to be the width of the material free zone, disregarding the possible presence of the core wrap within the channels. If the channels are not formed by absorbent material free zones, for example mainly though bonding of the core wrap through the absorbent material zone, the width of the channels is the width of this bonding.

At least some or all of the channels may be permanent channels, meaning their integrity is at least partially maintained both in the dry state and in the wet state. Permanent channels may be obtained by provision of one or more adhesive materials, for example, the fibrous layer of adhesive material or construction glue that helps adhere a substrate with an absorbent material within the walls of the channel. Permanent channels may also be formed by bonding the upper side and lower side of the core wrap (e.g., the first substrate 16 and the second substrate 16') and/or the topsheet 24 to the backsheet 25 together through the channels. Typically, an adhesive may be used to bond both sides of the core wrap or the topsheet and the backsheet through the channels, but it is possible to bond via other known processes, such as pressure bonding, ultrasonic bonding, heat bonding, or combination thereof. The core wrap or the topsheet 24 and the backsheet 25 may be continuously bonded or intermittently bonded along the channels. The channels may advantageously remain or become visible at least through the topsheet and/or backsheet when the absorbent article is fully loaded with a fluid. This may be obtained by making the channels substantially free of SAP, so they will not swell, and sufficiently large so that they will not close when wet. Furthermore, bonding the core wrap to itself or the topsheet to the backsheet through the channels may be advantageous.

Barrier Leg Cuffs

The absorbent article may comprise a pair of barrier leg cuffs 34. Each barrier leg cuff may be formed by a piece of material which is bonded to the article so it may extend upwards from a wearer-facing surface of the absorbent article and provide improved containment of fluids and other body exudates approximately at the junction of the torso and legs of the wearer. The barrier leg cuffs are delimited by a proximal edge 64 joined directly or indirectly to the topsheet 24 and/or the backsheet 25 and a free terminal edge 66, which is intended to contact and form a seal with the wearer's skin. The barrier leg cuffs 34 extend at least partially between the front waist edge 10 and the rear waist edge 12 of the absorbent article on opposite sides of the longitudinal axis 80 and are at least present at the level of the crotch point (C) or crotch region. The barrier leg cuffs may be joined at the proximal edge 64 with the chassis of the article by a bond 65 which may be made by gluing, fusion bonding, or a combination of other suitable bonding processes. The bond 65 at the proximal edge 64 may be continuous or intermittent. The bond 65 closest to the raised section of the leg cuffs delimits the proximal edge 64 of the standing up section of the leg cuffs.

The barrier leg cuffs may be integral with the topsheet 24 or the backsheet 25 or may be a separate material joined to the article's chassis. Each barrier leg cuff 34 may comprise one, two or more elastic strings 35 close to the free terminal edge 66 to provide a better seal.

In addition to the barrier leg cuffs 34, the article may comprise gasketing cuffs 32, which are joined to the chassis of the absorbent article, in particular to the topsheet 24 and/or the backsheet 25 and are placed externally relative to the barrier leg cuffs. The gasketing cuffs 32 may provide a better seal around the thighs of the wearer. Each gasketing leg cuff may comprise one or more elastic strings or elastic elements 33 in the chassis of the absorbent article between the topsheet 24 and backsheet 25 in the area of the leg openings. All, or a portion of, the barrier leg cuffs and/or gasketing cuffs may be treated with a lotion or another skin care composition.

Acquisition-Distribution System

The absorbent articles of the present disclosure may comprise an acquisition-distribution layer or system 50 ("ADS"). One function of the ADS is to quickly acquire one or more of the fluids and distribute them to the absorbent core in an efficient manner. The ADS may comprise one, two or more layers, which may form a unitary layer or may remain as discrete layers which may be attached to each other. In an example, the ADS may comprise two layers: a distribution layer 54 and an acquisition layer 52 disposed between the absorbent core and the topsheet, but the present disclosure is not so limited.

The ADS may comprise SAP as this may slow the acquisition and distribution of the fluids. Suitable ADS are described in WO 2000/59430 (Daley), WO 95/10996 (Richards), U.S. Pat. No. 5,700,254 (McDowall), and WO 02/067809 (Graef), for example.

In one example, the ADS may not be provided, or only one layer of the ADS may be provided, such as the distribution layer only or the acquisition layer only. When one of the three-dimensional, liquid permeable substrates of the present disclosure is used as a portion of, or all of, a topsheet, or positioned on a topsheet, dryness performance of the liquid permeable substrates may be improved if only one or no layers of the ADS are present. This is owing to the fact that fluids (e.g., urine) are easily able to wick through the liquid permeable substrates directly into the absorbent core 28 and/or into one layer of the ADS.

Distribution Layer

The distribution layer of the ADS may comprise at least 50% by weight of cross-linked cellulose fibers. The cross-linked cellulosic fibers may be crimped, twisted, or curled, or a combination thereof including crimped, twisted, and curled. This type of material is disclosed in U.S. Pat. Publ. No. 2008/0312622 A1 (Hundorf). The cross-linked cellulosic fibers provide higher resilience and therefore higher resistance to the first absorbent layer against the compression in the product packaging or in use conditions, e.g., under wearer weight. This may provide the core with a higher void volume, permeability, and liquid absorption, and hence reduced leakage and improved dryness.

The distribution layer comprising the cross-linked cellulose fibers of the present disclosure may comprise other fibers, but this layer may advantageously comprise at least 50%, or 60%, or 70%, or 80%, or 90%, or even up to 100%, by weight of the layer, of cross-linked cellulose fibers (including the cross-linking agents). Examples of such mixed layer of cross-linked cellulose fibers may comprise about 70% by weight of chemically cross-linked cellulose fibers, about 10% by weight polyester (PET) fibers, and about 20% by weight untreated pulp fibers. In another example, the layer of cross-linked cellulose fibers may comprise about 70% by weight chemically cross-linked cellulose fibers, about 20% by weight lyocell fibers, and about 10% by weight PET fibers. In still another example, the layer may comprise about 68% by weight chemically cross-linked cellulose fibers, about 16% by weight untreated pulp fibers, and about 16% by weight PET fibers. In yet another example, the layer of cross-linked cellulose fibers may comprise from about 90 to about 100% by weight chemically cross-linked cellulose fibers.

Acquisition Layer

The ADS 50 may comprise an acquisition layer 52. The acquisition layer may be disposed between the distribution layer 54 and the topsheet 24. The acquisition layer 52 may be or may comprise a nonwoven material, such as a hydrophilic SMS or SMMS material, comprising a spunbonded, a melt-blown and a further spunbonded layer or alternatively a carded staple fiber chemical-bonded nonwoven. The nonwoven material may be latex bonded.

A further acquisition layer may be used in addition to a first acquisition layer described above. For example, a tissue layer may be placed between the first acquisition layer and the distribution layer. The tissue may have enhanced capillarity distribution properties compared to the acquisition layer described above.

Fastening System

The absorbent article may include a fastening system. The fastening system may be used to provide lateral tensions about the circumference of the absorbent article to hold the absorbent article on the wearer as is typical for taped diapers. This fastening system may not be necessary for training pant articles since the waist region of these articles is already bonded. The fastening system may comprise a fastener such as tape tabs, hook and loop fastening components, interlocking fasteners such as tabs & slots, buckles, buttons, snaps, and/or hermaphroditic fastening components, although any other suitable fastening mechanisms are also within the scope of the present disclosure. A landing zone 44 is normally provided on the garment-facing surface of the front waist region 5 for the fastener to be releasably attached thereto.

Front and Rear Ears

The absorbent article may comprise front ears 46 and rear ears 40. The ears may be an integral part of the chassis, such as formed from the topsheet 24 and/or backsheet 26 as side panels. Alternatively, as represented on FIG. 1, the ears may be separate elements attached by gluing, heat embossing, and/or pressure bonding. The rear ears 40 may be stretchable to facilitate the attachment of the tabs 42 to the landing zone 44 and maintain the taped diapers in place around the wearer's waist. The rear ears 40 may also be elastic or extensible to provide a more comfortable and contouring fit by initially conformably fitting the absorbent article to the wearer and sustaining this fit throughout the time of wear well past when absorbent article has been loaded with fluids or other bodily exudates since the elasticized ears allow the sides of the absorbent article to expand and contract.

Elastic Waist Feature

The absorbent article 20 may also comprise at least one elastic waist feature (not represented) that helps to provide improved fit and containment. The elastic waist feature is generally intended to elastically expand and contract to dynamically fit the wearer's waist. The elastic waist feature may extend at least longitudinally outwardly from at least one waist edge of the absorbent core 28 and generally forms at least a portion of the end edge of the absorbent article. Disposable diapers may be constructed so as to have two elastic waist features, one positioned in the front waist region and one positioned in the rear waist region.

Relations Between the Layers

Typically, adjacent layers and components may be joined together using conventional bonding methods, such as adhesive coating via slot coating or spraying on the whole or part of the surface of the layer, thermo-bonding, pressure bonding, or combinations thereof. This bonding is not represented in the Figures (except for the bonding between the raised element of the leg cuffs 65 with the topsheet 24) for clarity and readability, but bonding between the layers of the article should be considered to be present unless specifically excluded. Adhesives may be used to improve the adhesion of the different layers between the backsheet 25 and the core wrap. The glue may be any suitable hotmelt glue known in the art.

Sanitary Napkin

Figure 9:
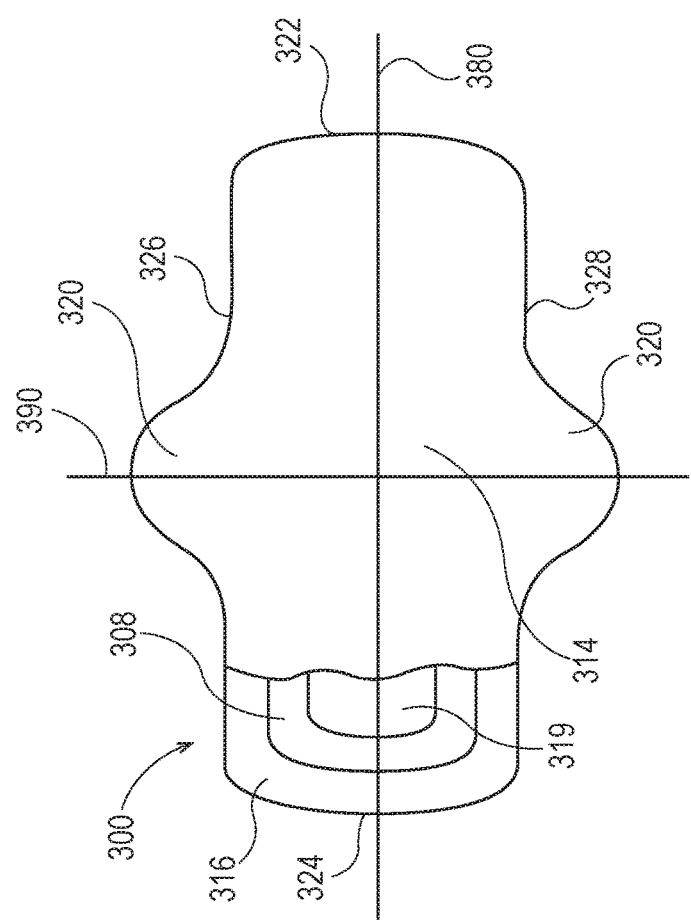
FIG. 9 is a top view of an absorbent article, wearer-facing surface facing the viewer, that is a sanitary napkin with some of the layers cut away in accordance with the present disclosure.

The three-dimensional substrates of the present disclosure may form a portion of a topsheet, form the topsheet, form a portion of, or all of a secondary topsheet, or be positioned on or joined to at least a portion of the topsheet of a sanitary napkin. Referring to FIG. 9, the absorbent article may comprise a sanitary napkin 300. The sanitary napkin 300 may comprise a liquid permeable topsheet 314, a liquid impermeable, or substantially liquid impermeable, backsheet 316, and an absorbent core 308. The absorbent core 308 may have any or all of the features described herein with respect to the absorbent cores 28 and, in some forms, may have a secondary topsheet instead of the acquisition-distribution system disclosed above. The sanitary napkin 300 may also comprise wings 320 extending outwardly with respect to a longitudinal axis 380 of the sanitary napkin 300. The sanitary napkin 300 may also comprise a lateral axis 390. The wings 320 may be joined to the topsheet 314, the backsheet 316, and/or the absorbent core 308. The sanitary napkin 300 may also comprise a front edge 322, a rear edge 324 longitudinally opposing the front edge 322, a first side edge 326, and a second side edge 328 longitudinally opposing the first side edge 326. The longitudinal axis 380 may extend from a midpoint of the front edge 322 to a midpoint of the rear edge 324. The lateral axis 390 may extend from a midpoint of the first side edge 326 to a midpoint of the second side edge 328. The sanitary napkin 300 may also be provided with additional features commonly found in sanitary napkins as is generally known in the art, such as a secondary topsheet 319, for example.

Three-Dimensional Substrates

The three-dimensional, liquid permeable substrates of the present disclosure may comprise substrates that have first elements (e.g., projections) that have a first z-directional height and at least second elements (e.g., land areas) that have a second z-directional height. The substrates may also have a plurality of apertures. The substrates may also have at least third elements having at least a third z-directional height. Owing to such structures, fluids may be quickly moved away from the skin of a wearer, leaving primarily the first elements having the first z-directional heights contacting the skin of the wearer, thereby making the wearer feel dryer. The fluids may flow via gravity or via capillary gradient into the second elements having the second z-directional heights and/or into and through the apertures, so that the fluids may be absorbed into the absorbent articles. By providing the three-dimensional substrates of the present disclosure, fluid/skin contact and the time that fluids are in contact with the skin of a wearer may be reduced. Further, the first elements having the first z-directional heights may act as a spacer between the fluids and the skin of the wearer while the fluids are being absorbed into the absorbent article.

Figure 10:
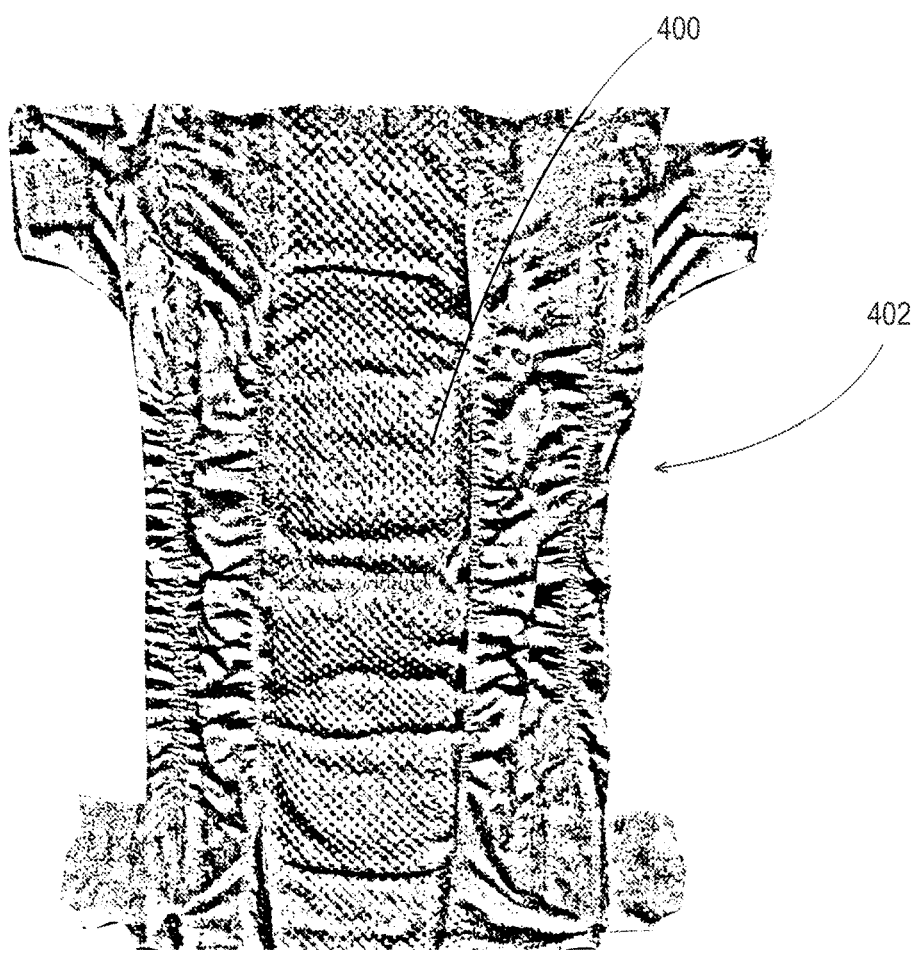
FIG. 10 is a top view of an absorbent article, wearer-facing surface facing the viewer, that comprises a three-dimensional, liquid permeable substrate in accordance with the present disclosure.
Figure 11:
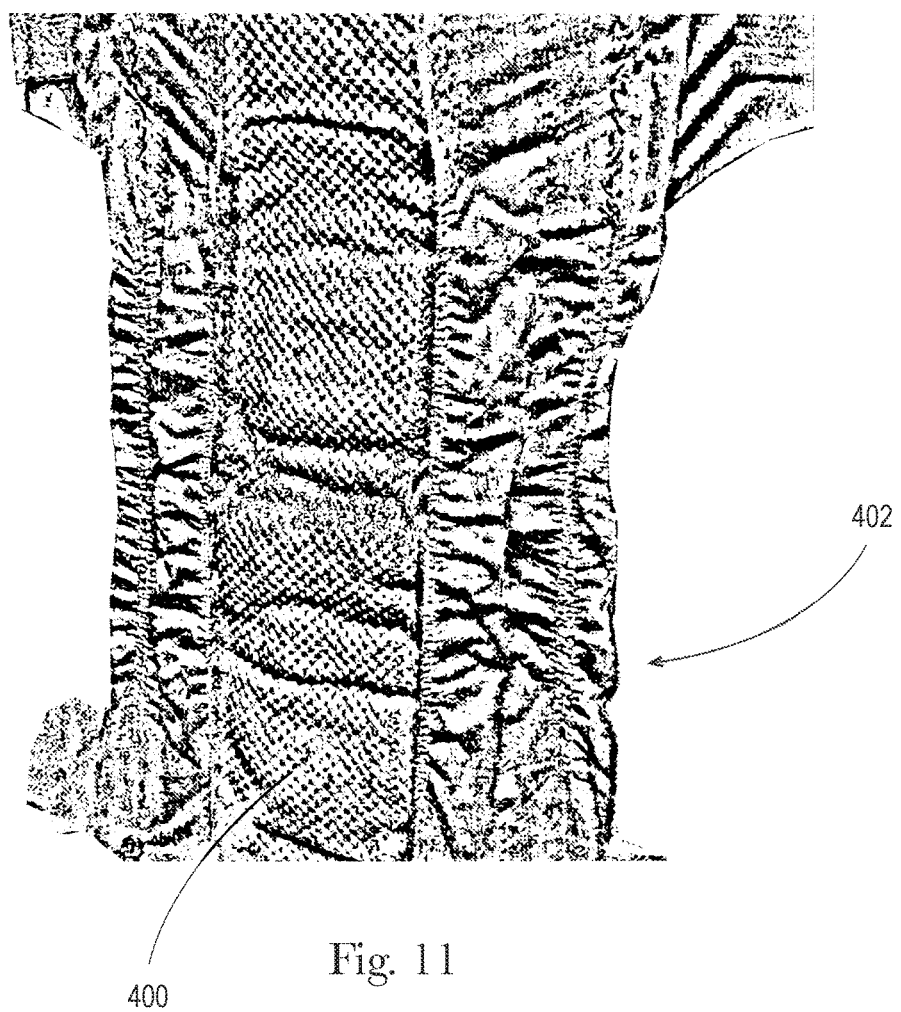
FIG. 11 is a perspective view of an absorbent article of FIG. 10 in accordance with the present disclosure.
Figure 12:
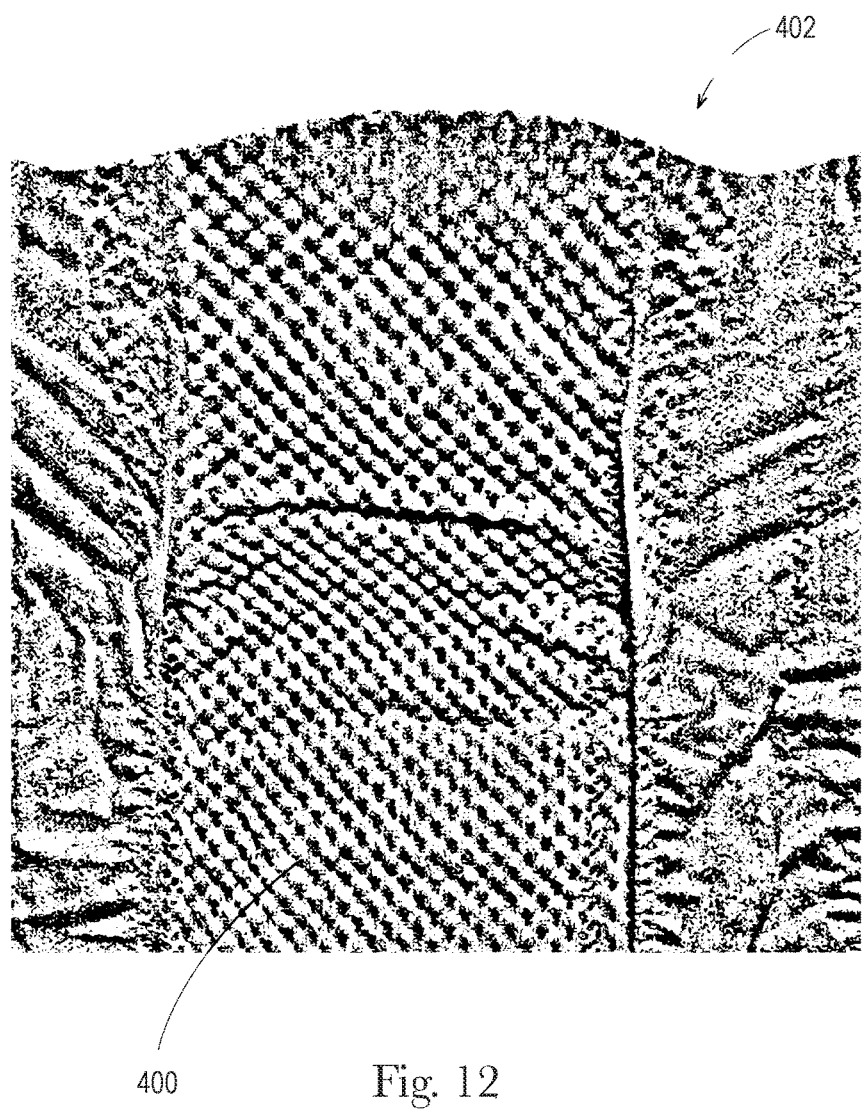
FIG. 12 is an enlarged top view of a portion of the liquid permeable substrate of FIG. 10 in accordance with the present disclosure.
Figure 13:
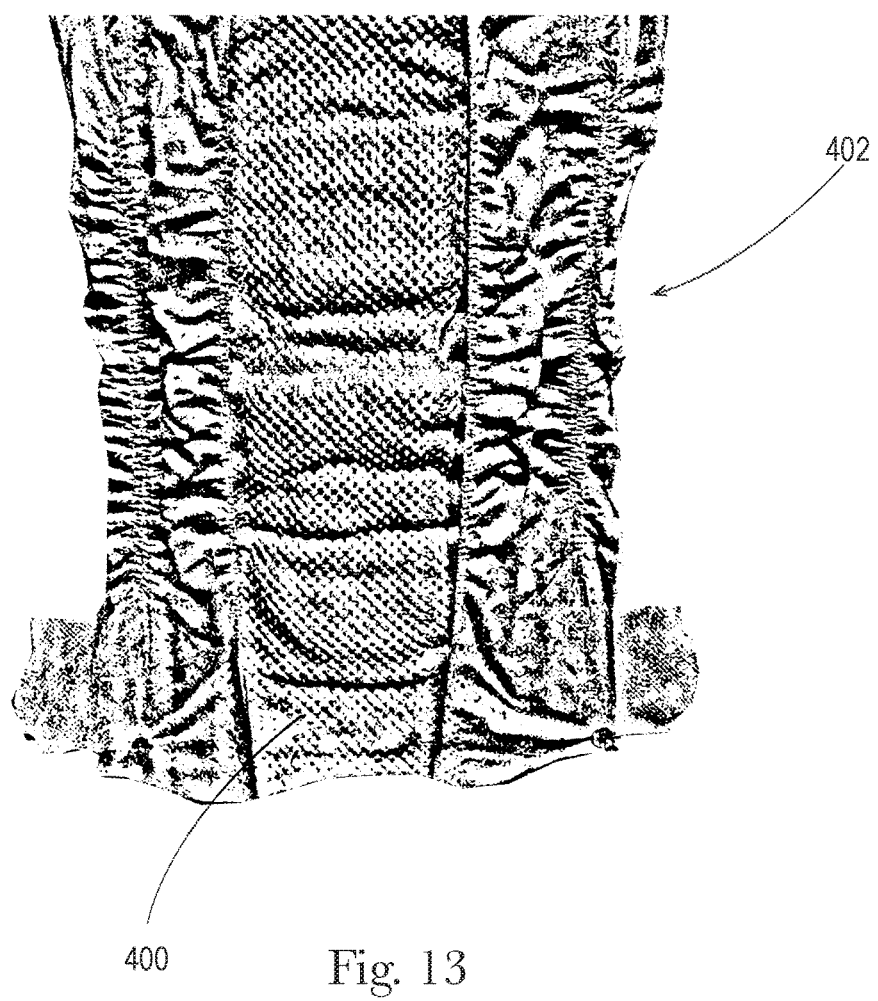
FIG. 13 is another enlarged top view of a portion of the liquid permeable substrate of FIG. 10 in accordance with the present disclosure.

Referring to FIGS. 10-13, a three-dimensional, liquid permeable substrate 400 (referred to herein both as a three-dimensional substrate or a liquid permeable substrate) is illustrated an on absorbent article 402. FIG. 10 is a top view of the absorbent article 402 with the wearer-facing surface facing the viewer. FIG. 11 is a perspective view of the absorbent article 402 with the wearer-facing surface facing the viewer. FIG. 12 is a top view of a portion of the liquid preamble substrate 400 on the absorbent article with the wearer-facing surface facing the viewer. FIG. 13 is another top view of a portion of the liquid permeable substrate 400 on the absorbent article 402 with the wearer-facing surface facing the viewer.

In one form, the liquid permeable substrate 400, or other liquid permeable substrates described herein, may comprise a patch or strip positioned on and/or joined to a topsheet of the absorbent article 402. The patch or strip may be bonded to the topsheet, adhesively attached to the topsheet, cold-pressure welded to the topsheet, ultrasonically bonded to the topsheet, and/or otherwise joined to the topsheet. Alternatively, the liquid permeable substrates of the present disclosure may comprise the topsheet (e.g., topsheet 24), form all of the topsheet, or form a portion of the topsheet. Also, the topsheet 24 may be comprised only of one or more of the liquid permeable substrates of the present disclosure. In any of the various configurations, the liquid permeable substrates of the present disclosure are intended to form at least a portion of the wearer-facing surface of an absorbent article and be in at least partial contact with the skin of a wearer.

Figure 14:
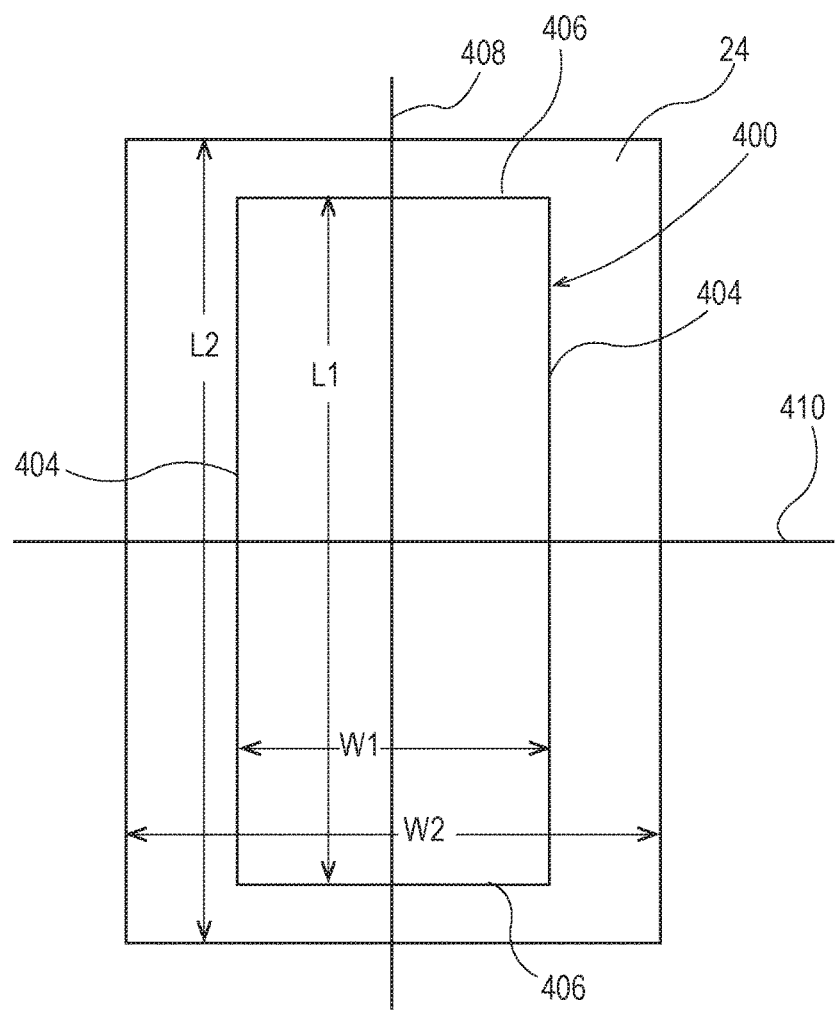
FIG. 14 is a schematic illustration of a three-dimensional, liquid permeable substrate positioned on and/or joined to a topsheet for an absorbent article in accordance with the present disclosure.
Figure 15:
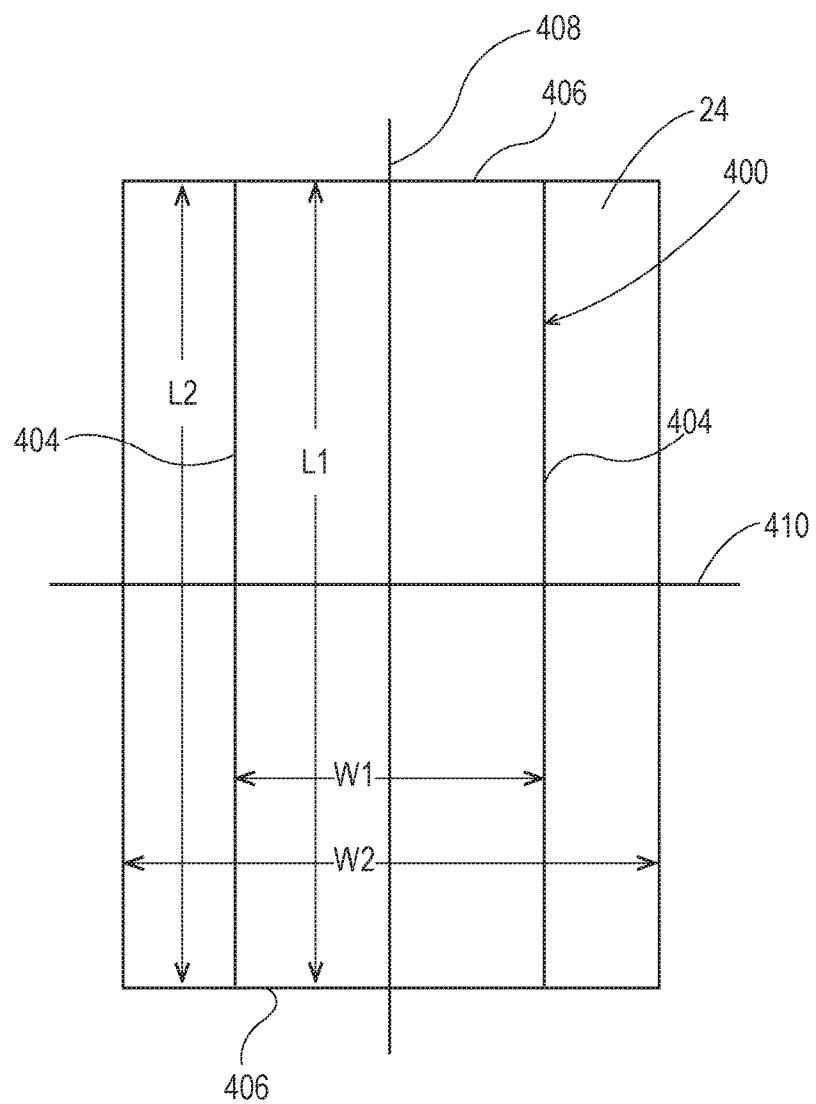
FIG. 15 is another schematic illustration of a three-dimensional, liquid permeable substrate positioned on and/ or joined to a topsheet for an absorbent article in accordance with the present disclosure.
Figure 16:
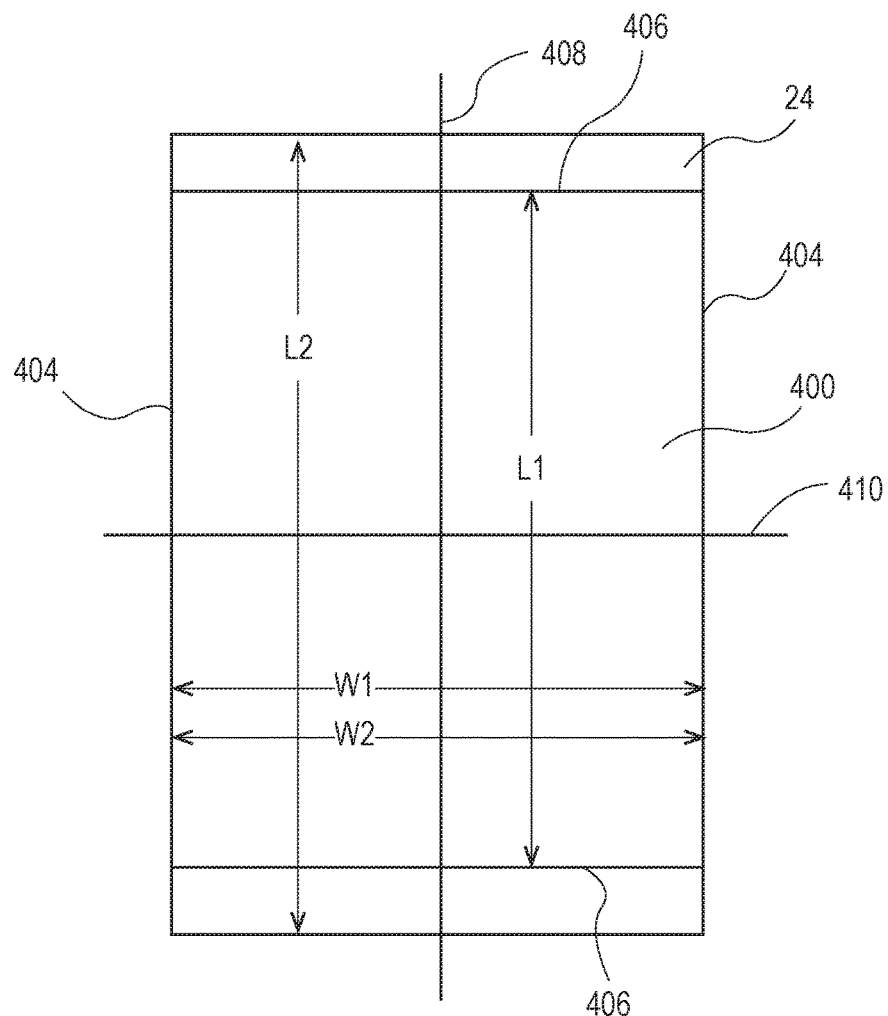
FIG. 16 is another schematic illustration of a three-dimensional, liquid permeable substrate positioned on and/ or joined to a topsheet for an absorbent article in accordance with the present disclosure.

Referring to FIGS. 14-16, the liquid permeable substrate 400, or other liquid permeable substrates described herein, in a patch or strip form joined to the topsheet 24, may have a cross machine directional width of W1, while the topsheet 24 may have a cross machine directional width of W2. W1 may be less than, the same as, substantially the same as, or greater than (not illustrated) the width W2. The width W1 may also vary or be constant throughout a longitudinal length of the liquid permeable substrates. Still referring to FIGS. 14-16, the liquid permeable substrate 400, or other liquid permeable substrates described herein, in a patch or strip form, may have a machine directional length of L1, while the topsheet 24 may have a machine directional length of L2. L1 may be less than, the same as, substantially the same as, or greater than (not illustrated) the length L2. The length L1 may vary or be constant across the width W1 of the liquid permeable substrates. Although not illustrated in FIGS. 14-16, the lengths and widths of the topsheet 24 and the liquid permeable substrates may be the same, or substantially the same.

Although the patch or strip of the liquid permeable substrate 400 is illustrated as being rectangular in FIGS. 14-16, the liquid permeable substrates of the present disclosure may also have any other suitable shapes, such a front/back profiled shape (i.e., wider in the front, wider in the back, and/or narrower in the crotch), a square shape, an ovate shape, or other suitable shape. The side edges 404 and/or the end edge 406 of the liquid permeable substrate 400 may have one or more arcuate portions, designs, and/or shapes cut out from them to provide an aesthetically pleasing look to the liquid permeable substrate 400. One side edge 404 may be symmetrical or asymmetrical to another side edge 404 about a longitudinal axis, 408, of the topsheet 24. Likewise, one end edge 406 may be symmetrical or asymmetrical to another side edge 406 about a lateral axis, 410 of the topsheet 24.

The liquid permeable substrate 400 may comprise one or more layers. If more than one layer is provided, the layers may be joined together or attached to each other through mechanical bonding, adhesive bonding, pressure bonding, heat bonding, passing heated air through both layers, or by other methods of joining to form the multilayer substrate 400. Alternatively the layers are formed in subsequent fiber laydown steps such as a first and a second carding operation for a first type and a second type of staple fibers or two subsequent beams of spunlaying polymeric filaments including additives. The first layer may comprise one or more hydrophobic materials, or may be fully hydrophobic, and the second layer may comprise one or more hydrophilic materials, or may be fully hydrophilic. Instead of one layer comprising a hydrophobic material and the other layer comprising a hydrophilic material, one layer may comprise a material that is more hydrophobic or more hydrophilic than the material that comprises the other layer (e.g., both layers are hydrophilic, but one layer is more hydrophilic or both layers are hydrophobic, but one layer is more hydrophobic). The first layer may comprise a hydrophobic layer and the second layer may comprise a hydrophilic layer or vice versa. The first layer may be used as a portion of, or all of, the wearer-facing surface of the absorbent article. Alternatively, the second layer may be used as a portion of, or all of, the wearer-facing surface of the absorbent article.

The rationale for having the first layer (or wearer-facing layer) being comprised of a hydrophobic material is twofold. First, if the liquid permeable substrate is apertured, the hydrophobic layer will not retain as much liquid as the hydrophilic second layer and thus, there will be less fluid (e.g., urine) in direct contact with the skin of a wearer. Second, projections (described below) in the first and second layers generally form hollow portions or arches on a garment-facing side of the liquid permeable substrate that do not have direct contact with the ADS or core, so fluids can get caught in the hollow arches. Without good connectivity of the hollow arches to the ADS or the core, the liquid permeable substrate may retain more fluid and feel wetter to the wearer. With a hydrophobic first layer, however, any liquid that is wicked into the hollow arches will be mostly on the garment-facing, or downward-facing hydrophilic side of the liquid permeable substrate, thereby leaving the first hydrophobic layer dryer. In principle, this may be achieved with a hydrophilic or capillary gradient from the first layer to the second layer (e.g. finer fibers in the second layer with same hydrophilic properties (i.e., contact angle with the liquid)). The apertures in the substrate may play an important role to enable initial and fast fluid flow (strike-through) despite the first hydrophobic layer. Therefore, the first hydrophobic layer works in concert with the protrusions, hollow arches, and the apertures to reduce wetness on the wearer-facing surface of the liquid permeable substrate. In other instances, the second layer may be used as a portion of the wearer-facing surface.

The first layer may comprise a plurality of first fibers and/or filaments (hereafter together referred to as fibers). The plurality of first fibers may comprise fibers that are the same, substantially the same, or different in size, shape, composition, denier, fiber diameter, fiber length, and/or weight. The second layer may comprise a plurality of second fibers. The plurality of second fibers may comprise fibers that are the same, substantially the same, or different in size, shape, composition, denier, fiber diameter, fiber length, and/or weight. The plurality of first fibers may be the same as, substantially the same as, or different than the plurality of second fibers. Additional layers may have the same or different configurations.

The first layer and/or the second layer may comprise bicomponent fibers having a sheath and a core. The sheath may comprise polyethylene and the core may comprise polyethylene terephthalate (PET). The sheath and the core may also comprise any other suitable materials known to those of skill in the art. The sheath and the core may each comprise about 50% of the fibers by weight of the fibers, although other variations (e.g., sheath 60%, core 40%; sheath 30%, core 70% etc.) are also within the scope of the present disclosure. The bicomponent fibers or other fibers that make up the first and/or second layers may have a denier in the range of about 0.5 to about 4, about 1.0 to about 3, about 1.5 to about 2.5, or about 2, specifically including all 0.1 denier increments within the specified ranges and all ranges formed therein or thereby. Denier is defined as the mass in grams per 9000 meters of a fiber length.

The plurality of first and second fibers may also comprise any other suitable types of fibers, such as polypropylene fibers, other polyolefins, other polyesters besides PET such as polylactic acid, thermoplastic starch-containing sustainable resins, other sustainable resins, bio-PE, bio-PP, and Bio-PET, viscose fibers, rayon fibers, or other suitable nonwoven fibers, for example. These fibers may have any suitable deniers or denier ranges and/or fiber lengths or fiber length ranges. In an instance where the plurality of first and second fibers are the same or substantially the same, the plurality of second fibers may be treated with a hydrophilic agent, such as a surfactant, to cause the plurality of second fibers to become hydrophilic or at least less hydrophobic. The plurality of first fibers may not be treated with the surfactant such that they remain in their natural hydrophobic state or the plurality of first fibers may be treated with a surfactant to become less hydrophobic.

The first layer may have a basis weight in the range of about 10 gsm to about 25 gsm. The second layer may have a basis weight in the range of about 10 gsm to about 45 gsm. The basis weight of the substrate (both first and second layers) may be in the range of about 20 gsm to about 70 gsm, about 20 gsm to about 60 gsm, about 25 gsm to about 50 gsm, about 30 gsm to about 40 gsm, about 30 gsm, about 35 gsm, or about 40 gsm.

In an example, the basis weight of the substrate may be about 30 gsm to about 40 gsm or about 35 gsm. In such an example, the first layer may have a basis weight in the range of about 10 gsm to about 20 gsm, or about 15 gsm, and the second layer may have a basis weight in the range of about 15 gsm to about 25 gsm, or about 20 gsm. In another example, the basis weight of the substrate may be about 20 gsm. In such an example, the first layer may have a basis weight of about 10 gsm and the second layer may have a basis weight of about 10 gsm. In still another example, the basis weight of the substrate may be about 60 gsm. In such an example, the first layer may have a basis weight of about 24 gsm, and the second layer may have a basis weight of 36 gsm. All other suitable basis weight ranges for the first and second layers and the substrates are within the scope of the present disclosure. Accordingly, the basis weight of the layers and the substrates may be designed for specific product requirements.

Specifically recited herein are all 0.1 gsm increments within the above-specified ranges of basis weight and all ranges formed therein or thereby.

The liquid permeable substrates of the present disclosure may also form a portion of, or all of, the outer cover 23 which is joined to at least a portion of the backsheet 25. In other instances, the outer cover 23 may comprise a pattern (e.g., embossed pattern, printed pattern) and/or three-dimensional structure that is the same as, or similar in appearance to, the liquid permeable substrates of the present disclosure. In general, the appearance of at least a portion of a liquid permeable substrate on the wearer-facing surface may match, or substantially match, at least a portion of the outer cover 23 or another portion of absorbent article.

Figure 25:
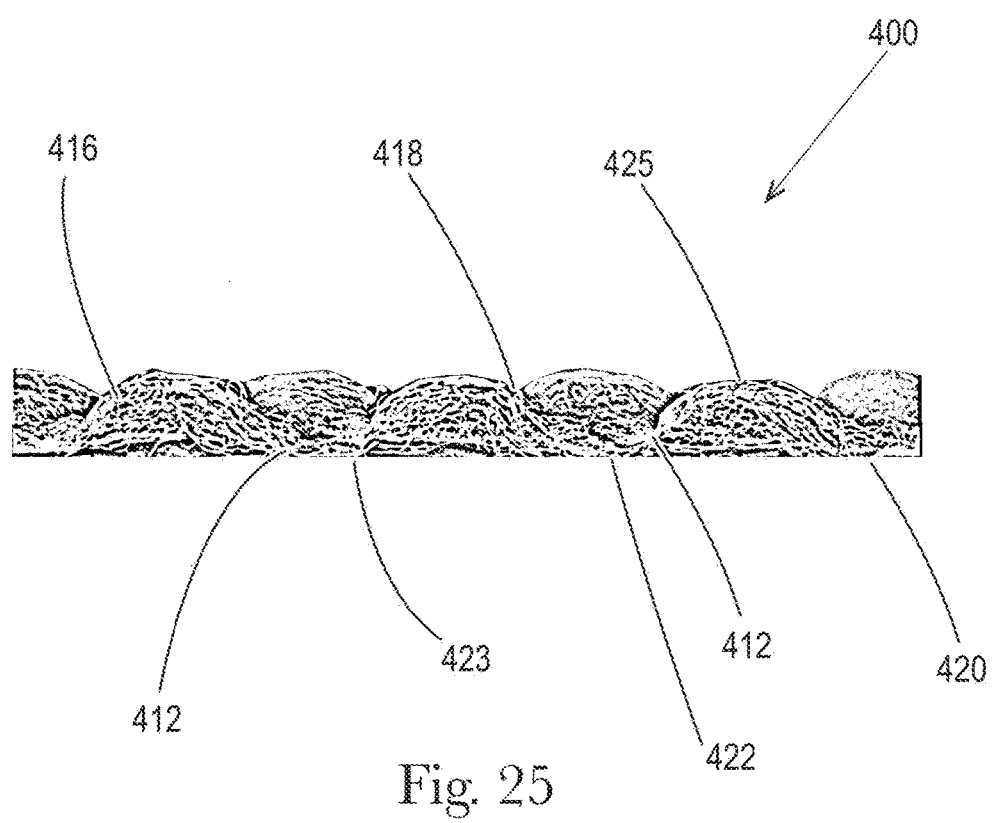
FIG. 25 is a cross sectional view of the liquid permeable substrate in accordance with the present disclosure.

FIG. 17 is a front view of a portion of a three-dimensional, liquid permeable substrate, wearer-facing surface facing the viewer. FIG. 18 is a front perspective view of the portion of the three-dimensional, liquid permeable substrate of FIG. 17. FIG. 19 is another front view of a portion of a three-dimensional, liquid permeable substrate, wearer-facing surface facing the viewer. FIG. 20 is a front perspective view of the portion of the liquid permeable substrate of FIG. 19. FIG. 21 is a back view of a portion of a three-dimensional, liquid permeable substrate, wearer-facing surface facing the viewer. FIG. 22 is a back perspective view of the portion of the three-dimensional, liquid permeable substrate of FIG. 21. FIG. 23 is another back view of a portion of a three-dimensional, liquid permeable substrate, wearer-facing surface facing the viewer. FIG. 24 is a back perspective view of the portion of the liquid permeable substrate of FIG. 23. FIG. 25 is a cross-sectional view of the liquid permeable substrate.

Referring generally to FIGS. 17-25, the liquid permeable substrate 400 may comprise a first layer and a second layer, or more than two layers or one layer. The substrate 400 may comprise a plurality of land areas 412, a plurality of recesses 414, and a plurality of projections 416. The plurality of projections 416 may form the first elements having the first z-directional height, and the land areas 412 may form the second elements having the second z-direction height, as described above. The plurality of land areas 412, the plurality of recesses 414, and the plurality of projections 416 may together form a first three-dimensional surface on a first side 418 of the substrate 400. The plurality of land areas 412, the plurality of recesses 414, and the plurality of projections 416 may also form a second three-dimensional surface on a second side 420 of the substrate 400. The projections 416 may be generally dome shaped on a wearer-facing surface of the liquid permeable substrate 400 and may be hollow arch-shaped on the garment-facing surface of the substrate 400. All of, or a majority of (i.e., more than 50% of, or more than 75% of), or substantially all of, the recesses 414 may define an aperture 422 therein at a location most distal from a top peak 425 of an adjacent projection 416. A perimeter 423 of a majority of, or all of, the apertures 422 may form a bottommost portion or plane of the substrate 400, while the top peak 425 (i.e., uppermost portion) of a majority of, or all of, the projections 416 may form a topmost portion or plane of the substrate 400. In other instances, the substrate may not have apertures within the recesses 414 and the portion of the recesses 414 most distal from the top peaks 425 of the projections 416 may form the bottommost portion or plane of the substrate 400. The apertures 422 may extend through the first and the second layers of the substrate 400.

The land areas 412 may be positioned intermediate: (1) adjacent projections 416, (2) adjacent recesses 414 and/or adjacent apertures 422. The land areas 412 may also surround at least a portion of, or all of, a majority of, or all of, the recesses 414 and/or the apertures and at least a majority of, or all of, the projections 416. The land areas 412 may be positioned between a plane of a perimeter of at least a majority of the apertures 422 and a plane of at least a majority of the top peaks 425 of the projections 416.

The projections 416 may alternate with the recesses 414 and/or the apertures 422 in a direction generally parallel with a lateral axis 424 of the liquid permeable substrate 400. The lateral axis 424 is generally parallel with the lateral axis 410 illustrated in FIGS. 14-16. The projections 416 may also alternate with the recesses 414 and/or apertures 422 in a direction generally parallel with a longitudinal axis 426 of the liquid permeable substrate 400. The longitudinal axis 426 is generally parallel with the longitudinal axis 408 illustrated in FIGS. 14-16. In such a configuration, in a direction generally parallel with the lateral axis 424 or in a direction generally parallel with the longitudinal axis 426, the projections 416 and the recesses 414 and/or apertures 422 alternate (i.e., projection, recess and/or apertures, projection, recess and/or aperture). This feature provides better softness to the substrate 400 in that there is a soft projection peak 425 intermediate most of, or all of, adjacent recesses 414 and/or apertures 422. This feature also helps maintain the skin of a wearer away from fluids in the land areas 412 and/or the recesses 414, since the projections 416 essentially create a spacer between the skin and the fluids.

Two or more adjacent projections 416 may be separated from each other by a recess 414 and/or an aperture 422 and one or more land areas 412 in a direction generally parallel to the lateral axis 424 or in a direction generally parallel to the longitudinal axis 426. Two or more adjacent recesses 414 and/or apertures 422 may be separated by a projection 416 and one or more land areas 412 in a direction generally parallel to the lateral axis 424 or in a direction generally parallel to the longitudinal axis 426. The land areas 412 may fully surround the apertures 422 and the projections 416. The land areas 412 may together form a generally continuous grid through the substrate 400, while the projections 416 and the recesses 414 and/or the apertures 422 may be discrete elements throughout the substrate.

In some instances, two or more, such as four projections 416 may be positioned around at least a majority of, substantially all of, or all of, the recesses 414 and/or the apertures 422 (this does not include the land areas 412 intermediate the projections 416 and the recesses 414 and/or the apertures 422). Two or more recesses 414 and/or apertures 422, such as four, may be positioned around at least a majority of, substantially all of, or all of, the projections 416 (this does not include the land areas 412 intermediate the recesses 414 and/or the apertures 422 and the projections 416). The projections 416, recesses 414, apertures 422, and land areas 422 may all be formed of portions of the first and second layers of the substrate. If more than two layers are provided in a substrate, the projections 416, recesses 414, apertures 422, and land areas 422 may all be formed of portions of the first, second and third layers of the substrate. The same may be true if more than three layers are provided in a particular substrate. In other instances, the land areas 422 may only be formed in the first layer.

The apertures 422 and/or the recesses 414 may comprise a first set of apertures and/or recesses 414 together forming a first line in the substrate 400 and a second set of apertures 422 and/or recesses 414 together forming a second line in the substrate 400. The first line may be generally parallel with or generally perpendicular to the second line. The first line may also form an acute or obtuse angle with the second line. The projections 416 may comprise a first set of projections 416 together forming a first line in the substrate 400 and a second set of projections 416 together forming a second line in the substrate 400. The first line may be generally parallel with or generally perpendicular to the second line. The first line may also form an acute or obtuse angle with the second line.

The substrate 400 may be generally symmetrical about the lateral axis 424 and/or generally symmetrical about the longitudinal axis 426. In other instances, the substrate may not be symmetrical about the lateral axis 424 and/or the longitudinal axis 426.

In one form, the substrate 400 may comprise a first line comprising alternating apertures 422 and projections 416 extending in a direction parallel to the lateral axis 424 and a second adjacent line comprising alternating apertures 422 and projections 416 extending in the direction generally parallel to the lateral axis 424. The lines will run through the center of the apertures 422 and the projections 416. See for, example, FIG. 17, lines A and B. If a line, C, is drawn in a direction generally parallel to the longitudinal axis 426 and that intersects lines A and B, an aperture 422 will be located at the intersection of lines A and C and a projection 416 will be located at the intersection of the lines B and C. The same is true if lines A and B are drawn in a direction parallel to the longitudinal axis 426 and line C is draw in a direction generally parallel to the lateral axis 424, as illustrated in FIG. 18. If the lines are drawn at different locations, the intersection of lines A and C may have a projection 416 and the intersection of lines B and C may have an aperture 422. The main point being that the rows of apertures and the rows of projections are staggered. By staggering the apertures and projections in this fashion, better softness is achieved in the wearer-facing surface of the substrate 400 owing to a soft projection or projection crest being intermediate two apertures.

Parameters of the Three-Dimensional Substrates

All or a majority of the projections 416 may have a z-directional height in the range of about 300 µm to about 6000 µm, about 500 µm to about 5000 µm, about 500 µm to about 4000 µm, about 300 µm to about 3000 µm, about 500 µm to about 3000 µm, about 500 µm to about 2000 µm, about 750 µm to about 1500 µm, about 800 µm to about 1400 µm, about 900 µm to about 1300 µm, about 1000 µm to about 1300 µm, about 1100 µm to about 1200 µm, about 1165, about 1166, about 1167, or about 1150 µm to about 1200 µm, specifically reciting all 1 µm increments within the above-specified ranges and all ranges formed therein or thereby.

The z-directional height of the projections 416 are measured according to the Projection Height Test described herein.

All or a majority of the recesses 414 may have a z-directional height in the range of about 200 µm to about 3000 µm, about 300 µm to about 2000 µm, about 100 µm to about 2000 µm, about 500 µm to about 2000 µm, about 500 µm to about 1500 µm, about 700 µm to about 1300 µm, about 800 µm to about 1200 µm, about 900 µm to about 1100 µm, about 900 µm to about 1000 µm, about 970 µm, or about 950 µm to about 1000 µm, specifically reciting all 1 µm increments within the above-specified ranges and all ranges formed therein or thereby. The z-directional height of the recesses 416 are measured according to the Recess Height Test described herein.

The substrate, 400, or portions thereof, may have an overall z-directional height in the range of about 500 µm to about 6000 µm, about 750 µm to about 4000 µm, about 1000 µm to about 6000 µm, about 1500 µm to about 6000 µm, about 1000 µm to about 3000 µm, about 1500 µm to about 2500 µm, about 1750 µm to about 2300 µm, about 1900 µm to about 2300 µm, about 2000 µm to about 2300 µm, about 2100 µm to about 2250 µm, about 2136 µm, or about 2135 µm, specifically reciting all 1 µm increments within the above-specified ranges and all ranges formed therein or thereby. The overall z-directional height of the substrate 400, or portions thereof, is measured according to the Overall Substrate Height Test described herein.

A majority of, or all of, the apertures 422 may have an effective aperture area in the range of about 0.4 $mm^2$ to about 10 $mm^2$, about 0.5 $mm^2$ to about 8 $mm^2$, about 0.5 $mm^2$ to about 3 $mm^2$, about 0.5 $mm^2$ to about 4 $mm^2$, about 0.5 $mm^2$ to about 5 $mm^2$, about 0.7 $mm^2$ to about 6 $mm^2$, about 0.7 $mm^2$ to about 3 $mm^2$, about 0.8 $mm^2$ to about 2 $mm^2$, about 0.9 $mm^2$ to about 1.4 $mm^2$, about 1 $mm^2$, about 1.1 $mm^2$, about 1.2 $mm^2$, about 1.23 $mm^2$, about 1.3 $mm^2$, or about 1.4 $mm^2$, specifically reciting all 0.1 $mm^2$ increments within the above-specified ranges and all ranges formed therein or thereby. The effective aperture area of the apertures is measured according to the Aperture Test described herein.

A majority of, or all of, the apertures 422 may have a feret (length of aperture) in the range of about 0.5 mm to about 4 mm, about 0.8 mm to about 3 mm, about 1 mm to about 2 mm, about 1.2 mm to about 1.8 mm, about 1.4 mm to about 1.6 mm, about 1.49, or about 1.5 mm specifically reciting all 0.1 mm increments within the above-specified ranges and all ranges formed therein or thereby. The aperture feret is measured according to the Aperture Test described herein.

A majority of, or all of, the apertures 422 may have a minimum feret (width of aperture) in the range of about 0.5 mm to about 4 mm, about 0.7 mm to about 3 mm, about 0.8 mm to about 2 mm, about 0.9 mm to about 1.3 mm, about 1 mm to about 1.2 mm, about 1 mm, about 1.1 mm, about 1.11 mm, about 1.2 mm, or about 1.3 mm, specifically reciting all 0.1 mm increments within the above-specified ranges and all ranges formed therein or thereby. The aperture minimum feret is measured according to the Aperture Test described herein.

A majority of, or all of, the apertures 422 may have a feret to minimum feret ratio in the range of about 0.3 to about 2.5, about 0.5 to about 2, about 0.8 to about 1.6, about 1 to about 1.5, about 1.1 to about 1.5, about 1.2 to about 1.3, about 1.35, about 1.4, or about 1.5, specifically reciting all 0.1 increments within the above-specified ranges and all ranges formed therein or thereby. The feret ratio is calculated by dividing the aperture feret by the aperture minimum feret.

The average lateral axis center-to-center aperture spacing of a majority of, or all of, adjacent apertures, measuring across a projection, is in the range of about 2 mm to about 20 mm, about 2 mm to about 15 mm, about 3 mm to about 12 mm, about 3 mm to about 10 mm, about 3 mm to about 8 mm, about 3 mm to about 7 mm, about 4 mm to about 6 mm, about 5 mm to about 6 mm, about 4 mm, about 4.8 mm, about 4.9 mm, about 5.0 mm, about 5.1 mm, about 5.2 mm, about 5.3 mm, about 5.4 mm, about 5.5 mm, about 5.6 mm, about 5.7 mm, about 5.8 mm, or about 5.9 mm, about 6 mm, about 7 mm, about 8 mm, about 9 mm, or about 10 mm, specifically reciting all 0.1 mm increments within the above-specified ranges and all ranges formed therein or thereby. The average lateral axis center-to-center spacing of adjacent apertures is measured according to the Average Aperture Spacing Test (Lateral Axis Aperture Spacing) described herein.

The average longitudinal axis center-to-center aperture spacing of a majority of, or all of, adjacent apertures, measuring across a projection, is in the range of about 2 mm to about 20 mm, about 2 mm to about 15 mm, about 3 mm to about 12 mm, about 3 mm to about 10 mm, about 3 mm to about 8 mm, about 3 mm to about 7 mm, about 4 mm to about 6 mm, about 5 mm to about 6 mm, about 4 mm, about 4.8 mm, about 4.9 mm, about 5.0 mm, about 5.1 mm, about 5.2 mm, about 5.3 mm, about 5.4 mm, about 5.5 mm, about 5.6 mm, about 5.7 mm, about 5.8 mm, or about 5.9 mm, about 6 mm, about 7 mm, about 8 mm, about 9 mm, or about 10 mm, specifically reciting all 0.1 mm increments within the above-specified ranges and all ranges formed therein or thereby. The average longitudinal axis center-to-center spacing of adjacent apertures is measured according to the Average Aperture Spacing Test (Longitudinal Axis Aperture Spacing) described herein.

A majority of, or all of, the projections 416 may have a widest cross-sectional diameter, taken in a direction parallel to the lateral axis of the absorbent article, in the range of about 1, to about 15 mm, about 1 mm to about 10 mm, about 1 mm to about 8 mm, about 1 mm to about 6 mm, about 1.5 mm to about 6 mm, about 2 mm to about 5 mm, specifically reciting all 0.1 mm increments within the above-specified ranges and all ranges formed therein or thereby.

A majority of, or all of, the projections 416 may have a widest cross-sectional diameter, taken in a direction parallel to the longitudinal axis of the absorbent article, in the range of about 1 mm to about 15 mm, about 1 mm to about 10 mm, about 1 mm to about 8 mm, about 1 mm to about 6 mm, about 1.5 mm to about 6 mm, about 2 mm to about 5 mm, specifically reciting all 0.1 mm increments within the above-specified ranges and all ranges formed therein or thereby.

The substrates of the present disclosure may have a % effective open area in the range of about 1% to about 50%, about 1% to about 40%, about 3% to about 35%, about 5% to about 25%, about 5% to about 20%, about 6% to about 18%, about 5% to about 15%, about 5%, about 8%, about 9%, about 9.5%, about 10%, about 10.5%, about 11%, or about 12%, specifically reciting all 0.1% increments within the above-specified ranges and all ranges formed therein or thereby. The % effective open area of the substrates is measured according to the Aperture Test described herein.

The substrates of the present disclosure may have apertures having a perimeter in the range of about 1 mm to about 50 mm, about 1 mm to about 30 mm, about 2 mm to about 20 mm, about 2 mm to about 15 mm, about 2 mm to about 10 mm, about 3 mm to about 8 mm, about 4 mm, about 5 mm, about 5.42 mm, about 6 mm, or about 7 mm, specifically reciting all 0.1 mm increments within the above-specified ranges and all ranges formed therein or thereby. The perimeter of the apertures is measured according to the Aperture Test described herein.

The first side 418 of the substrates 400 of the present disclosure may have geometric roughness value in the range of about 2 to about 4.5, about 2.5 to about 4, about 3 to about 4, about 3.1 to about 3.5, about 3.2, about 3.3, about 3.31, about 3.35, about 3.4, or about 3.5, specifically reciting all 0.1 increments within the above-specified ranges and all ranges formed therein or thereby. The geometric roughness values of the first side 418 of the substrates 400 of the present disclosure are measured according to the Descriptive Analysis Roughness Test described herein. The first side 418 of the substrates 400 of the present disclosure may have a coefficient of friction value in the range of about 0.2 to about 0.4, about 0.25 to about 0.35, about 0.27 to about 0.31, about 0.27, about 0.28, about 0.29, about 0.30, or about 0.31, specifically reciting all 0.01 increments within the above-specified ranges and all ranges formed therein or thereby. The coefficient of friction values of the first side 418 of the substrates 400 of the present disclosure are measured according to the Descriptive Analysis Roughness Test described herein. The first side 418 of the substrates 400 of the present disclosure may have a slip stick value in the range of about 0.010 to about 0.025, about 0.015 to about 0.020, about 0.015, about 0.016, about 0.017, about 0.018, or about 0.019, specifically reciting all 0.001 increments within the above-specified ranges and all ranges formed therein or thereby. The coefficient of friction values of the first side 418 of the substrates 400 of the present disclosure are measured according to the Descriptive Analysis Roughness Test described herein.

The second side 420 of the substrates 400 of the present disclosure may have geometric roughness value in the range of about 2 to about 4.0, about 2.3 to about 3.5, about 2.5 to about 3.3, about 2.6 to about 3.1, about 2.6, about 2.7, about 2.8, about 2.83, about 2.9, or about 3.0, specifically reciting all 0.1 increments within the above-specified ranges and all ranges formed therein or thereby. The geometric roughness values of the second side 420 of the substrates 400 of the present disclosure are measured according to the Descriptive Analysis Roughness Test described herein. The second side 420 of the substrates 400 of the present disclosure may have a coefficient of friction value in the range of about 0.2 to about 0.4, about 0.25 to about 0.35, about 0.27 to about 0.31, about 0.27, about 0.28, about 0.29, about 0.30, or about 0.31, specifically reciting all 0.01 increments within the above-specified ranges and all ranges formed therein or thereby. The coefficient of friction values of the second side 420 of the substrates 400 of the present disclosure are measured according to the Descriptive Analysis Roughness Test described herein. The second side 420 of the substrates 400 of the present disclosure may have a slip stick value in the range of about 0.010 to about 0.025, about 0.011 to about 0.018, about 0.012, about 0.013, about 0.014, about 0.015, or about 0.016, specifically reciting all 0.001 increments within the above-specified ranges and all ranges formed therein or thereby. The coefficient of friction values of the second side 420 of the substrates 400 of the present disclosure are measured according to the Descriptive Analysis Roughness Test described herein.

Ratios

The ratio of the height of the projections (μm) to the % effective open area may be in the range of about 70 to about 160, about 80 to about 150, about 100 to about 145, about 95 to about 150, about 100 to about 140, about 110 to about 130, about 115 to about 130, about 118 to about 125, about 120, about 121, about 122, about 122.74, about 123, or about 124, specifically reciting all 0.1 increments within the specified ranges and all ranges formed therein or thereby.

The ratio of the overall substrate height (μm) to the % effective open area may be in the range of about 125 to about 350, about 150 to about 300, about 175 to about 275, about 200 to about 250, about 215 to about 235, about 220 to about 230, or about 225, specifically reciting all 0.1 increments within the specified ranges and all ranges formed therein or thereby.

The ratio of the height of the projections (μm) to the geometric roughness of a surface (e.g., first or second; 418 or 420) of the three-dimensional substrates may be in the range of about 250 to about 600, about 300 to about 500, about 325 to about 450, about 325 to about 425, about 350, about 352, about 410, or about 412, specifically reciting all 0.1 increments within the specified ranges and all ranges formed therein or thereby.

The ratio of the overall substrate height (μm) to the geometric roughness of a surface (e.g., first or second; 418 or 420) of the three-dimensional substrates may be in the range of about 500 to about 900, about 600 to about 800, about 645, about 650, about 700, about 750 m, or about 755, specifically reciting all 0.1 increments within the specified ranges and all ranges formed therein or thereby.

The substrates of the present disclosure may comprise one or more colors, dyes, inks, indicias, patterns, embossments, and/or graphics. The colors, dyes, inks, indicias, patterns, and/or graphics may aid the aesthetic appearance of the substrates.

The substrates of the present disclosure may be used as a portion of, or all of, any suitable products, such as dusters, wipes (wet or dry), makeup removal substrates, paper towels, toilet tissue, facial tissue, medical gowns, surgical substrates, wraps, filtration substrates, or any other suitable products.

Method of Making the Three-Dimensional Substrates or Absorbent Articles Comprising the Three-Dimensional Substrates The three-dimensional substrates and absorbent articles comprising three-dimensional substrates of the present disclosure may be made by any suitable methods known in the art. In particular, the articles may be hand-made or industrially produced at high speed.

Figure 26:
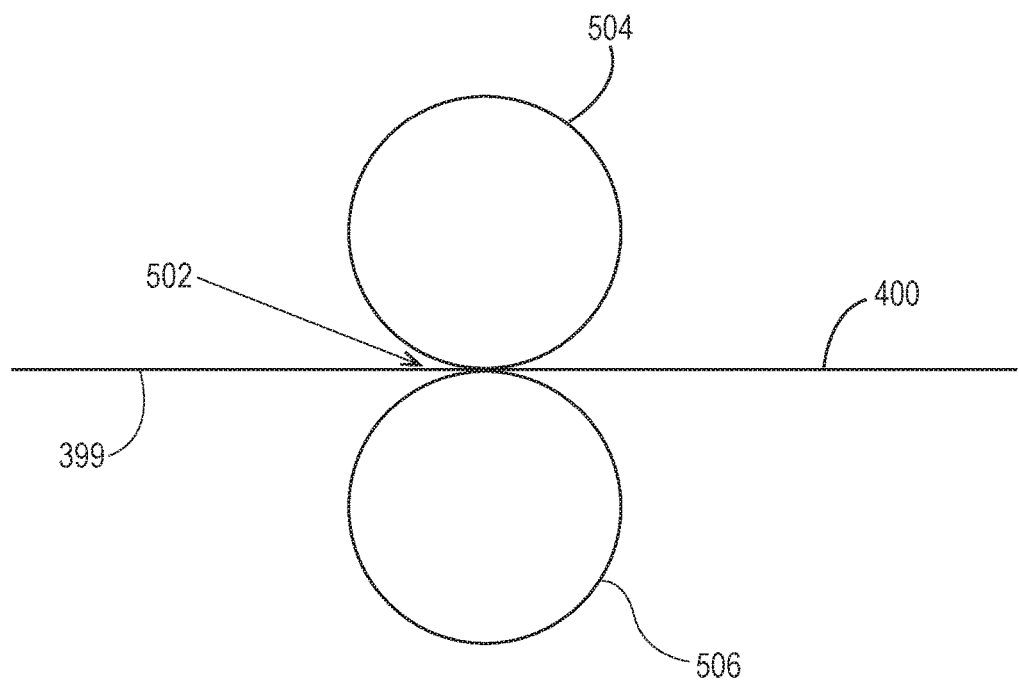
FIG. 26 is a schematic illustration of one example process for forming the substrates of the present disclosure.
Figure 27:
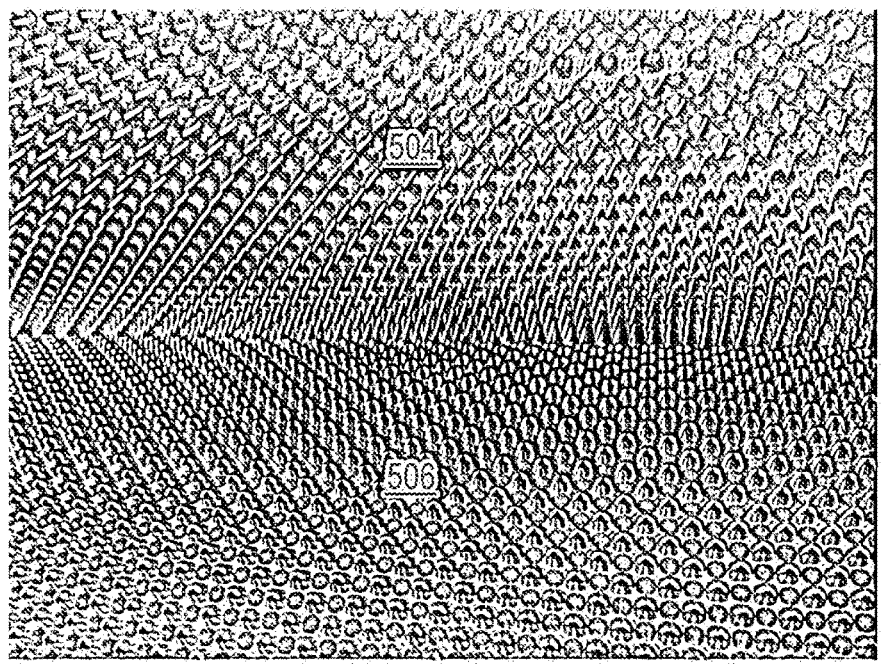
FIG. 27 is a view of intermeshing engagement of portions of first and second rolls in accordance with the present disclosure.
Figure 28:
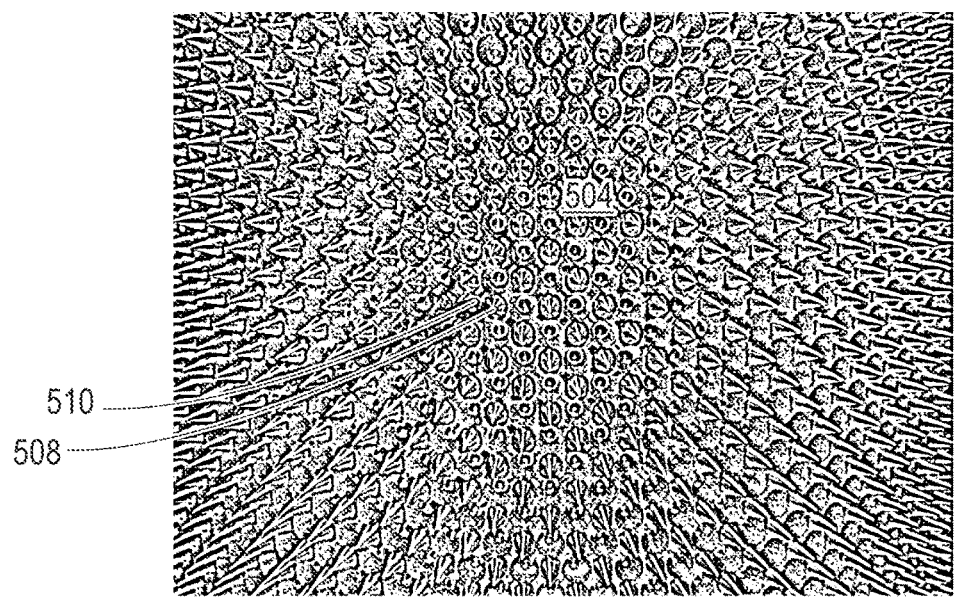
FIG. 28 is a view of a portion of the first roll in accordance with the present disclosure.
Figure 29:
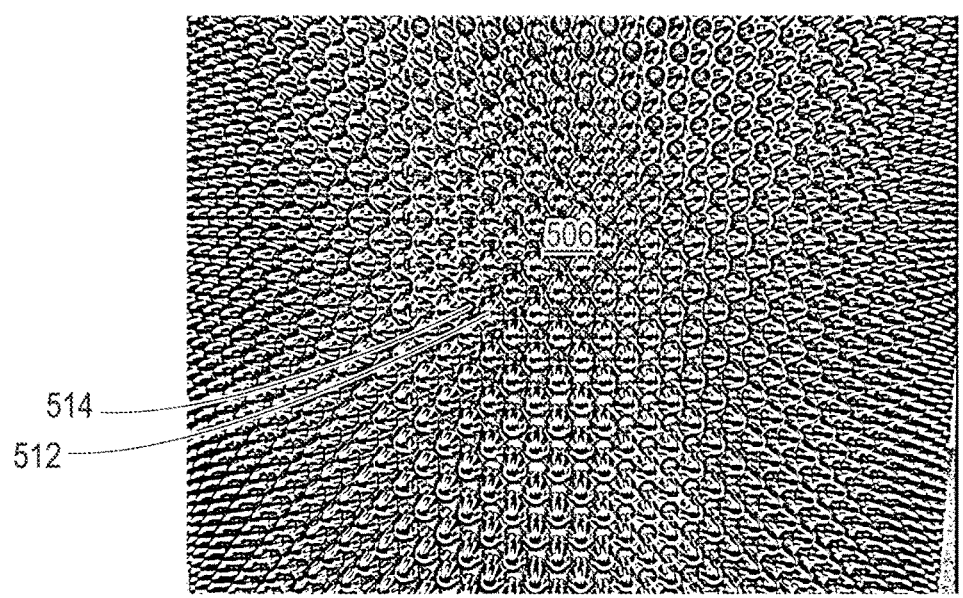
FIG. 29 is a view of a portion of the second roll in accordance with the present disclosure.

FIG. 26 is a schematic illustration of one example process for forming the substrates of the present disclosure. FIG. 27 is a view of intermeshing engagement of portions of first and second rolls. FIG. 28 is a view of a portion of the first roll. FIG. 29 is a view of a portion of the second roll.

Referring to FIGS. 26-29, the substrates of the present disclosure may be formed by passing a one or more layer substrate 399 (non-three dimensional) through a nip 502 formed by two intermeshing rolls 504 and 506 to form a three-dimensional substrate 400. The rolls 504 and 506 may be heated. A first roll 504 may create the apertures 422 and the recesses 414 in the substrate 400 (in combination with the second roll) and a second roll 506 may create the projections 416 in the substrate 400 (in combination with the first roll). The first roll 504 may comprise a plurality of conically-shaped protrusions 508 extending radially outwardly from the first roll 504. The first roll 504 may also comprise a plurality of recesses 510 formed in a radial outer surface of the first roll 504. The second roll 506 may comprise a plurality of dome-shaped protrusions 512 extending radially outwardly from the second roll 506. The second roll 506 may also comprise a plurality of recesses 514 formed in the radial outer surface of the second roll 506.

The protrusions 508 on the first roll 504 may have a different size, shape, height, area, width and/or dimension than the protrusions 512 on the second roll 506. The recesses 510 formed in the first roll 504 may have a different size, shape, height, area, width, and/or dimension than the recesses 514 formed in the second roll 506. The recesses 510 in the first roll 504 may be configured to at least partially receive the dome-shaped protrusions 512, thereby creating the projections 414 in the substrate 400. The recesses 510 may be deep enough so that the portions of the substrate forming the projections 414 and projection peaks 425 will not be compressed, or sufficiently compressed. Specifically as the dome-shaped protrusions 512 engage into the recesses 510, there is sufficient depth left in the space between the metal surfaces in a radial direction so that the thickness of the substrate in the projections is higher than the thickness of the recesses. This feature provides projections 414 with a softer feel and a greater height compared to compressing the portions of the substrate forming the projections. The recesses 514 in the second roll 506 may be configured to at least partially receive the conically-shaped protrusions 508 thereby creating the recesses 414 and the apertures 422 in the substrate 400.

The substrates of the present disclosure may also be formed by any other suitable methods known to those of skill in the art.

Multi-Component Topsheets Employing the Three-Dimensional Substrates

The three-dimensional substrates detailed herein may be more expensive than traditional topsheet materials. Accordingly, when employing any variation of the three-dimensional substrates detailed herein in an absorbent article, a multi-component topsheet application, as described below, may be utilized. Such multi-component topsheets may comprise one or more of the variations of the three-dimensional substrates detailed herein, as well as traditional topsheet materials.

FIGS. 30-37 depict top and cross-sectional schematic illustrations of embodiments of a multi-component topsheet. The multi-component topsheet 600 may include a first discrete substrate 610, a second discrete substrate 620, and a third discrete substrate 630. The multi-component topsheet 600 has a longitudinal axis 601 that runs the longer overall dimension of the topsheet (in this case, the MD or machine direction), and a lateral axis 602 that runs perpendicular to the longitudinal axis. The multi-component topsheet 600 may have an overall outer perimeter defined by first longitudinal edge 603, second longitudinal edge 604, first lateral edge 605, and second lateral edge 606. The first discrete substrate may have a perimeter defined by first longitudinal edge 611, second longitudinal edge 612, first lateral edge 613, and second lateral edge 614. The second discrete substrate may have a perimeter defined by first longitudinal edge 621, second longitudinal edge 622, first lateral edge 623, and second lateral edge 624. The third discrete substrate may have a perimeter defined by first longitudinal edge 631, second longitudinal edge 632, first lateral edge 633, and second lateral edge 634.

As shown in the embodiments of FIGS. 30-37, the second discrete substrate 620 may be disposed at least partially intermediate the first discrete substrate 610 and the third discrete substrate 630. FIGS. 30-33 depict the second discrete substrate 620 disposed at least partially intermediate the first discrete substrate 610 and the third discrete substrate 630 along a longitudinal direction (running the same directional as the longitudinal axis 601). FIGS. 34-37 depict the second discrete substrate 620 disposed at least partially intermediate the first discrete substrate 610 and the third discrete substrate 630 along a lateral direction (running the same directional as the lateral axis 602).

Figure 30:
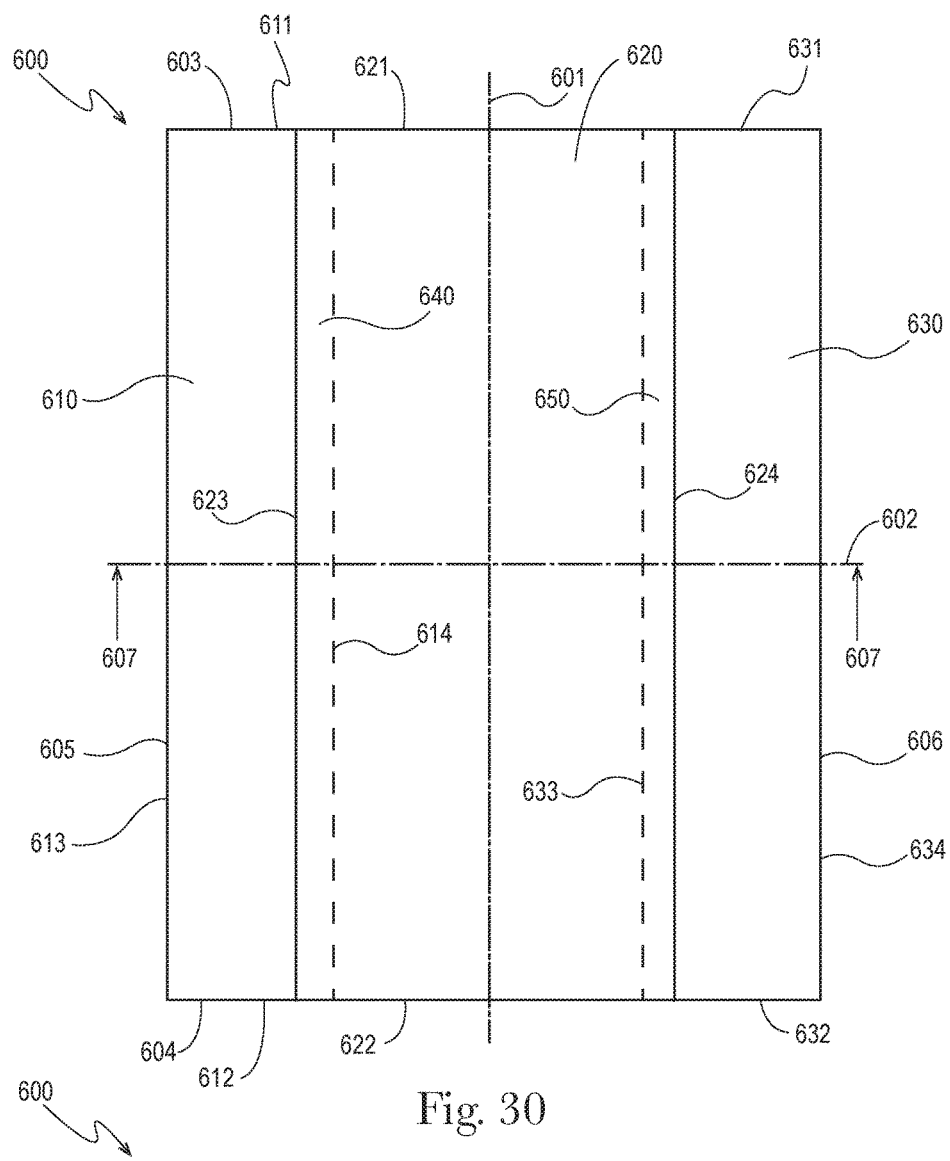
FIG. 30 is a schematic illustration of a top view of a multi-component topsheet in accordance with the present disclosure.
Figure 32:
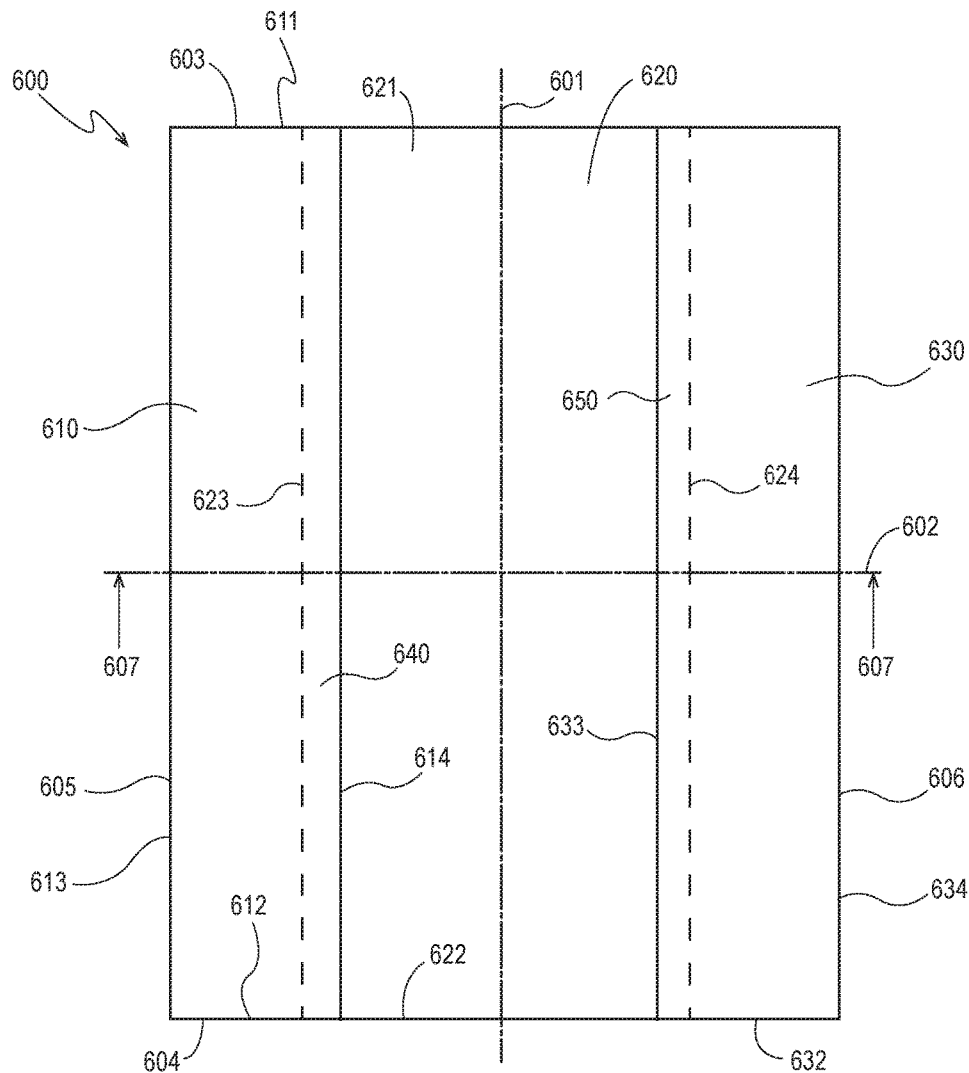
FIG. 32 is a schematic illustration of a top view of a multi-component topsheet in accordance with the present disclosure.
Figure 34:
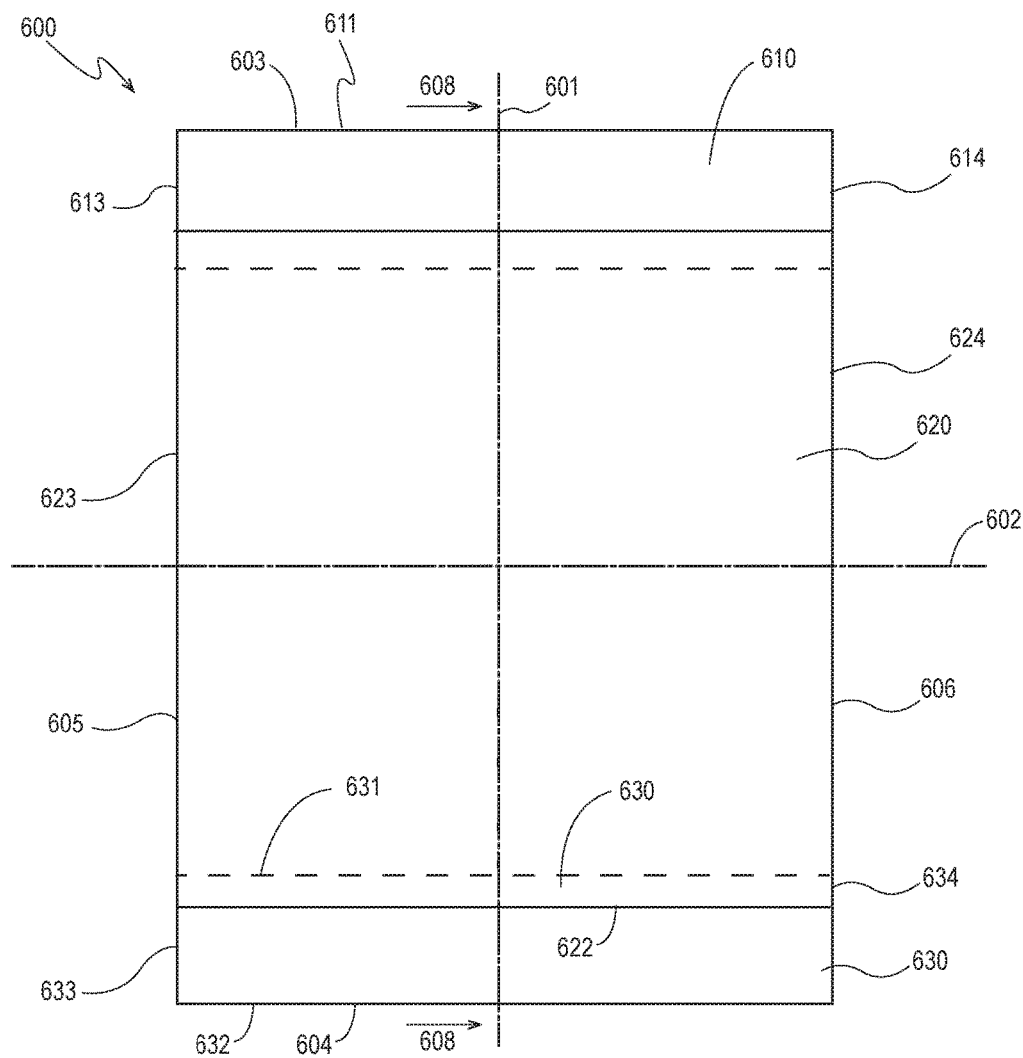
FIG. 34 is a schematic illustration of a top view of a multi-component topsheet in accordance with the present disclosure.
Figure 36:
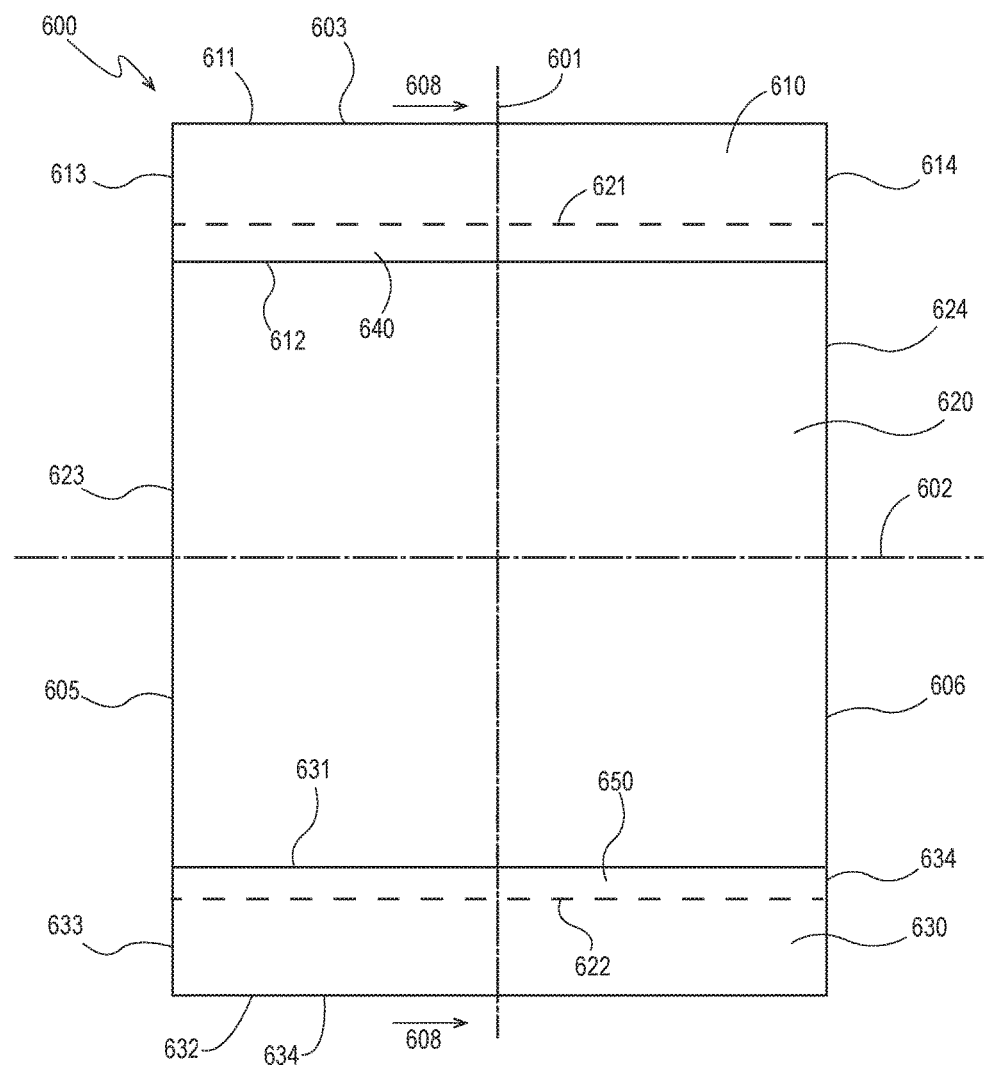
FIG. 36 is a schematic illustration of a top view of a multi-component topsheet in accordance with the present disclosure.

In some embodiments, the first and/or second longitudinal edges of the first discrete substrate 610, the second discrete substrate 620, and/or the third discrete substrate 630 will be common with the longitudinal edges 603, 604 of the multi-component topsheet 600. In some embodiments, the first and/or second lateral edge of the first discrete substrate 610, second discrete substrate 620, and/or the third discrete substrate 630 will be common with the lateral edges 605, 606 of the multi-component topsheet 600. In the non-limiting embodiments of FIGS. 30 and 32, the longitudinal edge 603 of the multi-component topsheet 600 is common with the longitudinal edges 611, 621, 631 of the first, second and third discrete substrates. In FIGS. 30 and 32, the longitudinal edge 604 of the multi-component topsheet 600 is common with the longitudinal edges 612, 622, 632 of the first, second and third discrete substrates. In FIGS. 30 and 32, the lateral edge 605 of the multi-component topsheet 600 is common with the first lateral edge 613 of the first discrete substrate 610. In FIGS. 30 and 32, the lateral edge 606 of the multi-component topsheet 600 is common with the second lateral edge 634 of the third discrete substrate 630. In the non-limiting embodiments of FIGS. 34 and 36, the longitudinal edge 603 of the multi-component topsheet 600 is common with the first longitudinal edge 611 of the first discrete substrate 610. In FIGS. 34 and 36, the longitudinal edge 604 of the multi-component topsheet 600 is common with the second longitudinal edge 632 of the third discrete substrate 630. In FIGS. 34 and 36, the lateral edge 605 of the multi-component topsheet 600 is common with the lateral edges 613, 623, 633 of the first, second and third discrete substrates. In FIGS. 34 and 36, the lateral edge 606 of the multi-component topsheet 600 is common with the lateral edges 614, 624, 634 of the first, second and third discrete substrates.

Figure 31:
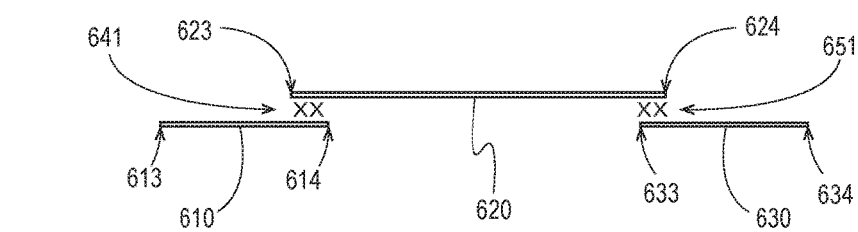
FIG. 31 is a schematic illustration of a cross-sectional view of the multi-component topsheet of FIG. 30.
Figure 33:
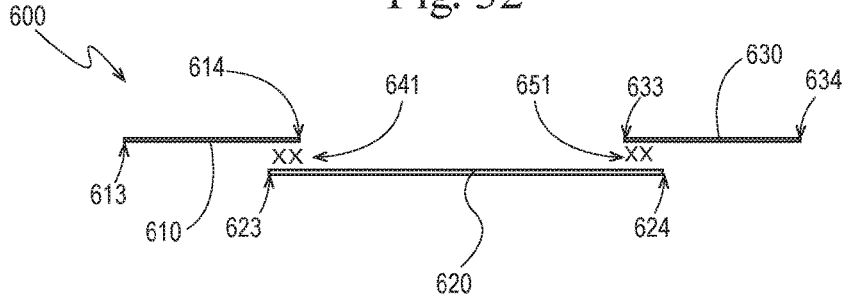
FIG. 33 is a schematic illustration of a cross-sectional view of the multi-component topsheet of FIG. 32.

FIGS. 30 and 32 schematically illustrate a top view of a body facing side of one embodiment of the multi-component topsheets 600 detailed herein. FIGS. 31 and 33 depict cross sectional views of FIGS. 30 and 32, respectively, taken about line 607. As shown in FIGS. 30-33, the second substrate 620 is disposed at least partially intermediate the first discrete substrate 610 and the third discrete substrate 630 along a longitudinal direction. The second substrate 620 is joined to the first discrete substrate 610 and the third discrete substrate 630, with overlapping substrate between the first and second discrete substrates and between the second and third discrete substrates. The joining of discrete substrates may be made by any method known in the art, including, but not limited to, mechanical bonding, hydroentangling, embossing, adhesive bonding, pressure bonding, heat bonding, or by other methods of joining multiple discrete substrates. The non-limiting embodiments of FIGS. 30-33 show the substrates joined by mechanical bonding 641, 651.

The overlap between the first discrete substrate 610 and the second discrete substrate 620 is, from a top view, the area contained by a perimeter consisting of the first lateral edge 623 of the second discrete substrate 620, the second lateral edge 614 of the first discrete substrate 610, the first longitudinal edge 621 of the second discrete substrate 620, and the second longitudinal edge 622 of the second discrete substrate 620. Because this area contains two layers of substrate (located between adjacent single layers of substrate), it is referred to as the first dual layer area 640. The overlap between the second discrete substrate 620 and the third discrete substrate 630 is, from a top view, the area contained by a perimeter consisting of the second lateral edge 624 of the second discrete substrate 620, the first lateral edge 633 of the third discrete substrate 630, the first longitudinal edge 621 of the second discrete substrate 620, and the second longitudinal edge 622 of the second discrete substrate 620. Because this area also contains two layers of substrate (located between adjacent single layers of substrate), it is referred to as the second dual layer area 650. The first dual layer area 640 and the second dual layer area 650 add up to form the dual layer of substrate of the multi-component topsheet 600. As a non-limiting example, utilizing the non-limiting embodiments shown in FIGS. 30-33, if the first dual layer area 640 is 10 cm$^2$ and the second dual layer area 650 is 10 cm$^2$, the dual layer of substrate for the multi-component topsheet 600 is 20 cm$^2$.

Still referring to the embodiments depicted in FIGS. 30-33, from a top view, the areas of the multi-component topsheet 600 that are not the dual layer of substrate are defined as a single layer of substrate. The single layer of substrate for this particular embodiment of multi-component topsheet 600 consists of three single layer areas added together. The first single layer area is the area, from a top view, contained by a perimeter consisting of the first lateral edge 613 of the first discrete substrate 610, the first lateral edge 623 of the second discrete substrate 620, the first longitudinal edge 611 of the first discrete substrate 610, and the second longitudinal edge 612 of the first discrete substrate 610. The second single layer area is the area, from a top view, contained by a perimeter consisting of the second lateral edge 614 of the first discrete substrate 610, the first lateral edge 633 of the third discrete substrate 630, the first longitudinal edge 621 of the second discrete substrate 620, and the second longitudinal edge 622 of the second discrete substrate 620. The third single layer area is the area, from a top view, contained by a perimeter consisting of the second lateral edge 624 of the second discrete substrate 620, the second lateral edge 634 of the third discrete substrate 630, the first longitudinal edge 631 of the third discrete substrate 630, and the second longitudinal edge 632 of the third discrete substrate 630. The first, second, and third single areas add up to form the single layer of substrate of the multi-component topsheet 600. As a non-limiting example, utilizing the embodiment shown in FIGS. 30-33, if the first single layer area is 50 cm$^2$, the second single layer area is 100 cm$^2$ and the third single layer area is 50 cm$^2$, the single layer of substrate for the multi-component topsheet 600 is 200 cm$^2$.

Still referring to the non-limiting embodiments depicted in FIGS. 30-33, the distance between the first lateral edge 613 of the first discrete substrate 610 and the second lateral edge 614 of the first discrete substrate 610 may be between about 20 mm and about 70 mm. The distance between the first lateral edge 633 of the third discrete substrate 630 and the second lateral edge 634 of the third discrete substrate 630 may be between about 20 mm and about 70 mm. The distance between the first lateral edge 613 of the first discrete substrate 610 and the first lateral edge 623 of the second discrete substrate 620 may be between about 16 mm and about 66 mm. The distance between the second lateral edge 624 of the second discrete substrate 620 and the second lateral edge 634 of the third discrete substrate 630 may be between about 16 mm and about 66 mm. The distance between the first lateral edge 623 of the second discrete substrate 620 and the second lateral edge 624 of the second discrete substrate 620 may be between about 40 mm and about 120 mm. The distance between the first lateral edge 623 of the second discrete substrate 620 and the second lateral edge 614 of the first discrete substrate 610 may be between about 4 mm and about 24 mm. The distance between the first lateral edge 633 of the third discrete substrate 630 and the second lateral edge 624 of the second discrete substrate 620 may be between about 4 mm and about 24 mm.

As shown in FIG. 30, looking down on a top view of the body facing side of an embodiment of the multi-component topsheet 600 (and also detailed in the cross sectional view of FIG. 31), the second discrete substrate 620 is disposed above the first discrete substrate 610 and the third discrete substrate 630. Accordingly, the overlap between the first discrete substrate 610 and the second discrete substrate 620 includes the garment facing side of the second discrete substrate contacting the body facing side of the first discrete substrate. Likewise, the overlap between the third discrete substrate 630 and the second discrete substrate 620 includes the garment facing side of the second discrete substrate contacting the body facing side of the third discrete substrate. Alternatively, as shown in FIG. 32, looking down on a top view of the body facing side of an embodiment of the multi-component topsheet 600 (and also detailed in the cross sectional view of FIG. 33), the second discrete substrate 620 is disposed below the first discrete substrate 610 and the third discrete substrate 630. Accordingly, the overlap between the first discrete substrate 610 and the second discrete substrate 620 includes the body facing side of the second discrete substrate contacting the garment facing side of the first discrete substrate. Likewise, the overlap between the third discrete substrate 630 and the second discrete substrate 620 includes the body facing side of the second discrete substrate contacting the garment facing side of the third discrete substrate.

Figure 35:
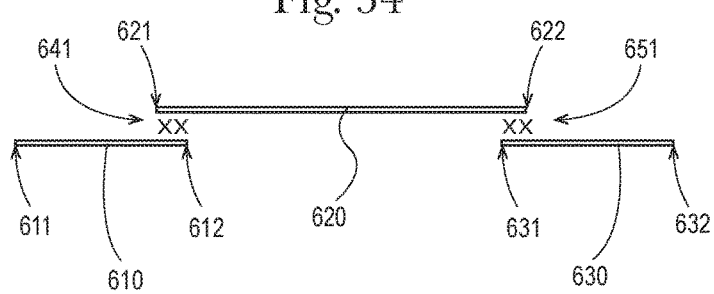
FIG. 35 is a schematic illustration of a cross-sectional view of the multi-component topsheet of FIG. 34.
Figure 37:
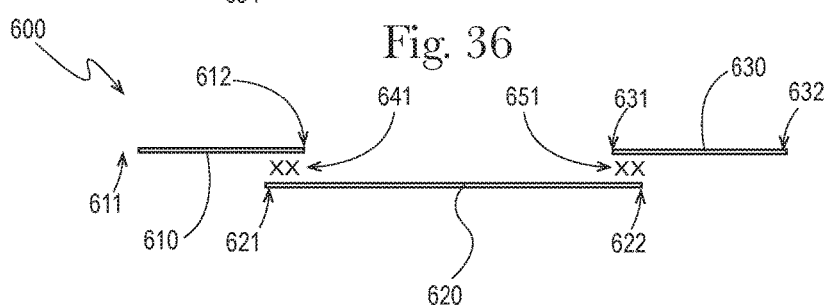
FIG. 37 is a schematic illustration of a cross-sectional view of the multi-component topsheet of FIG. 36.

FIGS. 34 and 36 schematically illustrate a top view of a body facing side of one embodiment of the multi-component topsheets 600 detailed herein. FIGS. 35 and 37 depict cross sectional views of FIGS. 34 and 36, respectively, taken about line 608. As shown in FIGS. 34-37, the second substrate 620 is disposed at least partially intermediate the first discrete substrate 610 and the third discrete substrate 630 along a lateral direction. The second substrate 620 is joined to the first discrete substrate 610 and the third discrete substrate 630, with overlapping substrate between the first and second discrete substrates and between the second and third discrete substrates. The joining of discrete substrates may be made by any method known in the art, including, but not limited to, mechanical bonding, hydroentangling, embossing, adhesive bonding, pressure bonding, heat bonding, or by other methods of joining multiple discrete substrates. The non-limiting embodiments of FIGS. 34-37 show the substrates joined by mechanical bonding 641, 651.

The overlap between the first discrete substrate 610 and the second discrete substrate 620 is, from a top view, the area contained by a perimeter consisting of the first lateral edge 623 of the second discrete substrate 620, the second lateral edge 624 of the second discrete substrate 620, the first longitudinal edge 621 of the second discrete substrate 620, and the second longitudinal edge 612 of the first discrete substrate 610. Because this area contains two layers of substrate (located between adjacent single layers of substrate), it is referred to as the first dual layer area 640 of multi-component topsheet 600. The overlap between the second discrete substrate 620 and the third discrete substrate 630 is, from a top view, the area contained by a perimeter consisting of the first lateral edge 623 of the second discrete substrate 620, the second lateral edge 624 of the second discrete substrate 620, the first longitudinal edge 631 of the third discrete substrate 630, and the second longitudinal edge 622 of the second discrete substrate 620. Because this area also contains two layers of substrate (located between adjacent single layers of substrate), it is referred to as the second dual layer area 650 of multi-component topsheet 600. The first dual layer area 640 and the second dual layer area 650 add up to form the dual layer of substrate of multi-component topsheet 600. As a non-limiting example, utilizing the embodiments shown in FIGS. 34-37, if the first dual layer area 640 is 10 cm$^2$ and the second dual layer area 650 is 10 cm$^2$, the dual layer of substrate for the multi-component topsheet 600 is 20 cm$^2$.

Still referring to the embodiments depicted in FIGS. 34-37, from a top view, the areas of the multi-component topsheet 600 that are not the dual layer of substrate are defined as a single layer of substrate. The single layer of substrate for this particular embodiment of multi-component topsheet 600 consists of three single layer areas added together. The first single layer area is the area, from a top view, contained by a perimeter consisting of the first lateral edge 613 of the first discrete substrate 610, the second lateral edge 614 of the first discrete substrate 610, the first longitudinal edge 611 of the first discrete substrate 610, and the first longitudinal edge 621 of the second discrete substrate 620. The second single layer area is the area, from a top view, contained by a perimeter consisting of the first lateral edge 623 of the second discrete substrate 620, the second lateral edge 624 of the second discrete substrate 620, the second longitudinal edge 612 of the first discrete substrate 610, and the first longitudinal edge 631 of the third discrete substrate 630. The third single layer area is the area, from a top view, contained by a perimeter consisting of the first lateral edge 633 of the third discrete substrate 630, the second lateral edge 634 of the third discrete substrate 630, the second longitudinal edge 622 of the second discrete substrate 620, and the second longitudinal edge 632 of the third discrete substrate 630. The first, second and third single areas add up to form the single layer of substrate of multi-component topsheet 600. As a non-limiting example, utilizing the embodiment shown in FIGS. 47-50, if the first single layer area is 50 cm$^2$, the second single layer area is 100 cm$^2$ and the third single layer area is 50 cm$^2$, the single layer of substrate for the multi-component topsheet 600 is 200 cm$^2$.

Still referring to the non-limiting embodiments depicted in FIGS. 34-37, the distance between the first longitudinal edge 611 of the first discrete substrate 610 and the second longitudinal edge 612 of the first discrete substrate 610 may be between about 20 mm and about 70 mm. The distance between the first longitudinal edge 631 of the third discrete substrate 630 and the second longitudinal edge 632 of the third discrete substrate 630 may be between about 20 mm and about 70 mm. The distance between the first longitudinal edge 611 of the first discrete substrate 610 and the first longitudinal edge 621 of the second discrete substrate 620 may be between about 16 mm and about 66 mm. The distance between the second longitudinal edge 622 of the second discrete substrate 620 and the second longitudinal edge 632 of the third discrete substrate 630 may be between about 16 mm and about 66 mm. The distance between the first longitudinal edge 621 of the second discrete substrate 620 and the second longitudinal edge 622 of the second discrete substrate 620 may be between about 40 mm and about 120 mm. The distance between the first longitudinal edge 621 of the second discrete substrate 620 and the second longitudinal edge 612 of the first discrete substrate 610 may be between about 4 mm and about 24 mm. The distance between the first longitudinal edge 631 of the third discrete substrate 630 and the second longitudinal edge 622 of the second discrete substrate 620 may be between about 4 mm and about 24 mm.

As shown in FIG. 34, looking down on a top view of the body facing side of an embodiment of the multi-component topsheet 600 (and also detailed in the cross sectional view of FIG. 35), the second discrete substrate 620 is disposed above the first discrete substrate 610 and the third discrete substrate 630. Accordingly, the overlap between the first discrete substrate 610 and the second discrete substrate 620 includes the garment facing side of the second discrete substrate contacting the body facing side of the first discrete substrate. Likewise, the overlap between the third discrete substrate 630 and the second discrete substrate 620 includes the garment facing side of the second discrete substrate contacting the body facing side of the third discrete substrate. Alternatively, as shown in FIG. 36, looking down on a top view of the body facing side of an embodiment of the multi-component topsheet 600 (and also detailed in the cross sectional view of FIG. 37), the second discrete substrate 620 is disposed below the first discrete substrate 610 and the third discrete substrate 630. Accordingly, the overlap between the first discrete substrate 610 and the second discrete substrate 620 includes the body facing side of the second discrete substrate contacting the garment facing side of the first discrete substrate. Likewise, the overlap between the third discrete substrate 630 and the second discrete substrate 620 includes the body facing side of the second discrete substrate contacting the garment facing side of the third discrete substrate.

In some embodiments, the single layer of substrate may comprise about 80% or more of the total area of the multi-component topsheet 600, and the dual layer of substrate may comprise about 20% or less of the total area of the multi-component topsheet 600. In other embodiments, the single layer of substrate may comprise about 70% or more, about 75% or more, about 85% or more, about 90% or more, or about 95% or more of the total area of the multi-component topsheet 600, and the dual layer of substrate may comprise about 30% or less, about 25% or less, about 15% or less, about 10% or less, or about 5% or less of the total area of the multi-component topsheet 600.

The first discrete substrate 610, the second discrete substrate 620, and/or the third discrete substrate 630 may be composed of any one or more of the three-dimensional substrates detailed herein. In some embodiments, the second discrete substrate 620 is composed of an embodiment of the three-dimensional substrates detailed herein, and both the first discrete substrate 610 and the third discrete substrate 630 are made of traditional topsheet materials, such as P10. P10 is a 12 gsm or 15 gsm basis weight poly-propylene nonwoven substrate (as further detailed herein), available from Polymer Group, Inc of Charlotte, N.C. According to the Descriptive Analysis Roughness Test, P10 has a geometric roughness of between about 2.2 and about 2.8, and in some embodiments, geometric roughness of about 2.6. In some embodiments, both the first discrete substrate 610 and the third discrete substrate 630 are composed of the same material, but in other embodiments, the first and second discrete substrates may be composed of different materials.

When viewed from the top, the multi-component topsheets 600 may have one or more shapes, patterns or other distinct visible interfaces between the first discrete substrate 610 and the second discrete substrate 620, and between the second discrete substrate and the third discrete substrate 630. Depending on whether the second discrete substrate 620 is located above (as depicted in FIGS. 30, 31, 34 and 35) or below (as depicted in FIGS. 32, 33, 36 and 37) the first discrete substrate 610 and third discrete substrate 630, the longitudinal or lateral edges of the first, second or third discrete substrates may determine the shape of the visible interface. For example, in the embodiment depicted in FIGS. 43 and 44, the shape or pattern of the first lateral edge 623 of the second discrete substrate 620 will determine the visible interface adjacent the first dual layer area 640 and the shape or pattern of the second lateral edge 624 of the second discrete substrate 620 will determine the visible interface adjacent the second dual layer area 650. In the embodiment depicted in FIGS. 32 and 33, the shape or pattern of the second lateral edge 614 of the first discrete substrate 610 will determine the visible interface adjacent the first dual layer area 640 and the shape or pattern of the first lateral edge 633 of the third discrete substrate 630 will determine the visible interface adjacent the second dual layer area 650. In the embodiment depicted in FIGS. 34 and 35, the shape or pattern of the first longitudinal edge 621 of the second discrete substrate 620 will determine the visible interface adjacent the first dual layer area 640 and the shape or pattern of the second longitudinal edge 622 of the second discrete substrate 620 will determine the visible interface adjacent the second dual layer area 650. In the embodiment depicted in FIGS. 36 and 37, the shape or pattern of the second longitudinal edge 612 of the first discrete substrate 610 will determine the visible interface adjacent the first dual layer area 640 and the shape or pattern of the first longitudinal edge 631 of the third discrete substrate 630 will determine the visible interface adjacent the second dual layer area 650.

Figure 38:
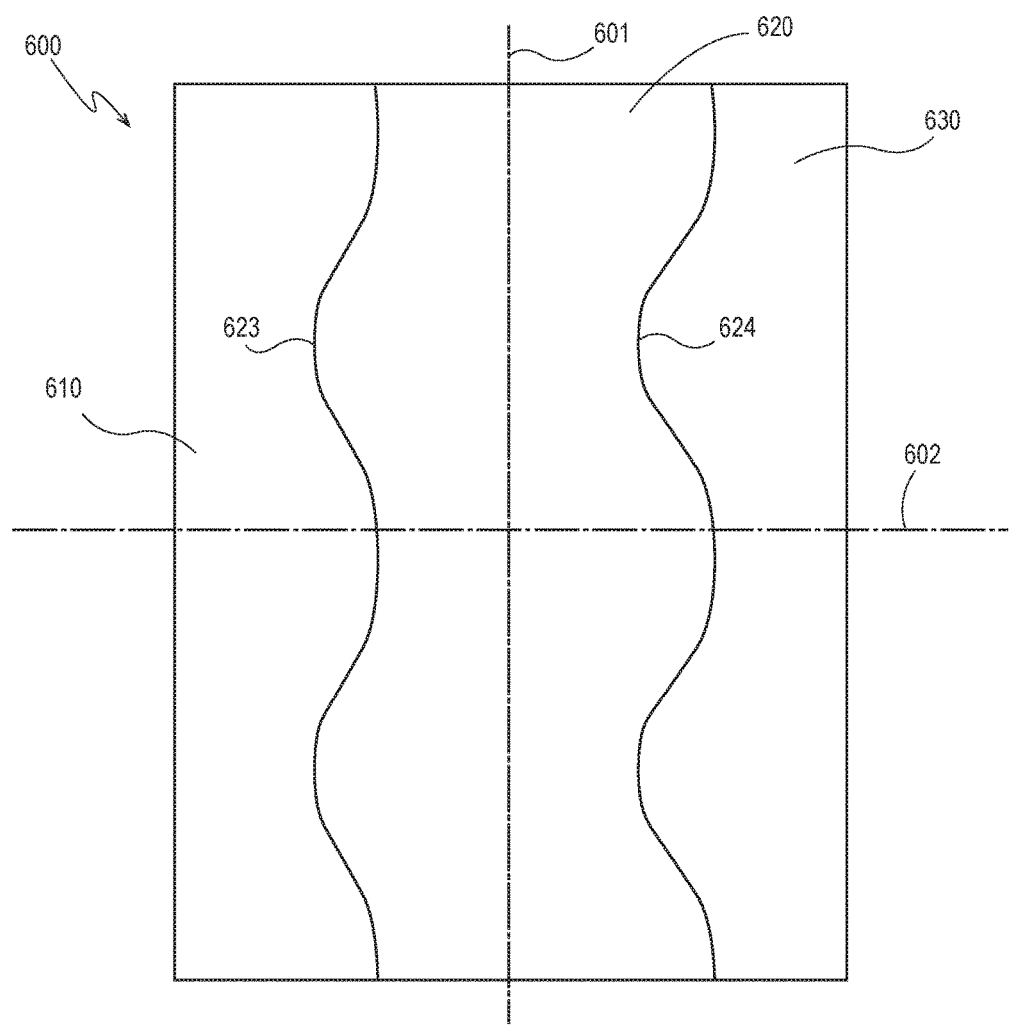
FIG. 38 is a schematic illustration of a top view of a multi-component topsheet in accordance with the present disclosure.
Figure 39:
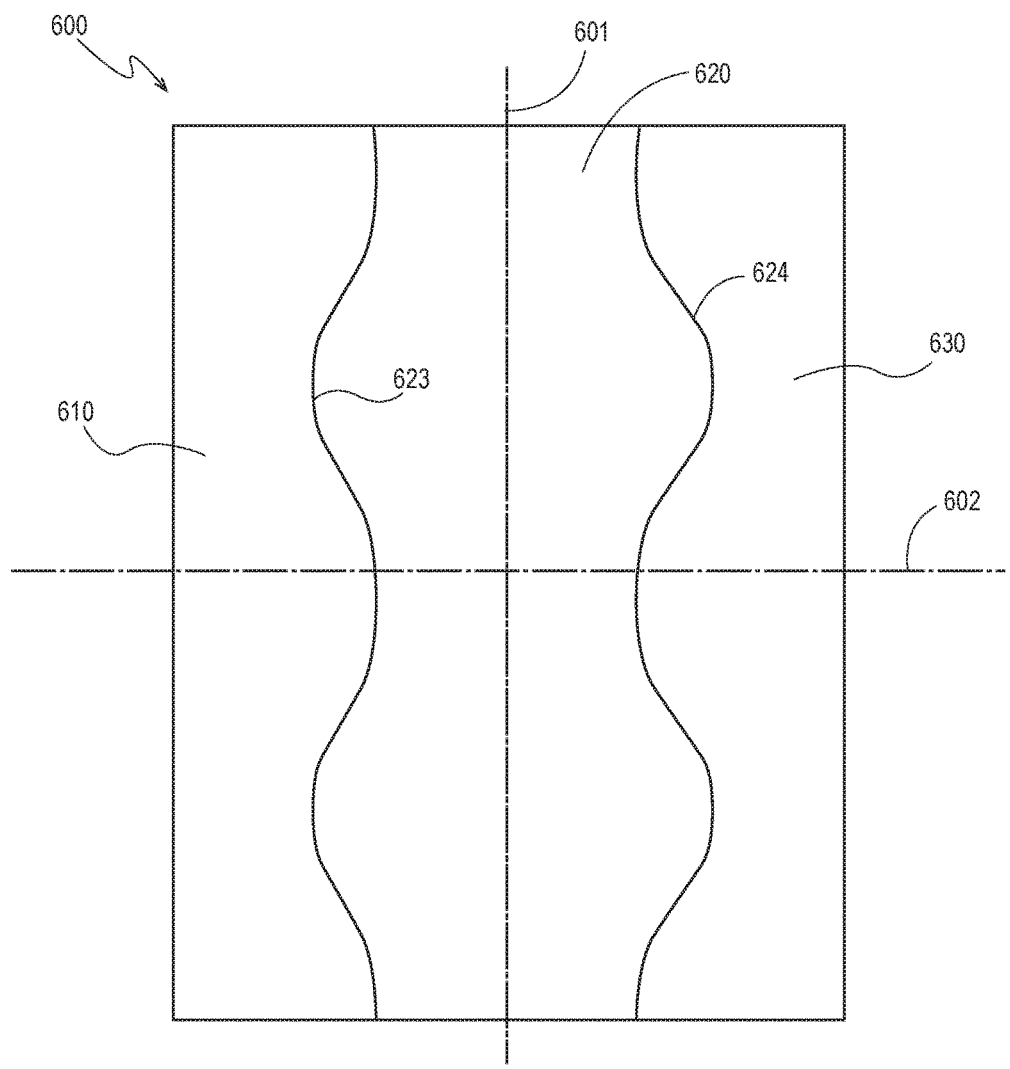
FIG. 39 is a schematic illustration of a top view of a multi-component topsheet in accordance with the present disclosure.
Figure 40:
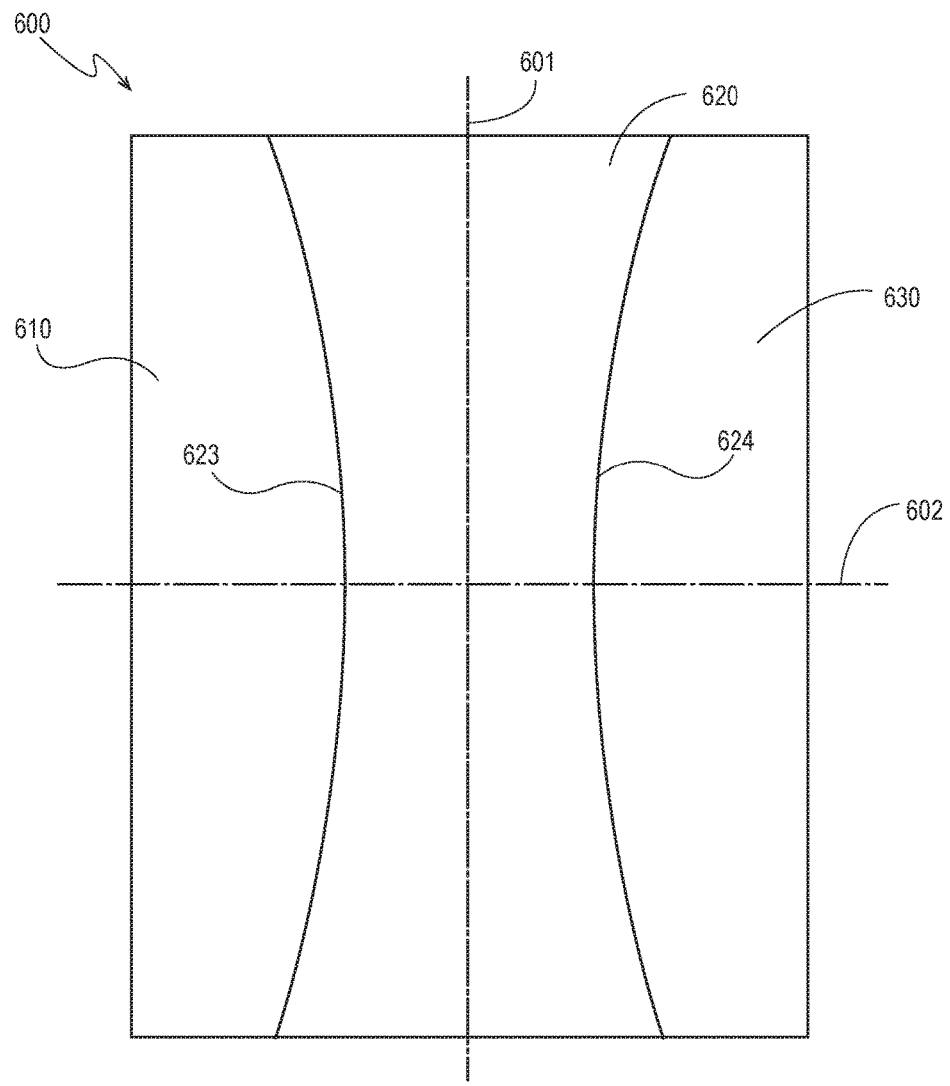
FIG. 40 is a schematic illustration of a top view of a multi-component topsheet in accordance with the present disclosure.
Figure 41:
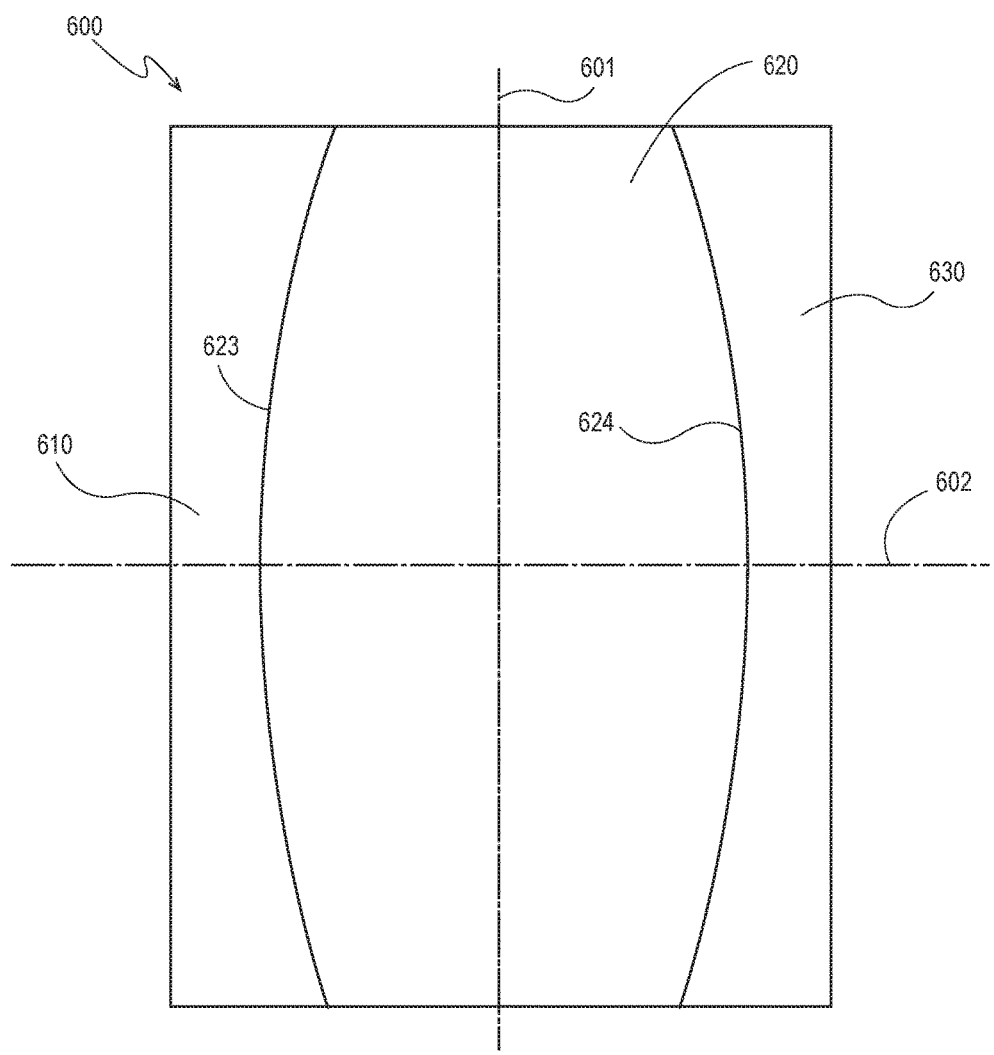
FIG. 41 is a schematic illustration of a top view of a multi-component topsheet in accordance with the present disclosure.

In any of the non-limiting embodiments of FIGS. 30-37, the lateral edges or longitudinal edges that create the visible interface between the second discrete layer 620 and the first discrete layer 610, and between the second discrete layer 620 and the third discrete layer 630 may be linear (i.e., straight line) or non-linear (i.e., not a straight line), and symmetrical or asymmetrical about either the lateral or longitudinal axes 601, 602. FIGS. 30-37 are examples of linear, symmetrical visible interfaces. For non-limiting examples of additional visible interfaces (dependent on any combination of longitudinal and/or lateral edges of the first, second, and/or third discrete substrates), please refer to FIGS. 38-45. FIG. 38 depicts a multi-component topsheet 600 with a visible interface that is non-linear and asymmetrical about the longitudinal axis. One way to achieve such a visible interface is to have a multi-component topsheet 600 with the second discrete substrate 620 disposed above the first and third discrete substrates 610, 630, and the first lateral edge 623 and the second lateral edge 624 of the second discrete substrate are non-linear and asymmetrical about the longitudinal axis 601 of the topsheet. In this particular example, repeating waves form the visible interface. However, in other embodiments, all kinds of waves may be used, such as sine waves, saw tooth waves, square waves, etc. FIG. 39 depicts a multi-component topsheet 600 with a visible interface that is non-linear and symmetrical about the longitudinal axis. One way to achieve such a visible interface is to have a multi-component topsheet 600 with the second discrete substrate 620 disposed above the first and third discrete substrates 610, 630, and the first lateral edge 623 and the second lateral edge 624 of the second discrete substrate are non-linear and symmetrical about the longitudinal axis 601 of the topsheet. FIGS. 40 and 41 are further examples of multi-component topsheet 600 with non-linear and symmetrical visible interfaces along the longitudinal axis 601.

Figure 42:
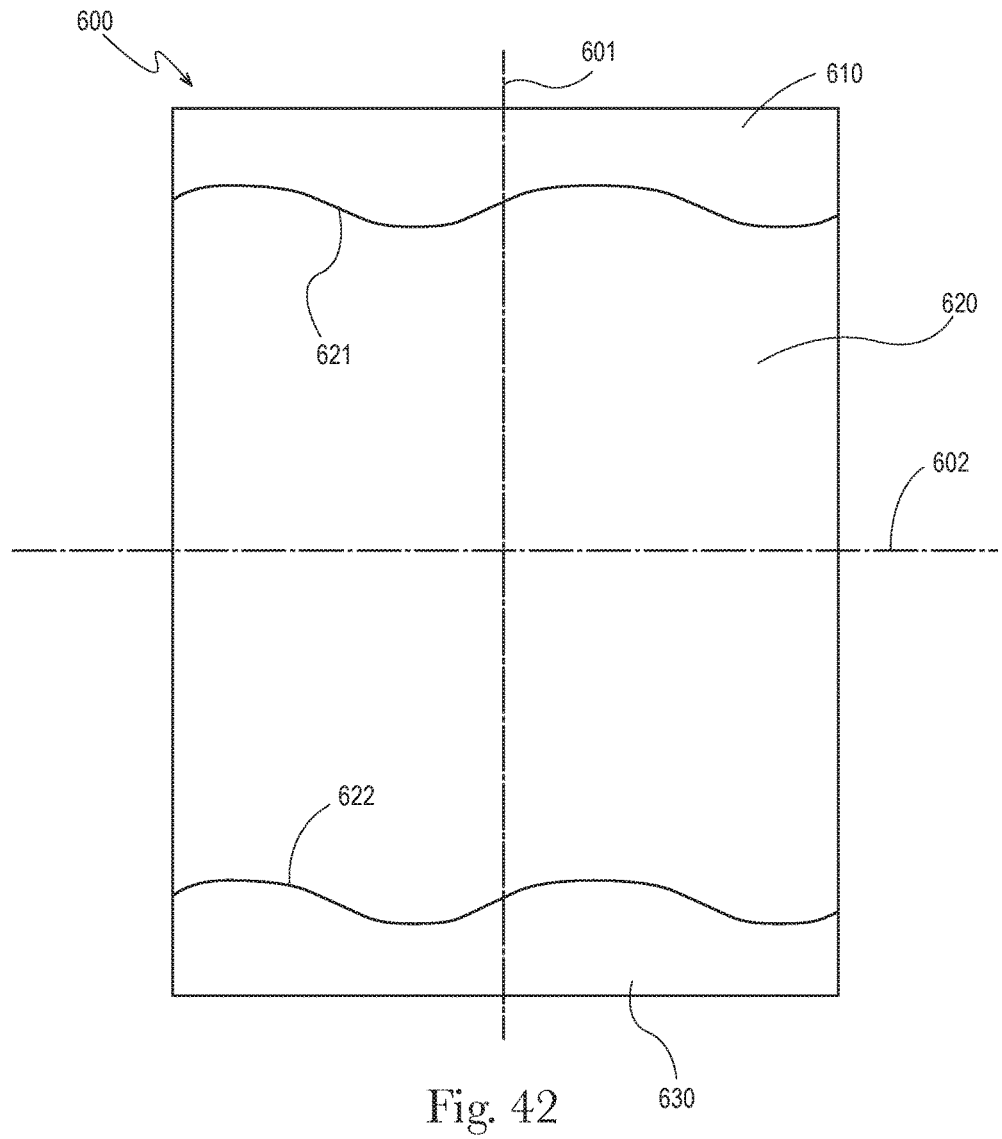
FIG. 42 is a schematic illustration of a top view of a multi-component topsheet in accordance with the present disclosure.
Figure 43:
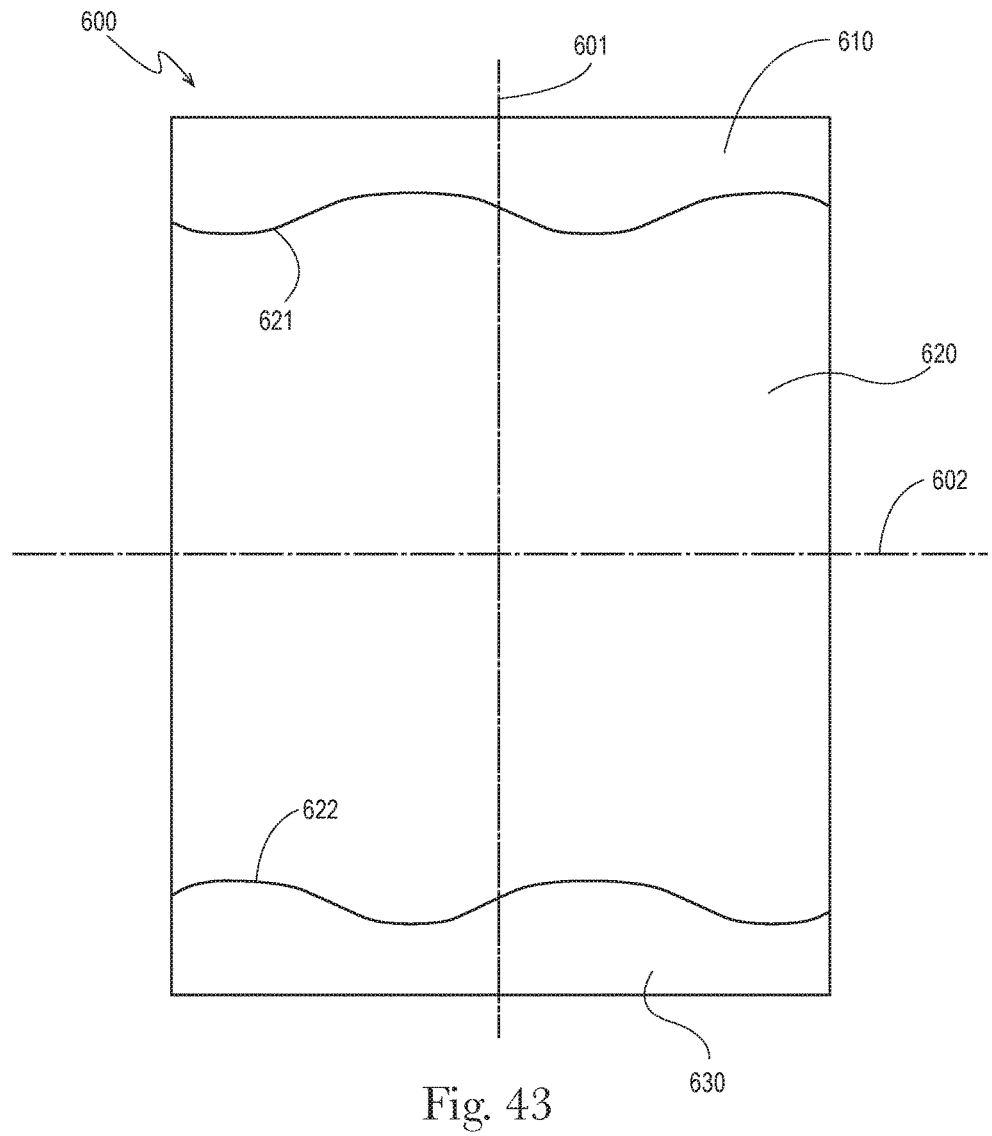
FIG. 43 is a schematic illustration of a top view of a multi-component topsheet in accordance with the present disclosure.
Figure 44:
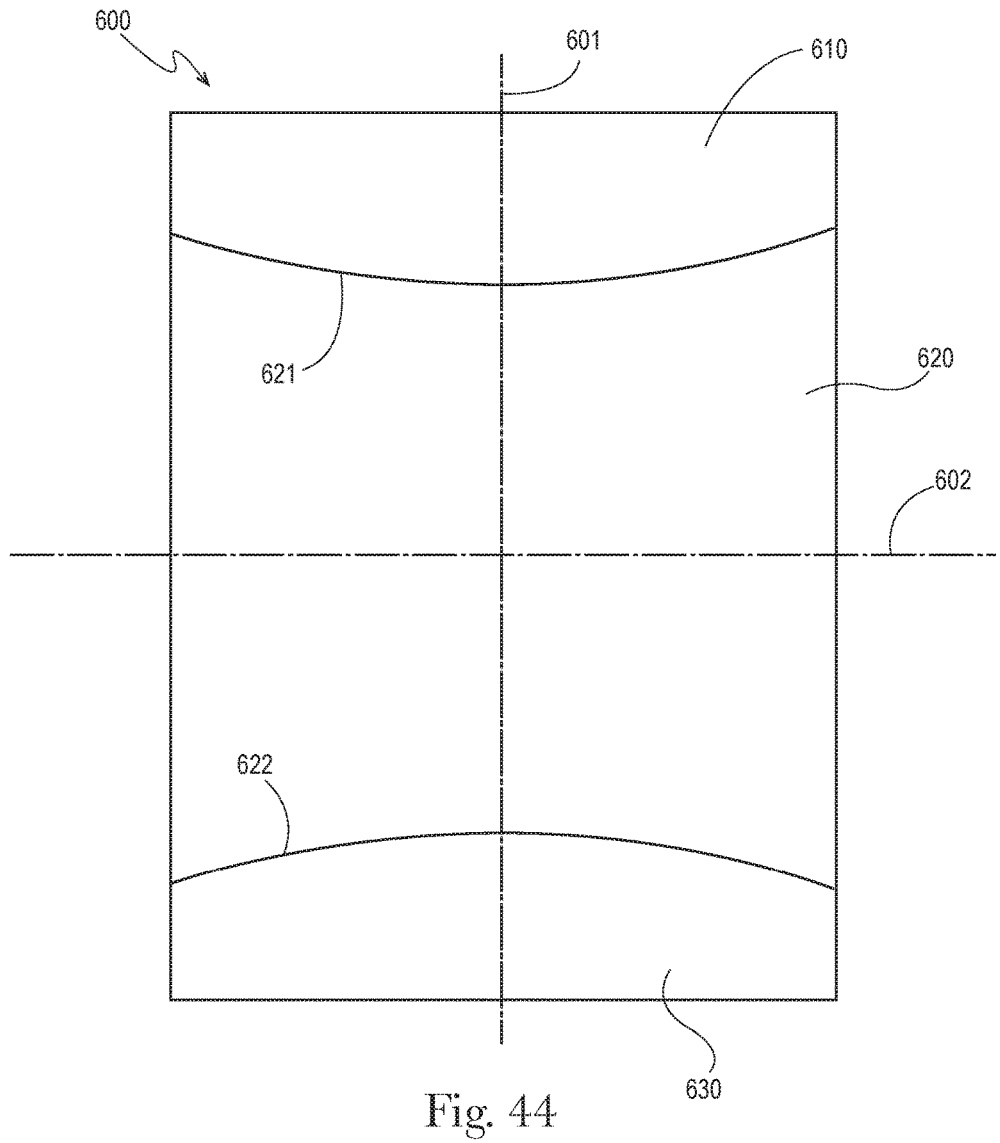
FIG. 44 is a schematic illustration of a top view of a multi-component topsheet in accordance with the present disclosure.
Figure 45:
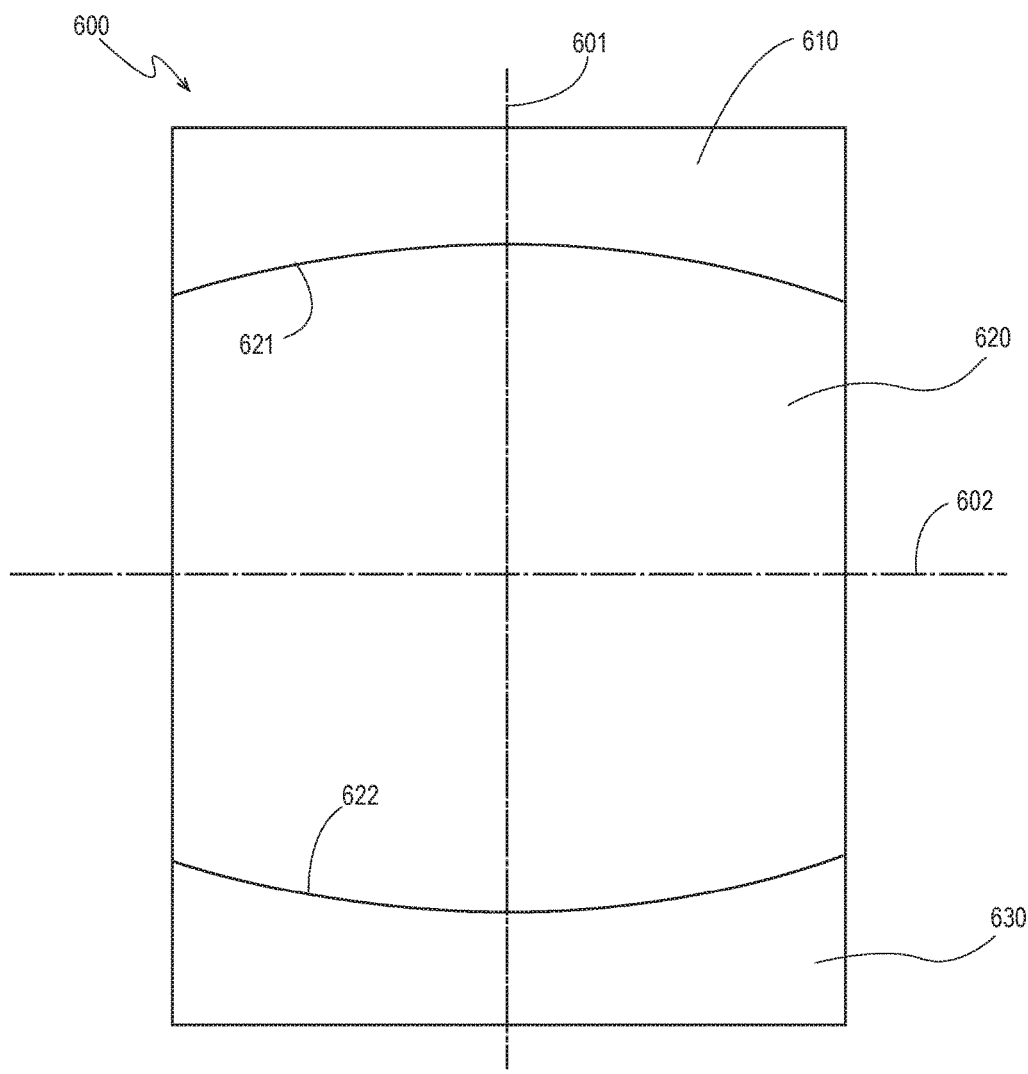
FIG. 45 is a schematic illustration of a top view of a multi-component topsheet in accordance with the present disclosure.

FIG. 42 depicts a multi-component topsheet 600 with a visible interface that is non-linear and asymmetrical about the lateral axis 602. One way to achieve such a visible interface is to have a multi-component topsheet 600 with the second discrete substrate 620 disposed above the first and third discrete substrates 610, 630, and the first longitudinal edge 621 and the second longitudinal edge 622 of the second discrete substrate are non-linear and asymmetrical about the lateral axis 602 of the topsheet. In this particular example, repeating waves form the visible interface. However, in other embodiments, all kinds of waves may be used, such as sine waves, saw tooth waves, square waves, etc. FIG. 43 depicts a multi-component topsheet 600 with a visible interface that is non-linear and symmetrical about the lateral axis. One way to achieve such a visible interface is to have a multi-component topsheet 600 with the second discrete substrate 620 disposed above the first and third discrete substrates 610, 630, and the first longitudinal edge 621 and the second longitudinal edge 622 of the second discrete substrate are non-linear and symmetrical about the lateral axis 602 of the topsheet. FIGS. 44 and 45 are further examples of a multi-component topsheet 600 with a non-linear and symmetrical visible interface about a lateral axis 602. In addition to these specific embodiments, it is contemplated that any combination of linear and/or non-linear, symmetrical and/or asymmetrical visible interfaces may be employed with the multi-component topsheets 600 detailed herein.

In some embodiments of multi-component topsheet 600, there may be a color difference between the first discrete substrate 610, the second discrete substrate 620, and/or the third discrete substrate 630. For example the first discrete substrate 610 and the third discrete substrate 630 may be a first color (e.g., purple, green, teal, blue), and the second discrete substrate 620 may be a second, different color, such as white. Alternatively, the first discrete substrate 610 and the third discrete substrate 630 may be white and the second discrete substrate 620 may be a different color.

FIGS. 46-57 depict top and cross-sectional schematic illustrations of embodiments of a multi-component topsheet 700. The multi-component topsheet 700 may include a first discrete substrate 710 and a second discrete substrate 720, and optionally in some embodiments (e.g., FIGS. 50-52 and 55-57), a third discrete substrate 730. The multi-component topsheet 700 has a longitudinal axis 701 that runs the longer overall dimension of the topsheet (in this case, the MD or machine direction), and a lateral axis 702 that runs perpendicular to the longitudinal axis. The multi-component topsheet 700 may have an overall outer perimeter defined by first longitudinal edge 703, second longitudinal edge 704, first lateral edge 705, and second lateral edge 706. The first discrete substrate may have an outer perimeter defined by first longitudinal edge 711, second longitudinal edge 712, first lateral edge 713, and second lateral edge 714. The first discrete substrate may have an inner perimeter defined by first longitudinal edge 715, second longitudinal edge 716, first lateral edge 717, and second lateral edge 718. The second discrete substrate may have an outer perimeter defined by first longitudinal edge 721, second longitudinal edge 722, first lateral edge 723, and second lateral edge 724. The second discrete substrate may have an inner perimeter defined by first longitudinal edge 725, second longitudinal edge 726, first lateral edge 727, and second lateral edge 728. In embodiments that include a third discrete substrate 730, the third discrete substrate may have a perimeter defined by first longitudinal edge 731, second longitudinal edge 732, first lateral edge 733, and second lateral edge 734.

The outer perimeter of the first discrete substrate 710 may form about 80% or more of the overall outer perimeter of the multi-component topsheet 700, and about 80% or more of the outer perimeter of the second discrete substrate 720 may be joined with a portion of the first discrete substrate. In some embodiments, the outer perimeter of the first discrete substrate 710 may comprise about 70% or more, about 75% or more, about 85% or more, about 90% or more, about 95% or more, or 100% of the overall outer perimeter of the multi-component topsheet 700. In some embodiments, about 70% or more, about 75% or more, about 85% or more, about 90% or more, about 95% or more, or 100% of the outer perimeter of the second discrete substrate 720 may be joined with a portion of the first discrete substrate 710. In some embodiments, about 70% or more, about 75% or more, about 85% or more, about 90% or more, about 95% or more, or 100% of the perimeter of the third discrete substrate 730 may be in contact with a portion of the second discrete substrate 720.

Figure 53:
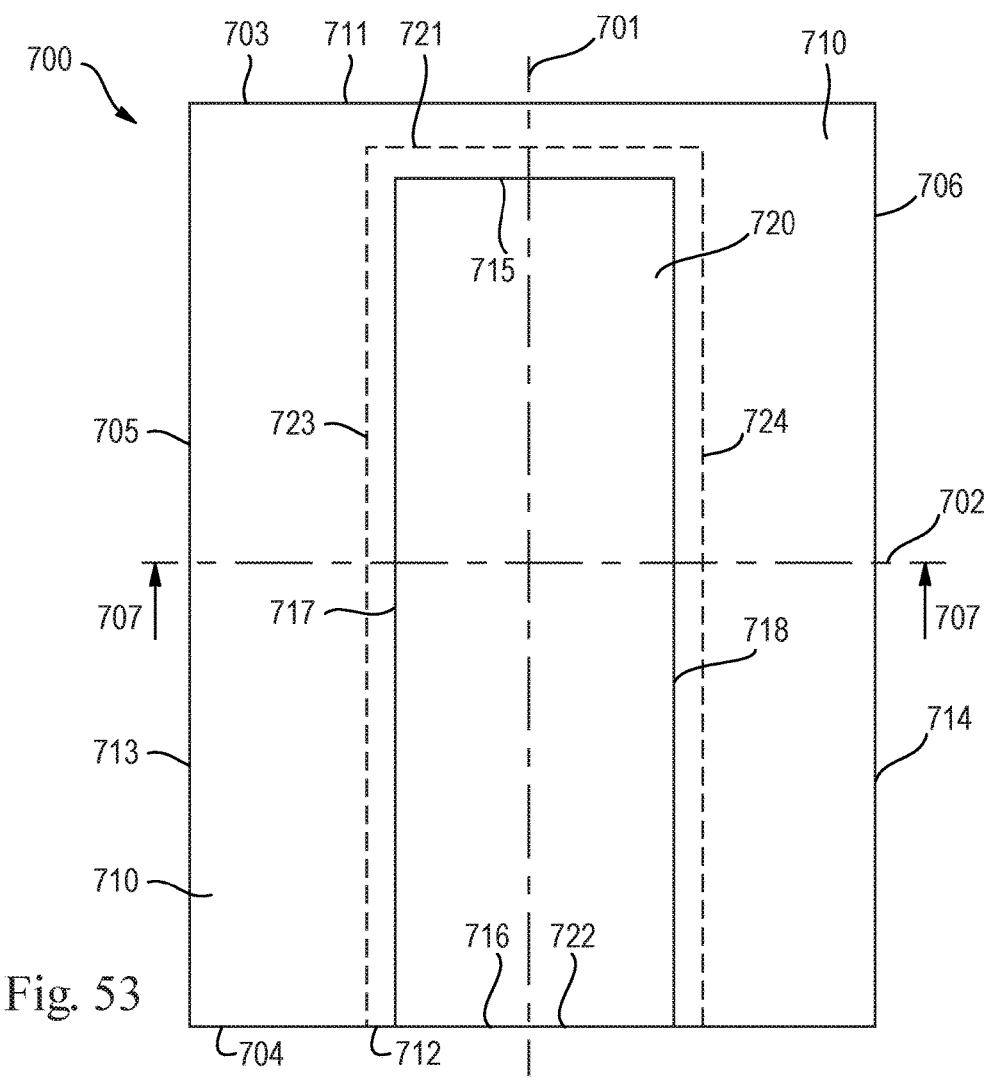
FIG. 53 is a schematic illustration of a top view of a multi-component topsheet in accordance with the present disclosure.
Figure 54:
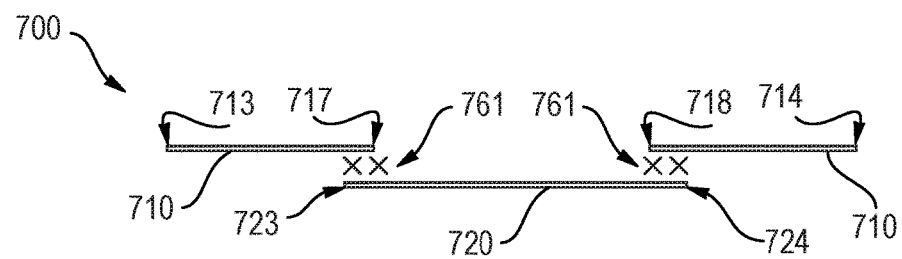
FIG. 54 is a schematic illustration of a cross-sectional view of the multi-component topsheet of FIG. 53.
Figure 55:
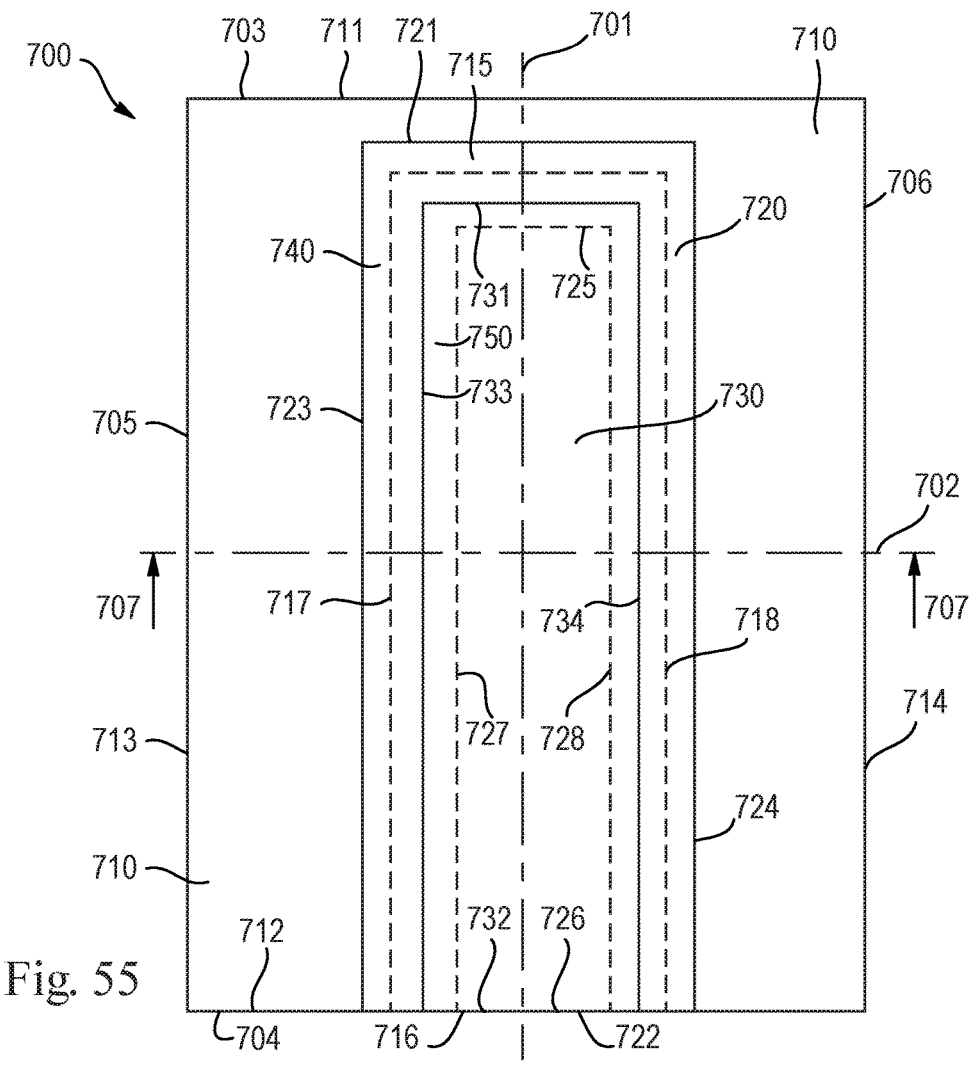
FIG. 55 is a schematic illustration of a top view of a multi-component topsheet in accordance with the present disclosure.
Figure 56:
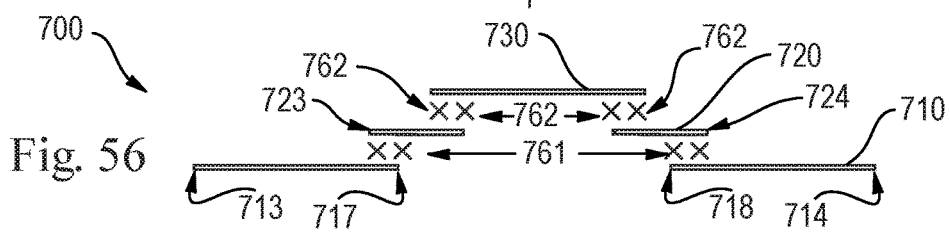
FIG. 56 is a schematic illustration of a cross-sectional view of the multi-component topsheet of FIG. 55.
Figure 57:
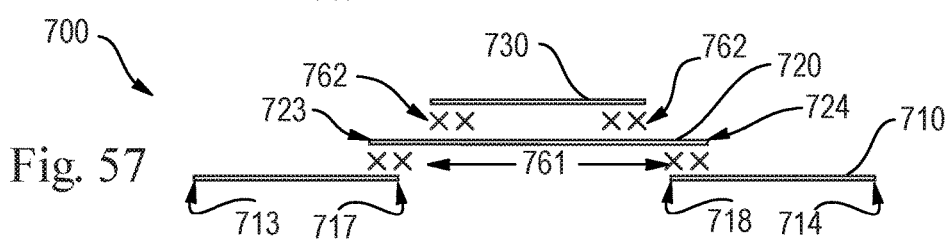
FIG. 57 is a schematic illustration of a cross-sectional view of the multi-component topsheet of FIG. 55.

In some embodiments, the first and/or second longitudinal edges of the first discrete substrate 710, the second discrete substrate 720, and/or the third discrete substrate 730 will be common with the longitudinal edges 703, 704 of the multi-component topsheet 700. In some embodiments, the first and/or second lateral edges of the first discrete substrate 710, second discrete substrate 720, and/or the third discrete substrate 730 will be common with the lateral edges 705, 706 of the multi-component topsheet 700. In the non-limiting embodiments of FIGS. 46-52 the longitudinal edge 703 of the multi-component topsheet 700 is common with the longitudinal edge 711 of the first discrete substrate 710. In FIGS. 46-52, the longitudinal edge 704 of the multi-component topsheet 700 is common with the longitudinal edge 712 of the first discrete substrate 710. In FIGS. 46-52, the lateral edge 705 of the multi-component topsheet 700 is common with the lateral edge 713 of the first discrete substrate 610. In FIGS. 46-52, the lateral edge 706 of the multi-component topsheet 700 is common with the lateral edge 714 of the first discrete substrate 710. In the non-limiting embodiment of FIGS. 53 and 54 the longitudinal edge 703 of the multi-component topsheet 700 is common with the longitudinal edge 711 of the first discrete substrate 710. In FIGS. 53 and 54, the longitudinal edge 704 of the multi-component topsheet 700 is common with the longitudinal edges 712 and 722 of the first and second discrete substrates. In FIGS. 53 and 54, the lateral edge 705 of the multi-component topsheet 700 is common with the lateral edge 713 of the first discrete substrate 710. In FIGS. 53 and 54, the lateral edge 706 of the multi-component topsheet 700 is common with the lateral edge 714 of the first discrete substrate 710. In the non-limiting embodiment of FIGS. 55-57 the longitudinal edge 703 of the multi-component topsheet 700 is common with the longitudinal edge 711 of the first discrete substrate 710. In FIGS. 55-57, the longitudinal edge 704 of the multi-component topsheet 700 is common with the longitudinal edges 712, 722 and 732 of the first, second, and third discrete substrates. In FIGS. 55-57, the lateral edge 705 of the multi-component topsheet 700 is common with the lateral edge 713 of the first discrete substrate 710. In FIGS. 55-57, the lateral edge 706 of the multi-component topsheet 700 is common with the lateral edge 714 of the first discrete substrate 710.

FIGS. 46, 48, 50, 53, and 55 schematically illustrate a top view of a body facing side of one embodiment of the multi-component topsheets 700 detailed herein. FIGS. 47, 49, 51, 52, 54, 56, and 57 depict cross sectional views of FIGS. 46, 48, 50, 53, and 55, respectively, taken about line 707. As shown in FIGS. 46-57, the second discrete substrate 720 may be surrounded by (i.e., either fully surrounded on all four sides or partially surrounded on three sides) and joined to the first discrete substrate 710, with overlapping substrate between the first and second discrete substrates. The joining of the discrete substrates may be made by any method known in the art, including, but not limited to, mechanical bonding, hydroentangling, embossing, adhesive bonding, pressure bonding, heat bonding, or by other methods of joining multiple discrete substrates. The non-limiting embodiments of FIGS. 46-57 show the substrates joined by mechanical bonding 761. In certain embodiments, the second discrete substrate 720 can be joined to the third discrete substrate 730 by any method known in the art (mechanical bonding, hydroentangling, embossing, adhesive bonding, pressure bonding, heat bonding, or by other methods of joining multiple discrete substrates), and in some particular embodiments, by mechanical bonding 762.

The overlap between the first discrete substrate 710 and the second discrete substrate 720 is, from a top view, the area contained by perimeter consisting of the first longitudinal edge 721 of the second discrete substrate 720, the second longitudinal edge 722 of the second discrete substrate 720, the first lateral edge 723 of the second discrete substrate 720, and the second lateral edge 724 of the second discrete substrate 720, minus the area contained by a perimeter consisting of the inner perimeter first longitudinal edge 715 of the first discrete substrate 710, the inner perimeter second longitudinal edge 716 of the first discrete substrate 710, the inner perimeter first lateral edge 717 of the first discrete substrate 710, and the inner perimeter second lateral edge 718 of the first discrete substrate 710. As a non-limiting example, utilizing the embodiments shown in FIGS. 46-49, if the area contained by the outer perimeter of the second discrete substrate 720 is 240 cm$^2$ and the area contained by the inner perimeter of the first discrete substrate 710 is 220 cm$^2$, the dual layer of substrate for the multi-component topsheet 700 is 20 cm$^2$.

Still referring to the embodiments depicted in FIGS. 46-49 and 53-54, from a top view, the areas of the multi-component topsheet 700 that are not the dual layer of substrate are defined as a single layer of substrate. The single layer of substrate for this particular embodiment of multi-component topsheet 700 consists of two single layer areas added together. The first single layer area is the area, from a top view, contained by a perimeter consisting of the first lateral edge 713 of the first discrete substrate 710, the second lateral edge 714 of the first discrete substrate 710, the first longitudinal edge 711 of the first discrete substrate 710, and the second longitudinal edge 712 of the first discrete substrate 710, minus the area contained by a perimeter consisting of the first lateral edge 723 of the second discrete substrate 720, the second lateral edge 724 of the second discrete substrate 720, the first longitudinal edge 721 of the second discrete substrate 720, and the second longitudinal edge 722 of the second discrete substrate 720. The second single layer area is the area, from a top view, contained by a perimeter consisting of the inner perimeter first lateral edge 717 of the first discrete substrate 710, the inner perimeter second lateral edge 718 of the first discrete substrate 710, the inner perimeter first longitudinal edge 715 of the first discrete substrate 710, and the inner perimeter second longitudinal edge 716 of the first discrete substrate 710. The first and second single areas add up to form the single layer of substrate. As a non-limiting example, utilizing the embodiment shown in FIGS. 46 and 47, if the first single layer area is 120 cm² and the second single layer area is 80 cm², the single layer of substrate for the multi-component topsheet 700 is 200 cm².

Referring now to the embodiments of multi-component topsheet 700 with a third discrete substrate 730 (as depicted in FIGS. 50-52 and 55-57) the overlap between the first discrete substrate 710 and the second discrete substrate 720 is, from a top view, the area contained by a perimeter consisting of the first longitudinal edge 721 of the second discrete substrate 720, the second longitudinal edge 722 of the second discrete substrate 720, the first lateral edge 723 of the second discrete substrate 720, and the second lateral edge 724 of the second discrete substrate 720, minus the area contained by a perimeter consisting of the inner perimeter first longitudinal edge 715 of the first discrete substrate 710, the inner perimeter second longitudinal edge 716 of the first discrete substrate 710, the inner perimeter first lateral edge 717 of the first discrete substrate 710, and the inner perimeter second lateral edge 718 of the first discrete substrate 710. Because this area contains two layers of substrate (located between adjacent single layers of substrate), it is referred to as the first dual layer area 740. The overlap between the second discrete substrate 720 and the third discrete substrate 730 is, from a top view, the area contained by a perimeter consisting of the first longitudinal edge 731 of the third discrete substrate 730, the second longitudinal edge 732 of the third discrete substrate 730, the first lateral edge 733 of the third discrete substrate 730, and the second lateral edge 734 of the third discrete substrate 730, minus the area contained by a perimeter consisting of the inner perimeter first longitudinal edge 725 of the second discrete substrate 720, the inner perimeter second longitudinal edge 726 of the second discrete substrate 720, the inner perimeter first lateral edge 727 of the second discrete substrate 720, and the inner perimeter second lateral edge 728 of the second discrete substrate 720. Because this area also contains two layers of substrate (located between adjacent single layers of substrate), it is referred to as the second dual layer area 750. The first dual layer area 740 and the second dual layer area 750 add up to form the dual layer of substrate. As a non-limiting example, utilizing the embodiment shown in FIGS. 50-52, if the first dual layer area 740 is 20 cm² and the second dual layer area 750 is 10 cm², the dual layer of substrate for the multi-component topsheet 700 is 30 cm².

Still referring to FIGS. 50-52 and 55-57, from a top view, the areas of the multi-component topsheet 700 that are not the dual layer of substrate are defined as a single layer of substrate. The single layer of substrate for this particular embodiment of multi-component topsheet 700 consists of three single layer areas added together. The first single layer area is the area, from a top view, contained by a perimeter consisting of the first lateral edge 713 of the first discrete substrate 710, the second lateral edge 714 of the first discrete substrate 710, the first longitudinal edge 711 of the first discrete substrate 710, and the second longitudinal edge 712 of the first discrete substrate 710, minus the area contained by a perimeter consisting of the first lateral edge 723 of the second discrete substrate 720, the second lateral edge 724 of the second discrete substrate 720, the first longitudinal edge 721 of the second discrete substrate 720, and the second longitudinal edge 722 of the second discrete substrate 720. The second single layer area is the area, from a top view, contained by a perimeter consisting of the inner perimeter first lateral edge 717 of the first discrete substrate 710, the inner perimeter second lateral edge 718 of the first discrete substrate 710, the inner perimeter first longitudinal edge 715 of the first discrete substrate 710, and the inner perimeter second longitudinal edge 716 of the first discrete substrate 710, minus the area contained by a perimeter consisting of the first lateral edge 733 of the third discrete substrate 730, the second lateral edge 734 of the third discrete substrate 730, the first longitudinal edge 731 of the third discrete substrate 730, and the second longitudinal edge 732 of the third discrete substrate 730. The third single layer area is the area, from a top view, contained by a perimeter consisting of the inner perimeter first lateral edge 727 of the second discrete substrate 720, the inner perimeter second lateral edge 728 of the second discrete substrate 720, the inner perimeter first longitudinal edge 725 of the second discrete substrate 720, and the inner perimeter second longitudinal edge 726 of the second discrete substrate 720. The first, second, and third single areas add up to form the single layer of substrate. As a non-limiting example, utilizing the embodiment shown in FIGS. 50-52, if the first single layer area is 120 cm² and the second single layer area is 20 cm², and the third single layer area is 50 cm², the single layer of substrate for the multi-component topsheet 700 is 190 cm².

Referring to the non-limiting embodiments depicted in FIGS. 46-57, the distance between the first lateral edge 705 of the first discrete substrate 710 and the inner perimeter first lateral edge 717 of the first discrete substrate 710 may be between about 20 mm and about 70 mm. The distance between the inner perimeter second lateral edge 718 of the first discrete substrate 710 and the second lateral edge 714 of the first discrete substrate 710 may be between about 20 mm and about 70 mm. The distance between the first lateral edge 713 of the first discrete substrate 710 and the first lateral edge 723 of the second discrete substrate 720 may be between about 16 mm and about 66 mm. The distance between the second lateral edge 724 of the second discrete substrate 720 and the second lateral edge 714 of the first discrete substrate 710 may be between about 16 mm and about 66 mm. The distance between the first lateral edge 723 of the second discrete substrate 720 and the second lateral edge 724 of the second discrete substrate 720 may be between about 40 mm and about 120 mm. The distance between the first lateral edge 723 of the second discrete substrate 720 and the inner perimeter first lateral edge 717 of the first discrete substrate 710 may be between about 4 mm and about 24 mm. The distance between the inner perimeter second lateral edge 718 of the first discrete substrate 710 and the second lateral edge 724 of the second discrete substrate 720 may be between about 4 mm and about 24 mm.

Figure 46:
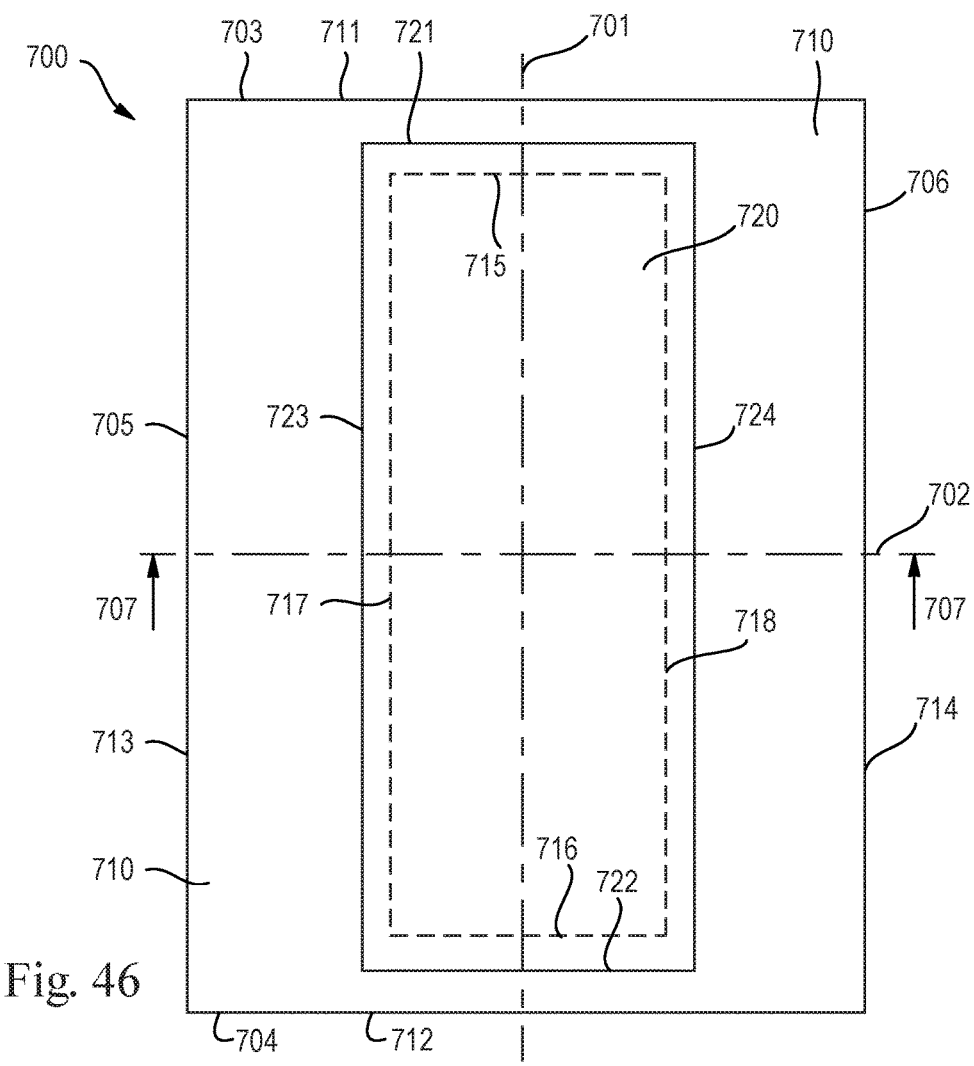
FIG. 46 is a schematic illustration of a top view of a multi-component topsheet in accordance with the present disclosure.
Figure 47:
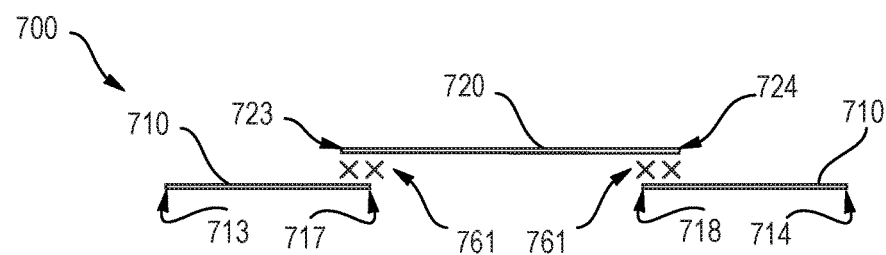
FIG. 47 is a schematic illustration of a cross-sectional view of the multi-component topsheet of FIG. 46.
Figure 48:
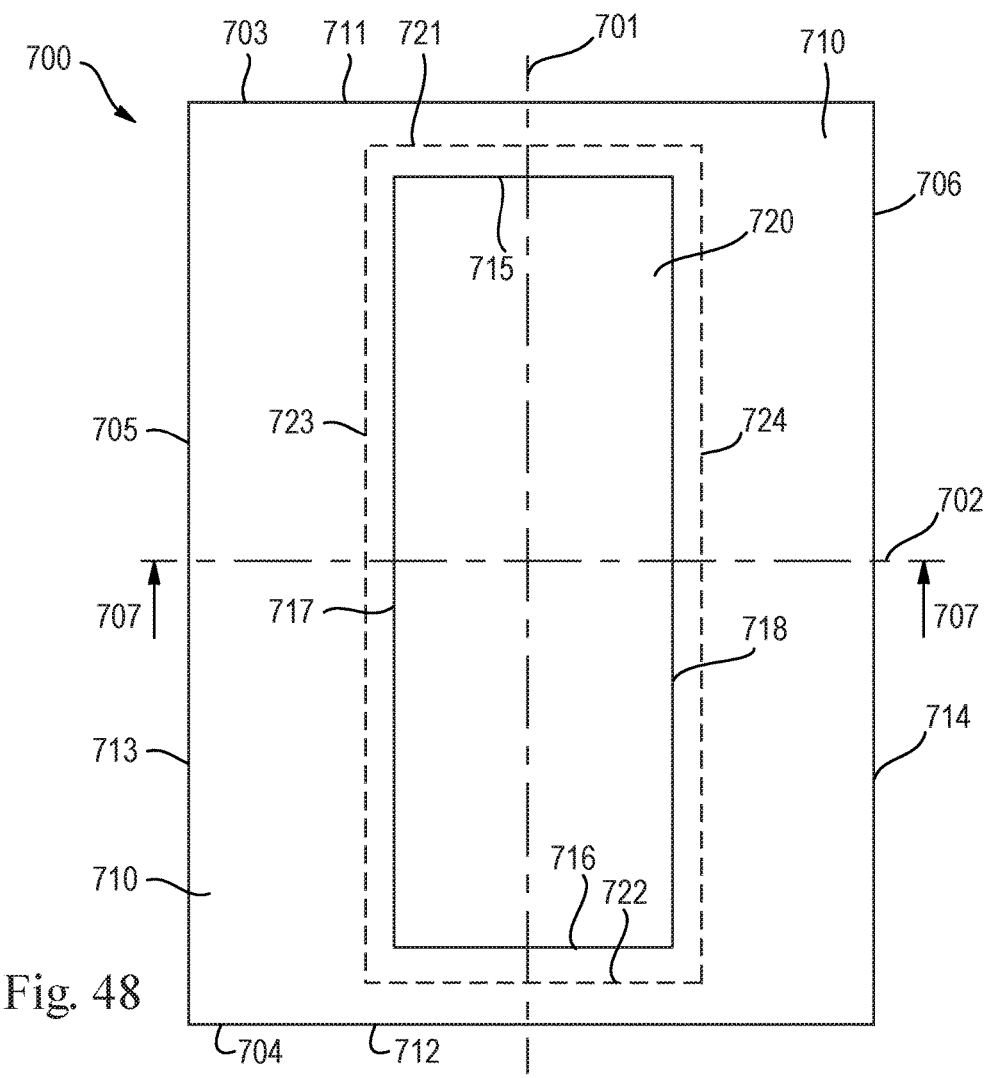
FIG. 48 is a schematic illustration of a top view of a multi-component topsheet in accordance with the present disclosure.
Figure 49:
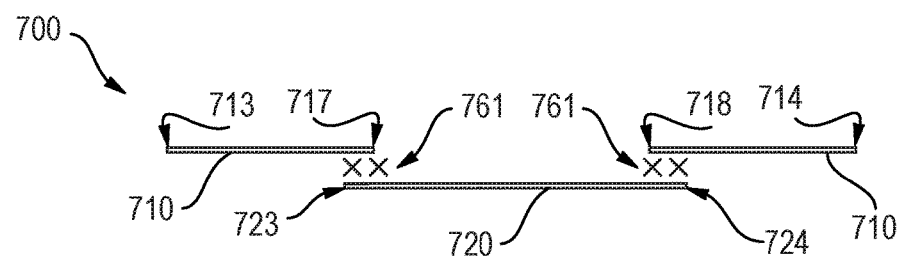
FIG. 49 is a schematic illustration of a cross-sectional view of the multi-component topsheet of FIG. 48.
Figure 50:
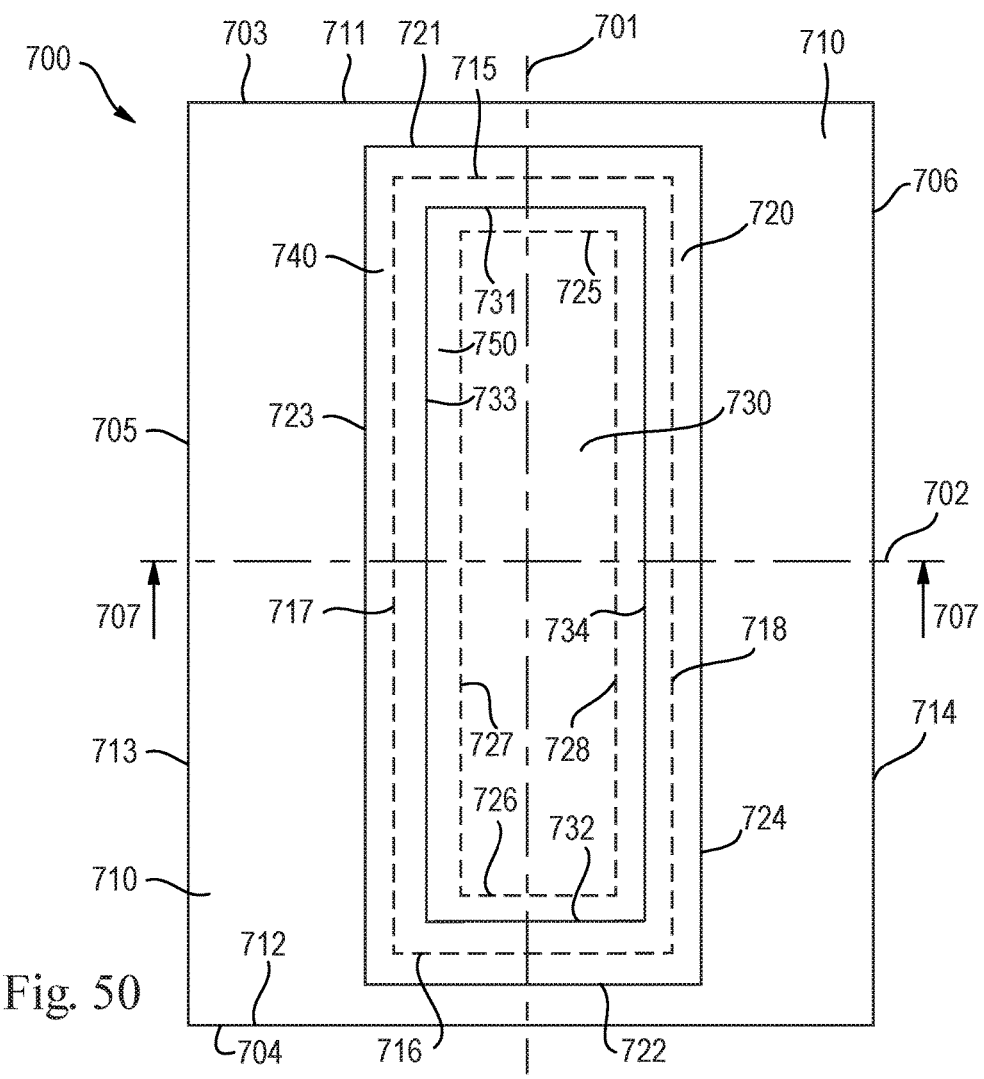
FIG. 50 is a schematic illustration of a top view of a multi-component topsheet in accordance with the present disclosure.
Figure 51:
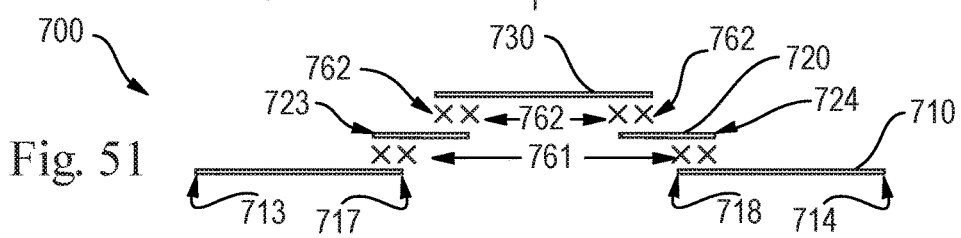
FIG. 51 is a schematic illustration of a cross-sectional view of the multi-component topsheet of FIG. 50.
Figure 52:
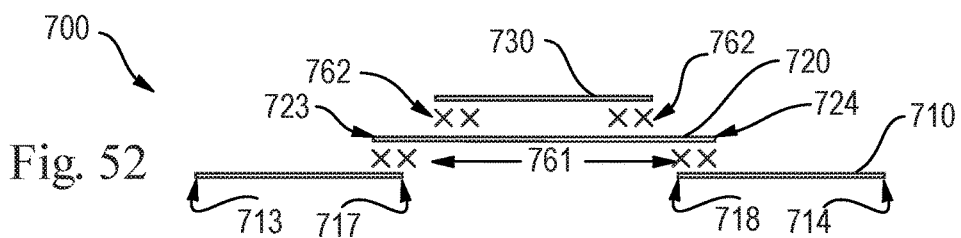
FIG. 52 is a schematic illustration of a cross-sectional view of the multi-component topsheet of FIG. 50.

As shown in FIG. 46, looking down on a top view of the body facing side of an embodiment of the multi-component topsheet 700 (and also detailed in the cross sectional view of FIG. 47), the second discrete substrate 720 is disposed above the first discrete substrate 710. Accordingly, the overlap between the first discrete substrate 710 and the second discrete substrate 720 includes the garment facing side of the second discrete substrate contacting the body facing side of the first discrete substrate. Alternatively, as shown in FIG. 48, looking down on a top view of the body facing side of an embodiment of the multi-component topsheet 700 (and also detailed in the cross sectional view of FIG. 49), the second discrete substrate 720 is disposed below the first discrete substrate 710. Accordingly, the overlap between the first discrete substrate 710 and the second discrete substrate 720 includes the body facing side of the second discrete substrate contacting the garment facing side of the first discrete substrate. In the embodiment of multi-component topsheet 700 that includes a third discrete substrate 730, the overlap between the second discrete substrate 720 and the third discrete substrate may have the third discrete substrate located above (FIGS. 50-52 and 55-57) or below the second discrete substrate.

In some embodiments, the single layer of substrate may comprise about 75% or more of the total area of the multi-component topsheet 700, and the dual layer of substrate may comprise about 25% or less of the total area of the multi-component topsheet 700. In other embodiments, the single layer of substrate may comprise about 65% or more, about 70% or more, about 80% or more, about 85% or more, about 90% or more, or about 95% or more of the total area of the multi-component topsheet 700, and the dual layer of substrate may comprise about 35% or less, about 30% or less, about 25% or less, about 15% or less, about 10% or less, or about 5% or less of the total area of the multi-component topsheet 700.

The first discrete substrate 710, the second discrete substrate 720, and/or the optional third discrete substrate 730 may be composed of any one or more of the three-dimensional substrates detailed herein. In some embodiments, the second discrete substrate 720 is composed of an embodiment of the three-dimensional substrates detailed herein, and the first discrete substrate 710 is made of traditional topsheet materials, such as P10.

When viewed from the top, the multi-component topsheets 700 may have one or more shapes, patterns or other distinct visible interfaces between the first discrete substrate 710 and the second discrete substrate 720 (and in certain embodiments, between the second discrete substrate and the third discrete substrate 730). Depending on whether the second discrete substrate 720 is located above (as depicted in FIGS. 46-47, 50-52 and 55-57) or below (as depicted in FIGS. 48-49 and 53-54) the first discrete substrate 710, the longitudinal or lateral edges of the first or second discrete substrates may determine the shape of the visible interface. For example, in the embodiment depicted in FIG. 46, the shape or pattern of the first lateral edge 723 of the second discrete substrate 720 will determine the visible interface adjacent the inner perimeter first lateral edge 717 of the first discrete substrate 710, and the shape or pattern of the second lateral edge 724 of the second discrete substrate 720 will determine the visible interface adjacent the inner perimeter second lateral edge 718 of the first discrete substrate 710. In the embodiment depicted in FIG. 48, the shape or pattern of the inner perimeter first lateral edge 717 of the first discrete substrate 710 will determine the visible interface adjacent the first lateral edge 723 of the second discrete substrate 720 and the shape or pattern of the inner perimeter second lateral edge 718 of the first discrete substrate 710 will determine the visible interface adjacent the second lateral edge 724 of the second discrete substrate 720.

Figure 58:
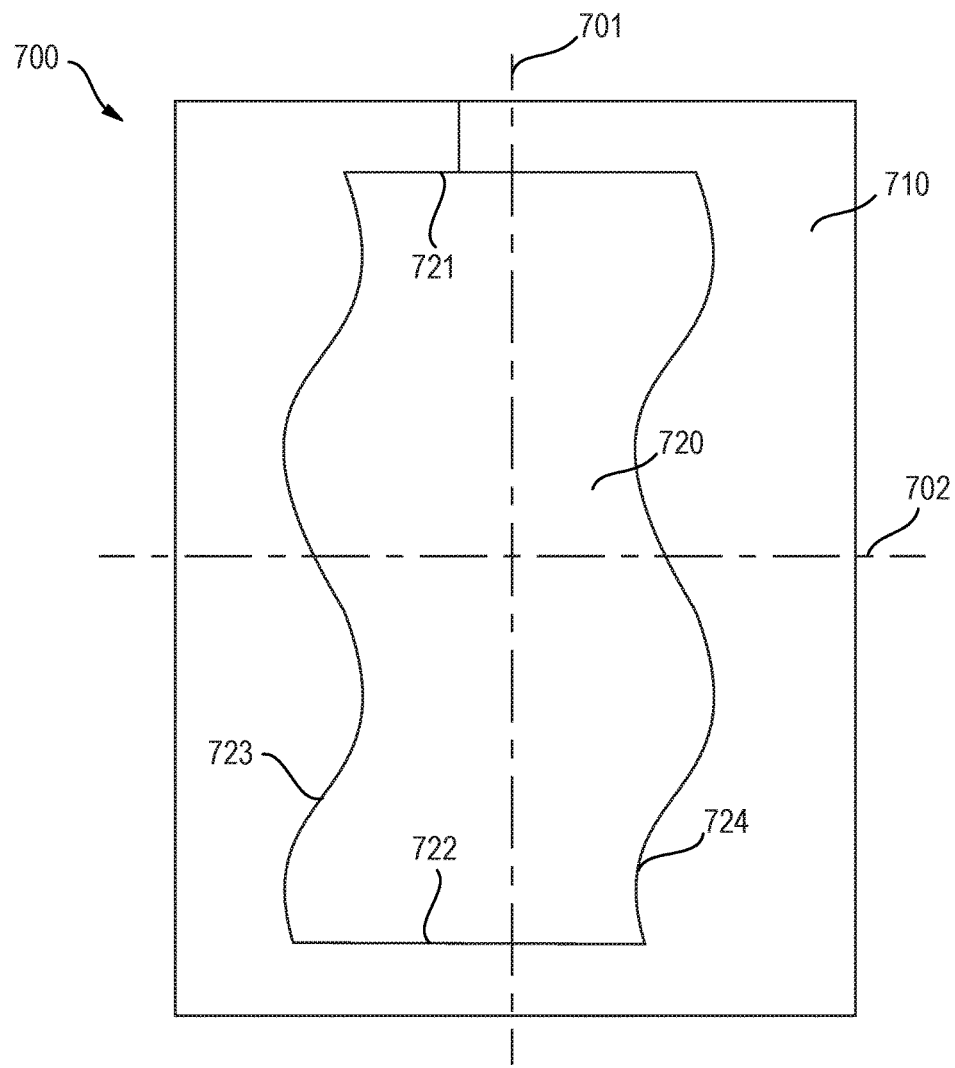
FIG. 58 is a schematic illustration of a top view of a multi-component topsheet in accordance with the present disclosure.
Figure 59:
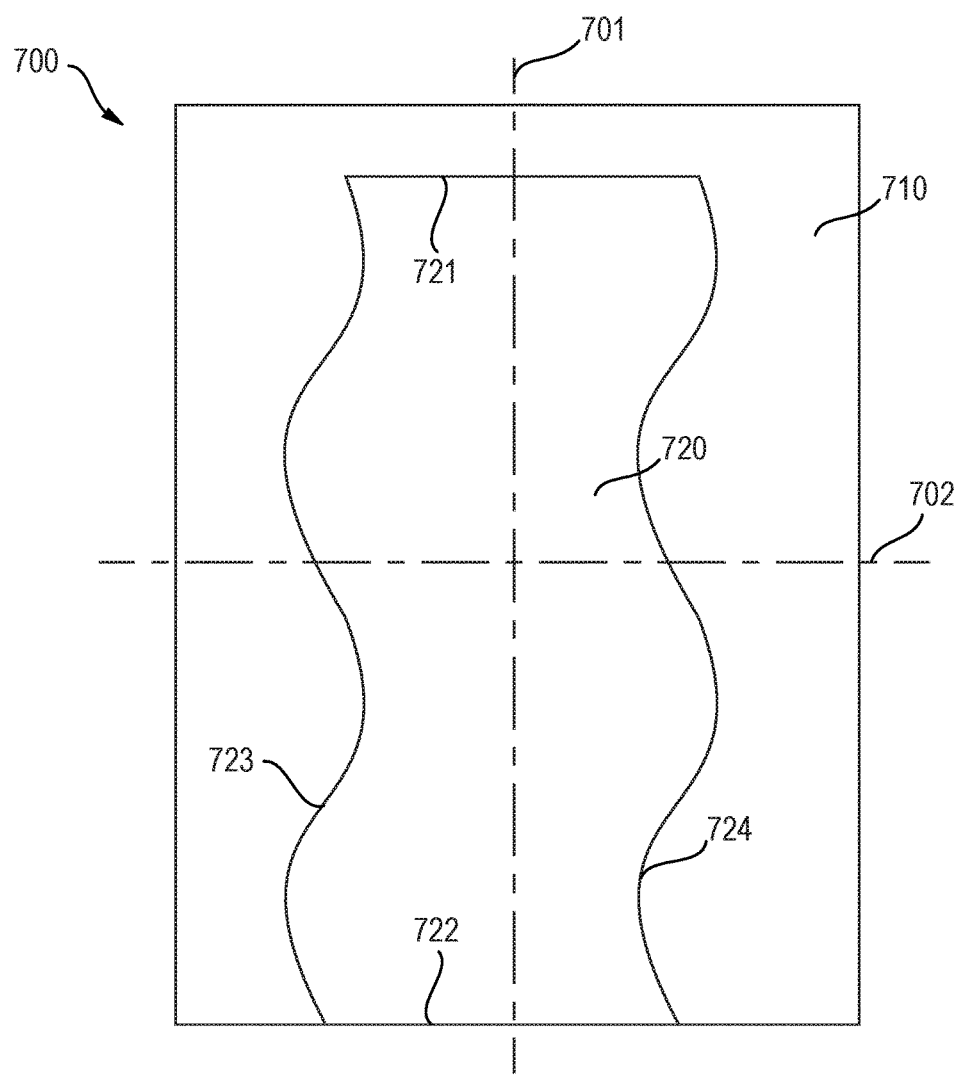
FIG. 59 is a schematic illustration of a top view of a multi-component topsheet in accordance with the present disclosure.
Figure 60:
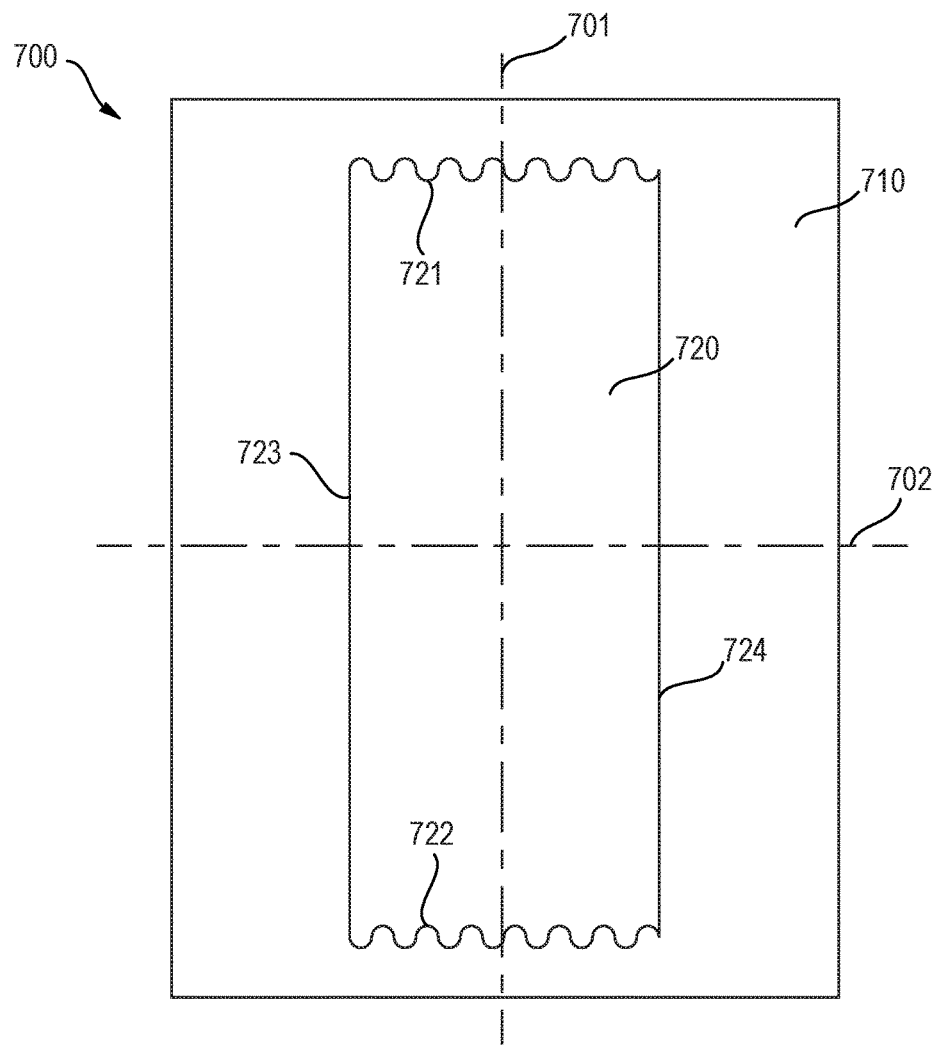
FIG. 60 is a schematic illustration of a top view of a multi-component topsheet in accordance with the present disclosure.
Figure 61:
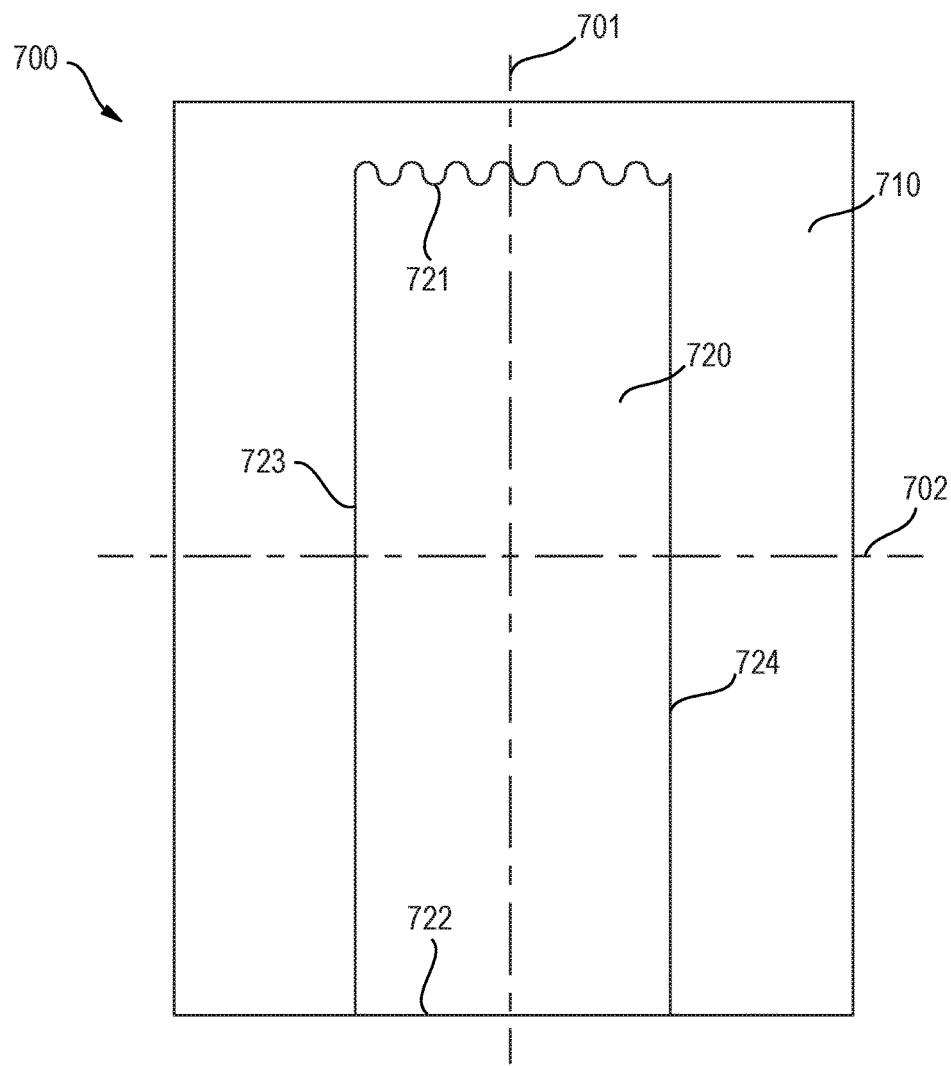
FIG. 61 is a schematic illustration of a top view of a multi-component topsheet in accordance with the present disclosure.

In any of the non-limiting embodiments of FIGS. 46-57, the lateral edges or longitudinal edges that create the visible interface between the second discrete layer 720 and the first discrete layer 710 (and in certain embodiments, between the second discrete substrate and the third discrete substrate 730) may be linear (i.e., straight line) or non-linear (i.e., not a straight line) and symmetrical or asymmetrical, about either the lateral or longitudinal axes 701, 702. FIGS. 46-52 are examples of linear, symmetrical visible interfaces. For non-limiting examples of additional visible interfaces (dependent on any combination of longitudinal and/or lateral edges of the first, second, and/or third discrete substrates), please refer to FIGS. 58-61. FIG. 58 depicts a multi-component topsheet 700 with a visible interface that is non-linear and asymmetrical about the longitudinal axis 701. One way to achieve such a visible interface is to have a multi-component topsheet 700 with the second discrete substrate 720 disposed above the first discrete substrate 710, and the first lateral edge 723 and the second lateral edge 724 of the second discrete substrate are non-linear and asymmetrical about the longitudinal axis 701 of the topsheet. In this particular example, repeating waves form the visible interface. However, in other embodiments, all kinds of waves may be used, such as sine waves, saw tooth waves, square waves, etc. FIG. 59 is another example of a multi-component topsheet 700 with a non-linear and asymmetrical visible interface. FIG. 60 depicts a multi-component topsheet 700 with a visible interface that is non-linear and symmetrical about the lateral axis 702. One way to achieve such a visible interface is to have a multi-component topsheet 700 with the second discrete substrate 720 disposed above the first discrete substrate 710 and the first longitudinal edge 721 and the second longitudinal edge 722 of the second discrete substrate are non-linear and symmetrical about the lateral axis 702 of the topsheet. FIG. 61 is an example of a multi-component topsheet 700 with a non-linear and asymmetrical visible interface about the lateral axis 702.

In some embodiments of multi-component topsheet 700, there may be a color difference between first discrete substrate 710 and the second discrete substrate 720 and/or, if present, the third discrete substrate 730. For example the first discrete substrate 710 may be a first color (e.g., purple, green, teal, blue), and the second discrete substrate 720 may be a second, different color, such as white. Alternatively, the first discrete substrate 710 may be white and the second discrete substrate 720 may be a different color. Alternatively, the first discrete substrate 710 and the second discrete substrate 720 can be a first and/or a second color, and the third discrete substrate 730 can be a different, third color.

Figure 62:
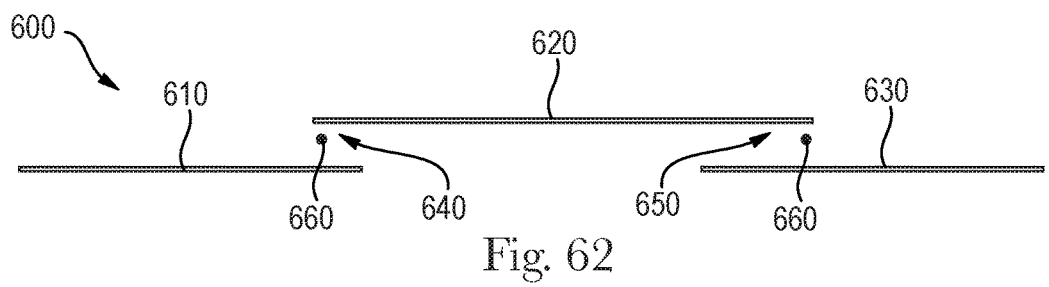
FIG. 62 is a schematic illustration of a cross-sectional view of a multi-component topsheet in accordance with the present disclosure.
Figure 63:
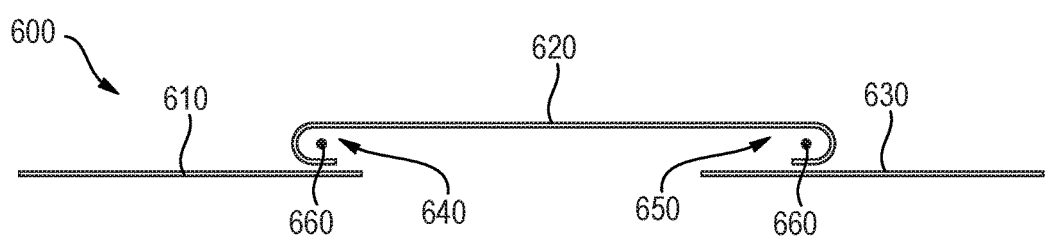
FIG. 63 is a schematic illustration of a cross-sectional view of a multi-component topsheet in accordance with the present disclosure.
Figure 64:
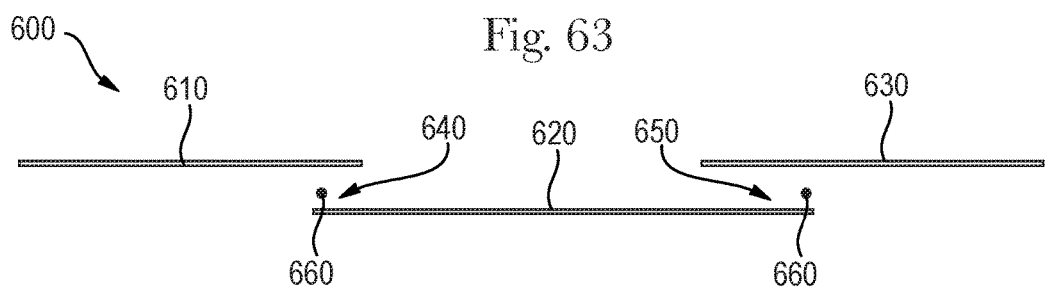
FIG. 64 is a schematic illustration of a cross-sectional view of a multi-component topsheet in accordance with the present disclosure.
Figure 65:
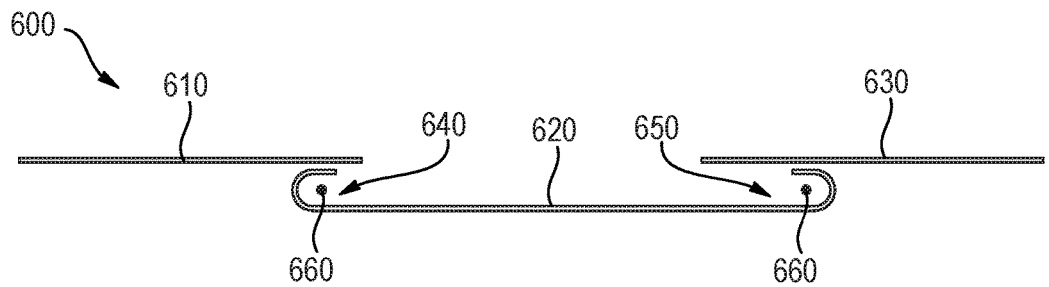
FIG. 65 is a schematic illustration of a cross-sectional view of a multi-component topsheet in accordance with the present disclosure.

In some embodiments of multi-component topsheets 600, 700, one or more elastics may be disposed in the overlap between first discrete substrate and second discrete substrate and/or the overlap between second discrete substrate and third discrete substrate. As depicted in FIGS. 62-65, the multi-component topsheet 600 may have one or more elastics 660 disposed in the first dual layer area 640 and/or the second dual layer area 650. As depicted in FIG. 62, the second discrete substrate 620 may be disposed on top of the first discrete substrate 610 and the third discrete substrate 630, with the elastics 660 located within the overlaps between the substrates. As depicted in FIG. 64, the second discrete substrate 620 may be disposed below the first discrete substrate 610 and the third discrete substrate 630, with the elastics 660 located within the overlaps between the substrates. As depicted in FIGS. 63 and 65, a portion of the second discrete substrate 620 may wrap around the elastics 660, thereby creating a triple layer of substrate in the overlap regions 640, 650.

Figure 66:
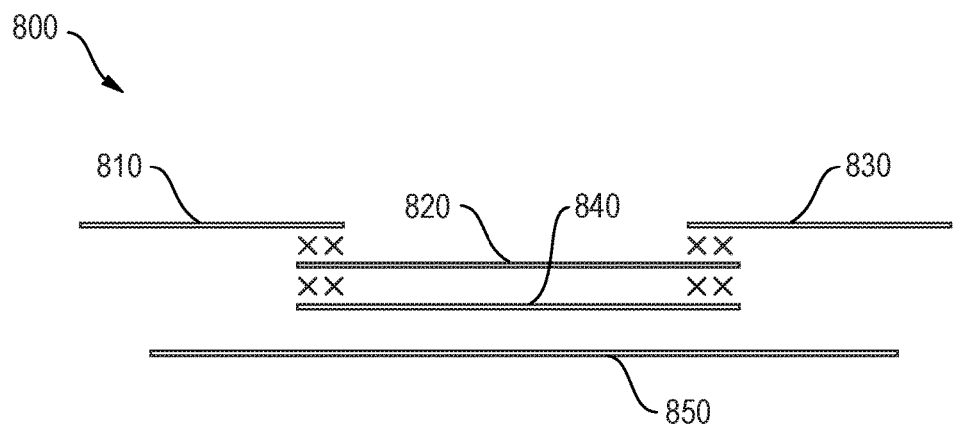
FIG. 66 is a schematic illustration of an absorbent article in accordance with the present disclosure.
Figure 67:
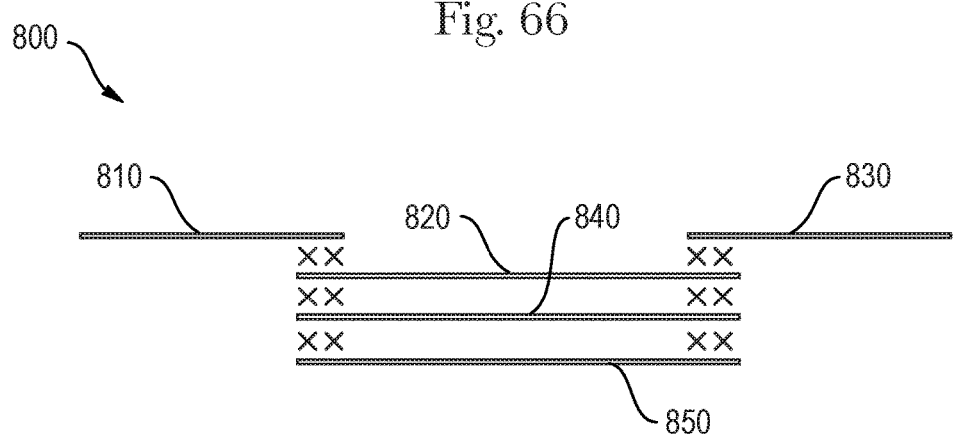
FIG. 67 is a schematic illustration of an absorbent article in accordance with the present disclosure.
Figure 68:
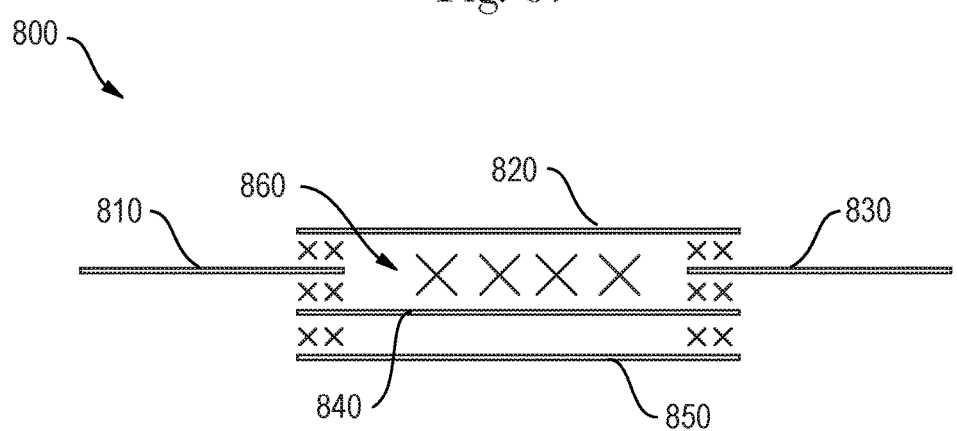
FIG. 68 is a schematic illustration of an absorbent article in accordance with the present disclosure.

In some embodiments of absorbent articles 800, as depicted in FIGS. 66-68, the multi-component topsheets 600, 700 may be combined with additional absorbent article elements such as acquisition layers, distributions layers, absorbent layers, etc. As one non-limiting example shown in FIG. 66, the absorbent article includes a multi-component topsheet 800 that comprises first discrete substrate 810, second discrete substrate 820, third discrete substrate 830, wherein the multi-component topsheet is joined (e.g., mechanical bonding and/or adhesive) to acquisition layer 840, which sits above a distribution layer 850. The acquisition layer 840 and the distribution layer 850 can be the same lateral width as the second discrete substrate 820 of the multi-component topsheet, or wider or narrower than the second discrete substrate.

As another non-limiting example shown in FIG. 67, the absorbent article includes a multi-component topsheet 800 that comprises first discrete substrate 810, second discrete substrate 820, third discrete substrate 830, wherein the multi-component topsheet is joined (e.g., mechanical bonding and/or adhesive) to acquisition layer 840, which is joined (e.g., mechanical bonding and/or adhesive) to a distribution layer 850. The acquisition layer 840 and the distribution layer 850 can be the same lateral width as the second discrete substrate 820 of the multi-component topsheet, or wider or narrower than the second discrete substrate.

As another non-limiting example shown in FIG. 68, the absorbent article includes a multi-component topsheet 800 that comprises first discrete substrate 810, second discrete substrate 820, third discrete substrate 830, wherein the multi-component topsheet is joined (e.g., mechanical bonding and/or adhesive) to acquisition layer 840, which is joined (e.g., mechanical bonding and/or adhesive) to a distribution layer 850. The acquisition layer 840 and the distribution layer 850 can be the same lateral width as the second discrete substrate 820 of the multi-component topsheet 800, or wider or narrower than the second discrete substrate. In such embodiment, the second discrete substrate 820 sits above the first discrete substrate 810 and the third discrete substrate 830, but the second discrete substrate is joined (e.g., mechanical bonding 860 and/or adhesive) in the lateral open space between first and third discrete substrates to the acquisition layer 840.

Test Methods

Condition all samples at about 23° C.±2° C. and about 50%±2% relative humidity for 2 hours prior to testing.

Aperture Test

Aperture dimensions, effective aperture area, and % effective open area measurements are performed on images generated using a flat bed scanner capable of scanning in reflectance mode at a resolution of 6400 dpi and 8 bit grayscale (a suitable scanner is the Epson Perfection V750 Pro, Epson, USA). Analyses are performed using ImageJ software (v.s 1.46, National Institute of Health, USA) and calibrated against a ruler certified by NIST. A steel frame (100 mm square, 1.5 mm thick with an opening 60 mm square) is used to mount the specimen and a black glass tile (P/N 11-0050-30, available from HunterLab, Reston, Va.) is used as the background for the scanned images.

Take the steel frame and place double-sided adhesive tape on the bottom surface surrounding the interior opening. To obtain a specimen, lay the absorbent article flat on a lab bench with the wearer-facing surface directed upward. Remove the release paper of the tape, and adhere the steel frame to the topsheet (substrates described herein may only form a portion of the topsheet, e.g., by being positioned on the topsheet—the three-dimensional material is what is sampled) of the absorbent article. Using a razor blade, excise the top sheet from the underling layers of the absorbent article around the outer perimeter of the frame. Carefully remove the specimen such that its longitudinal and lateral extension is maintained. A cryogenic spray (such as Cyto-Freeze, Control Company, Houston Tex.) can be used to remove the topsheet specimen from the underlying layers, if necessary. Five replicates obtained from five substantially similar absorbent articles are prepared for analysis.

Place the ruler on the scanner bed, close the lid and acquire a 50 mm by 50 mm calibration image of the ruler in reflectance mode at a resolution of 6400 dpi and 8 bit grayscale. Save the image as an uncompressed TIFF format file. Lift the lid and remove the ruler. After obtaining the calibration image, all specimens are scanned under the same conditions and measured based on the same calibration file. Next, place the framed specimen onto the center of the scanner bed with the wearer-facing surface of the specimen facing the scanner's glass surface. Place the black glass tile on top of the frame covering the specimen, close the lid and acquire a scanned image. In like fashion scan the remaining four replicates.

Open the calibration file in ImageJ and perform a linear calibration using the imaged ruler, with the scale set to Global so that the calibration will be applied to subsequent specimens. Open a specimen image in ImageJ. View the histogram and identify the gray level value for the minimum population located between the dark pixel peak of the holes and the lighter pixel peak of the nonwoven. Threshold the image at the minimum gray level value to generate a binary image. In the processed image, the apertures appear as black and nonwoven as white.

Select the analyze particles function. Set the minimum aperture area exclusion limit to 0.3 mm$^2$ and for the analysis to exclude the edge apertures. Set the software to calculate: effective aperture area, perimeter, feret (length of the aperture) and minimum feret (width of the aperture). Record the average effective aperture area to the nearest 0.01 mm$^2$, and the average perimeter to the nearest 0.01 mm. Again select the analyze particles function, but his time set the analysis to include the edge holes as it calculates the effective aperture areas. Sum the effective aperture areas (includes whole and partial apertures) and divide by the total area included in the image (2500 mm$^2$). Record as the % effective open area to the nearest 0.01%.

In like fashion analyze the remaining four specimen images. Calculate and report the average effective aperture area to the nearest 0.01 mm$^2$, the average aperture perimeter to the nearest 0.01 mm, feret and minimum feret to the nearest 0.01 mm, and the % effective open area to the nearest 0.01% for the five replicates.

Height Tests

Substrate projection heights and overall substrate heights are measured using a GFM MikroCAD Premium instrument commercially available from GFMesstechnik GmbH, Teltow/Berlin, Germany. The GFM MikroCAD Premium instrument includes the following main components: a) a DLP projector with direct digital controlled micro-mirrors; b) a CCD camera with at least a 1600×1200 pixel resolution; c) projection optics adapted to a measuring area of at least 60 mm×45 mm; d) recording optics adapted to a measuring area of at least 60 mm×45 mm; e) a table tripod based on a small hard stone plate; f) a blue LED light source; g) a measuring, control, and evaluation computer running ODSCAD software (version 6.2, or equivalent); and h) calibration plates for lateral (x-y) and vertical (z) calibration available from the vendor.

The GFM MikroCAD Premium system measures the surface height of a sample using the digital micro-mirror pattern fringe projection technique. The result of the analysis is a map of surface height (z-directional or z-axis) versus displacement in the x-y plane. The system has a field of view of 60×45 mm with an x-y pixel resolution of approximately 40 microns. The height resolution is set at 0.5 micron/count, with a height range of +/−15 mm. All testing is performed in a conditioned room maintained at about 23±2° C. and about 50±2% relative humidity.

A steel frame (100 mm square, 1.5 mm thick with an opening 70 mm square) is used to mount the specimen. Take the steel frame and place double-sided adhesive tape on the bottom surface surrounding the interior opening. To obtain a specimen, lay the absorbent article flat on a bench with the wearer-facing surface directed upward. Remove the release paper of the tape, and adhere the steel frame to the topsheet (substrates described herein may only form a portion of the topsheet, e.g., by being positioned on the topsheet—the three-dimensional material is what is sampled) of the absorbent article. Using a razor blade, excise the topsheet from the underling layers of the absorbent article around the outer perimeter of the frame. Carefully remove the specimen such that its longitudinal and lateral extension is maintained. A cryogenic spray (such as Cyto-Freeze, Control Company, Houston Tex.) can be used to remove the topsheet specimen from the underling layers, if necessary. Five replicates obtained from five substantially similar absorbent articles are prepared for analysis.

Calibrate the instrument according to manufacturer's specifications using the calibration plates for lateral (x-y axis) and vertical (z axis) available from the vendor.

Place the steel plate and specimen on the table beneath the camera, with the wearer-facing surface oriented toward the camera. Center the specimen within the camera field of view, so that only the specimen surface is visible in the image. Allow the specimen to lay flat with minimal wrinkles.

Collect a height image (z-direction) of the specimen by following the instrument manufacturer's recommended measurement procedures. Select the Technical Surface/Standard measurement program with the following operating parameters: Utilization of fast picture recording with a 3 frame delay. Dual phase shifts are used with 1) 16 pixel stripe width with a picture count of 12 and 2) 32 pixel stripe width with a picture count of 8. A full Graycode starting with pixel 2 and ending with pixel 512. After selection of the measurement program, continue to follow the instrument manufacturer's recommended procedures for focusing the measurement system and performing the brightness adjustment. Perform the 3D measurement then save the height image and camera image files.

Load the height image into the analysis portion of the software via the clipboard. The following filtering procedure is then performed on each image: 1) removal of invalid points; 2) removal of peaks (small localized elevations); 3) polynomial filtering of the material part with a rank of n=5, with exclusion of 30% of the peaks and 30% of the valleys from the material part, and 5 cycles.

Projection Height Test

Draw a line connecting the peaks of a series of projections, with the line crossing a non-apertured land area located between each of the projections. Generate a sectional image of the height image along the drawn line. Along the sectional line, measure the vertical height (z-direction) difference between the peak of the projection and the adjacent valley of the land area. Record the height to the nearest 0.1 µm. Average together 10 different projection peak to land area height measures and report this value to the nearest 0.1 µm. This is the projection height.

Recess Height Test

Subtract the projection height from the overall substrate height to obtain the recess height. This should be done with each of the ten measurements from the Projection Height Test and the Overall Substrate Height Test. Average together the ten recess heights and report this value to the nearest 0.1 µm. This is the recess height.

Overall Substrate Height Test

Draw a line connecting the peaks of a series of projections, with the line crossing the center of an aperture located between each of the projections and within a recess. Generate a sectional image of the height image along the drawn line. Along the sectional line, measure the vertical height difference between the peak of the projection and the adjacent base of the recess. Record the height to the nearest 0.1 µm. Average together 10 different projection peak to base of recess height measures and report this value to the nearest 0.1 µm. This is the overall substrate height.

Average Aperture Spacing Test

Lateral Axis Aperture Spacing and Longitudinal Axis Aperture Spacing are performed on images generated using a flat bed scanner capable of scanning in reflectance mode at a resolution of 6400 dpi and 8 bit grayscale (a suitable scanner is the Epson Perfection V750 Pro, Epson, USA). Analyses are performed using ImageJ software (v.s 1.46, National Institute of Health, USA) and calibrated against a ruler certified by NIST. A steel frame (100 mm square, 1.5 mm thick with an opening 60 mm square) is used to mount the specimen and a black glass tile (P/N 11-0050-30, available from HunterLab, Reston, Va.) is used as the background for the scanned images. Testing is performed at about 23° C.±2° C. and about 50%±2% relative humidity.

Take the steel frame and place double-sided adhesive tape on the bottom surface surrounding the interior opening. To obtain a specimen, lay the absorbent article flat on a lab bench with the wearer-facing surface directed upward. Remove the release paper of the tape, and adhere the steel frame to the topsheet of the absorbent article. Using a razor blade excise the topsheet (i.e., the three dimensional substrate that forms all of or part of the wearer-facing surface) from the underling layers of the absorbent article around the outer perimeter of the frame. Carefully remove the specimen such that its longitudinal and lateral extension is maintained. A cryogenic spray (such as Cyto-Freeze, Control Company, Houston Tex.) can be used to remove the topsheet specimen from the underling layers, if necessary. Five replicates obtained from five substantially similar absorbent articles are prepared for analysis. Condition the samples at about 23° C.±2° C. and about 50%±2% relative humidity for 2 hours prior to testing.

Place the ruler on the scanner bed, close the lid and acquire a 50 mm by 50 mm calibration image of the ruler in reflectance mode at a resolution of 6400 dpi and 8 bit grayscale. Save the image as an uncompressed TIFF format file. Lift the lid and remove the ruler. After obtaining the calibration image, all specimens are scanned under the same conditions and measured based on the same calibration file. Next, place the framed specimen onto the center of the scanner bed with the wearer-facing surface of the specimen facing the scanner's glass surface. Place the black glass tile on top of the frame covering the specimen, close the lid and acquire a scanned image. In a like fashion, scan the remaining four replicates.

Open the calibration file in ImageJ and perform a linear calibration using the imaged ruler, with the scale set to Global so that the calibration will be applied to subsequent specimens. Open a specimen image in ImageJ and perform the following measures:

Lateral Axis Aperture Spacing

Measure from a center point of one aperture to a center point of an adjacent aperture on the other side of a projection, wherein the projection is positioned between the two apertures. The measurement will be taken in a direction parallel to a lateral axis of the specimen across the projection. Report each distance to the nearest 0.1 mm. Take 5 random measurements in the specimen. Average the five values to and report the average lateral axis center to center spacing to the nearest 0.1 mm. Repeat this procedure for the additional four samples.

Longitudinal Axis Aperture Spacing

Measure from a center point of one aperture to a center point of an adjacent aperture on the other side of a projection, wherein the projection is positioned between the two apertures. The measurement will be taken in a direction parallel to a longitudinal axis of the specimen across the projection. Report each distance to the nearest 0.1 mm. Take 5 random measurements in the specimen. Average the five values to and report the average longitudinal axis center to center spacing to the nearest 0.1 mm. Repeat this procedure for the additional four samples.

Basis Weight Test

Basis weight of the three-dimensional substrates may be determined by several available techniques but a simple representative technique involves taking an absorbent article, removing any elastic which may be present and stretching the absorbent article to its full length. A punch die having an area of 45.6 cm$^2$ is then used to cut a piece of the substrate forming a topsheet, positioned on the topsheet, or forming a portion of the topsheet (the "topsheet" in this method), from the approximate center of the diaper or absorbent product in a location which avoids to the greatest extent possible any adhesive which may be used to fasten the topsheet to any other layers which may be present and removing the topsheet layer from other layers (using cryogenic spray, such as Cyto-Freeze, Control Company, Houston, Tex. if needed). The sample is then weighed and dividing by the area of the punch die yields the basis weight of the topsheet. Results are reported as a mean of 5 samples to the nearest 0.1 gram per square meter.

Descriptive Analysis Roughness Method

Surface Geometrical Roughness is measured using a Kawabata Evaluation System KES FB4 Friction tester with Roughness Sensor (available from Kato Tech Co., Japan). The instrument measures both surface friction and geometric roughness simultaneously, but herein only the geometric roughness (SMD value) is reported. All testing is performed at about 23° C.±2° C. and about 50%±2% relative humidity. Samples are preconditioned at about 23° C.±2° C. and about 50%±2% relative humidity for 2 hours prior to testing. The instrument is calibrated as per the manufacturer's instructions.

The absorbent article is placed, wearer-facing surface upward, onto a lab bench. The absorbent article's cuffs are clipped with scissors to facilitate the article lying flat. With scissors or a scalpel excise a specimen of the topsheet 20 cm long in the longitudinal direction of the absorbent article and 10 cm wide in the lateral direction of the absorbent article. Care should be taken in removing the specimen as to not distort the dimensions in either the longitudinal or lateral direction. Specimens are collected from a total of five substantially identical absorbent articles.

Turn on the KES FB4. The instrument should be allowed to warm up for at least 10 minutes before use. Set the instrument to a SMD sensitivity of 2×5, a testing velocity of 0.1, and a compression area of 2 cm. The roughness contractor compression (contact force) is adjusted to 10 gf. Place the topsheet specimen on the tester with the wearer-facing surface facing upward and the longitudinal dimension aligned with the test direction of the instrument. Clamp the specimen with an initial tension of 20 gf/cm. Initiate the test. The instrument will automatically take 3 measurements on the specimen. Record the MIU (Coefficient of Friction), MMD (Slip Stick), and SMD (Geometrical Roughness) value from each of the three measurements to the nearest 0.001 micron. Repeat in like fashion for the remaining four specimens.

Report Coefficient of Friction as an average of the 15 recorded values to the nearest 0.01. Report Slip Stick as an average of the 15 recorded values to the nearest 0.001. Report the Geometrical Roughness as an average of the 15 recorded values to the nearest 0.01 micron.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any embodiment disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications may be made without departing from the spirit and scope of the present disclosure. It is therefore intended to cover in the appended claims all such changes and modifications that are within the scope of this disclosure.

What is claimed is:

1. A multi-component topsheet for an absorbent article, the topsheet comprising:
   a) a first discrete substrate forming 80% or more of an outer perimeter of the topsheet; and
   b) a second discrete substrate comprising a first hydrophobic nonwoven layer and a second hydrophilic nonwoven layer, wherein 80% or more of an outer perimeter of the second discrete substrate is joined to the first discrete substrate;
   wherein the topsheet has a single layer of substrate in 75% or more of the total area of the topsheet and a dual layer of substrate in 25% or less of the total area of the topsheet;
   wherein the dual layer of substrate is formed from an overlap between the first discrete substrate and the second discrete substrate; and
   wherein the second discrete substrate comprises a plurality of recesses and projections, wherein the plurality of recesses and projections together form a first three-dimensional surface on a first side of the second discrete substrate and a second three-dimensional surface on a second side of the substrate, wherein a majority of the projections are formed by the first and second nonwoven layers, wherein the plurality of projections form enclosed dome shapes, wherein the majority of the projections have, according to the Projection Height Test, a z-dimensional height of between 500 μm and 4000 μm, and wherein a majority of the recesses define an aperture at a location most distal from a top surface of an adjacent projection, a majority of the recesses having, according to the Recess Height Test, a z-directional height of between 500 μm and 2000 μm.

2. The multi-component topsheet of claim 1, wherein the second discrete substrate has, according to the Overall Substrate Height Test, an overall z-directional height of between 1000 μm and 6000 μm.

3. The multi-component topsheet of claim 1, wherein a majority of the apertures of the second discrete substrate have, according to the Aperture Area Test, an aperture area of between 0.5 mm$^2$ and 3.0 mm$^2$.

4. The multi-component topsheet of claim 1, wherein the second discrete substrate, according to the Descriptive Analysis Roughness Test, has a surface roughness of between 3.1 and 3.5.

5. The multi-component topsheet of claim 4, wherein the first discrete substrate and the second discrete substrate have a difference, according to the Descriptive Analysis Roughness Test, in surface roughness of 15% or more.

6. The multi-component topsheet of claim 1, wherein four apertures are formed around each projection.

7. The multi-component topsheet of claim 1, wherein four projections are formed around each aperture.

8. The multi-component topsheet of claim 1, wherein the second discrete substrate is partially surrounded on three sides by the first discrete substrate.

9. The multi-component topsheet of claim 1, wherein the second discrete substrate is fully surrounded on four sides by the first discrete substrate.

10. The multi-component topsheet of claim 1, wherein the first discrete substrate is joined to the second discrete substrate through mechanical bonding.

11. The multi-component topsheet of claim 1, wherein a first lateral edge and a second lateral edge of the second discrete substrate both comprise an arcuate portion, and wherein the first and second lateral edges are symmetrical to each other about the longitudinal axis of the topsheet.

12. The multi-component topsheet of claim 1, wherein a first lateral edge and a second lateral edge of the second discrete substrate both comprise an arcuate portion, and wherein the first and second lateral edges are symmetrical to each other about the longitudinal axis of the topsheet.

13. The multi-component topsheet of claim 1, wherein the overlap between the first discrete substrate and the second discrete substrate comprises the garment facing side of the second discrete substrate contacting the body facing side of the first discrete substrate.

14. The multi-component topsheet of claim 1, wherein the overlap between the first discrete substrate and the second discrete substrate comprises the body facing side of the second discrete substrate contacting the garment facing side of the first discrete substrate.

15. The multi-component topsheet of claim 1, wherein at least one elastic is disposed in the overlap between the first discrete substrate and the second discrete substrate.

16. An absorbent article comprising:
the multi-component topsheet of claim 1;
a backsheet; and
an absorbent core positioned at least partially intermediate the backsheet and the topsheet.

17. The absorbent article of claim 16, wherein the second discrete substrate of the multi-component topsheet is joined to at least one of an acquisition layer and a distribution layer.

18. The absorbent article of claim 16, wherein the article is a diaper, a menstrual pad, a pant, or an adult incontinence product.

19. A multi-component topsheet for an absorbent article, the topsheet comprising:
a) a first discrete substrate forming an entire outer perimeter of the topsheet;
b) a second discrete substrate comprising a first hydrophobic layer and a second hydrophilic layer, wherein an outer perimeter of the second discrete substrate is joined to the first discrete substrate;
wherein the topsheet has a single layer of substrate in 75% or more of the total area of the topsheet and a dual layer of substrate in 25% or less of the total area of the topsheet;
wherein the dual layer of substrate is formed from an overlap between the first discrete substrate and the second discrete substrate; and
wherein the second discrete substrate comprises a plurality of recesses and projections, wherein the plurality of recesses and projections together form a first three-dimensional surface on a first side of the second discrete substrate and a second three-dimensional surface on a second side of the substrate, wherein a majority of the projections are formed by the first and second layers and form hollow portions under a portion of the first and second layers, wherein the plurality of projections form enclosed dome shapes, wherein the majority of the projections have, according to the Projection Height Test, a z-dimensional height of between 500 μm and 4000 μm, and wherein a majority of the recesses define an aperture at a location most distal from a top surface of an adjacent projection, a majority of the recesses having, according to the Recess Height Test, a z-directional height of between 500 μm and 2000 μm.

20. An absorbent article comprising:
a) a multi-component topsheet, the topsheet comprising:
i) a first discrete substrate forming an entire outer perimeter of the topsheet;
ii) a second discrete substrate comprising a first hydrophobic nonwoven layer and a second hydrophilic nonwoven layer,
wherein an outer perimeter of the second discrete substrate is engaged with the first discrete substrate;
wherein the topsheet has a single layer of substrate in 75% or more of the total area of the topsheet and a dual layer of substrate in 25% or less of the total area of the topsheet;
wherein the dual layer of substrate is formed from an overlap between the first discrete substrate and the second discrete substrate; and
wherein the second discrete substrate comprises a plurality of recesses and projections, wherein the plurality of recesses and projections together form a first three-dimensional surface on a first side of the second discrete substrate and a second three-dimensional surface on a second side of the substrate, wherein a majority of the projections are formed by the first and second nonwoven layers and form hollow portions under a portion of the first and second layers, wherein the plurality of projections form enclosed dome shapes, wherein the majority of the projections have, according to the Projection Height Test, a z-dimensional height of between 500 μm and 4000 μm, and wherein a majority of the recesses define an aperture at a location most distal from a top surface of an adjacent projection, a majority of the recesses having, according to the Recess Height Test, a z-directional height of between 500 μm and 2000 μm;

b) a backsheet; and c) an absorbent core positioned at least partially intermediate the backsheet and the topsheet.

21. The absorbent article of claim 20, wherein the first and second nonwoven layers each comprise carded fibers.

22. The absorbent article of claim 20, wherein the first and second nonwoven layers form the enclosed dome shapes.

\* \* \* \* \*